United States Patent
Fox et al.

(10) Patent No.: US 11,485,987 B2
(45) Date of Patent: Nov. 1, 2022

(54) METHODS FOR INDUCING BIOORTHOGONAL REACTIVITY

(71) Applicants: Joseph M. Fox, Landenberg, PA (US); Colin Thorpe, Newark, DE (US); Amanda M. Tallon, Claymont, DE (US); Yixin Xie, Newark, DE (US); William Trout, Wilmington, DE (US); Ashlyn S. Cantrel, Catasauqua, PA (US); Julia E. Rosenberger, Wilmington, DE (US)

(72) Inventors: Joseph M. Fox, Landenberg, PA (US); Colin Thorpe, Newark, DE (US); Amanda M. Tallon, Claymont, DE (US); Yixin Xie, Newark, DE (US); William Trout, Wilmington, DE (US); Ashlyn S. Cantrel, Catasauqua, PA (US); Julia E. Rosenberger, Wilmington, DE (US)

(73) Assignee: University of Delaware, Newark, DE (US)

(*) Notice: Subject to any disclaimer, the term of this patent is extended or adjusted under 35 U.S.C. 154(b) by 0 days.

(21) Appl. No.: 17/132,532

(22) Filed: Dec. 23, 2020

(65) Prior Publication Data
US 2021/0164005 A1 Jun. 3, 2021

Related U.S. Application Data

(63) Continuation-in-part of application No. 16/062,423, filed as application No. PCT/US2016/066793 on Dec. 15, 2016, now Pat. No. 10,875,840.

(60) Provisional application No. 62/267,450, filed on Dec. 15, 2015.

(51) Int. Cl.
*C12P 17/12* (2006.01)
*C12P 17/16* (2006.01)

(52) U.S. Cl.
CPC .............. *C12P 17/165* (2013.01); *C12P 17/12* (2013.01)

(58) Field of Classification Search
CPC .......... C12P 17/165; C12P 17/12; C12P 17/16
See application file for complete search history.

(56) References Cited

U.S. PATENT DOCUMENTS

| | | | |
|---|---|---|---|
| 4,237,127 | A | 12/1980 | Parsons |
| 5,274,091 | A | 12/1993 | Coburn et al. |
| 8,236,949 | B2 | 8/2012 | Fox et al. |
| 2004/0115647 | A1 | 6/2004 | Paterson et al. |
| 2007/0026365 | A1 | 2/2007 | Friedrich et al. |
| 2007/0038475 | A1 | 2/2007 | Schlessinger et al. |
| 2008/0258006 | A1 | 10/2008 | Buscema et al. |
| 2009/0023916 | A1 | 1/2009 | Fox et al. |
| 2013/0052136 | A1 | 2/2013 | Chamney et al. |

FOREIGN PATENT DOCUMENTS

WO 2017106427 A1 6/2017

OTHER PUBLICATIONS

Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Branden et al., Introduction to Protein Structure, Garland Publishing Inc., New York, p. 247, 1991.*
Sadowski et al., Current Opinion in Structural Biology 19:357-362, 2009.*
Guo et al., PNAS 101(25):9205-9210, 2004.*
Blackman et al., "Tetrazine Ligation: Fast Bioconjugation Based on Inverse-Electron-Demand Diels-Alder Reactivity", Journal of the American Chemical Society, 2008, vol. 130, 27 pages.
Bowie et al., "Studies on Some Symmetrically and Unsymmetrically 3,6-Disubstituted 1,2-Dihydro-1,2,4,5-tetrazines including their Conversion into the Corresponding Tetrazines and 3,5-Disubstituted 4-Amino-1,2,4-triazoles", Journal of the Chemical Society, Perkin Transactions 1, (1972), pp. 2395-2399.

(Continued)

*Primary Examiner* — Delia M Ramirez
(74) *Attorney, Agent, or Firm* — RatnerPrestia

(57) ABSTRACT

A method for catalytically converting a dihydrotetrazine 1 into a tetrazine 2, wherein the dihydrotetrazine 1 comprises a first R group and a second R group, wherein the first R group is a substituted or unsubstituted aryl, heteroaryl, alkyl, alkenyl, alkynyl, carbonyl, or heteroatom-containing group, and the second R group is selected from the group consisting of H and substituted or unsubstituted aryl, heteroaryl, alkyl, alkenyl, alkynyl, carbonyl, and heteroatom-containing groups;

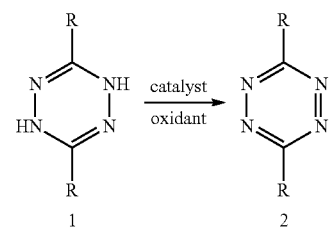

wherein the method comprises (a) providing the dihydrotetrazine 1 in a reaction medium, and (b) adding an enzyme as a catalyst and an oxidant to the reaction medium, whereby the dihydrotetrazine 1 is converted to the tetrazine 2.

18 Claims, 13 Drawing Sheets

Specification includes a Sequence Listing.

(56) References Cited

OTHER PUBLICATIONS

Chen et al., "Reactive Oxygen Species (ROS) Inducible DNA Cross-Linking Agents and Their Effect on Cancer Cells and Normal Lymphocytes", Journal of Medicinal Chemistry, 2014, vol. 57, pp. 4498-4510.

Cocquet et al., "A Mild and Efficient Procedure for Ring-Opening Reactions of Piperidine and Pyrrolidine Derivatives by Single Electron Transfer Photooxidation", Tetrahedron, 56, 2000, pp. 2975-2984.

Ebner et al., "Catalytic Oxidations with Oxygen: An Industrial Perspective", Active Oxygen in Chemistry, Structure Energetics and Reactivity in Chemistry Series (SEARCH Series), vol. 2, 1995, pp. 204-248.

Hu et al., "Catalytic N-radical cascade reaction of hydrazones by oxidative deprotonation electron transfer and TEMPO mediation", Nature Communications, 2016, pp. 1-12.

Kerth et al., "Synthesis and Characterization of 3,3'-Azobis(6-Amino-1,2,4,5-Tetrazine) DAAT—A New Promising Nitrogen-Rich Compound", Propellants, Explosives, Pyrotechnics, 27, 2002, pp. 111-118.

Lam et al., "Improving FRET Dynamic Range with Bright Green and Red Fluorescent Proteins", Nat. Methods, Oct. 2012, 9(10), 26 pages.

Lim et al., "Synthesis of Symmetric 3,6-Dlsubstituted-1,2,4,5-Tetrazines using an Activated Catalyst Prepared by the Reaction of Copper Nitrate with Excess Zinc in the Presence of Hydrazine Mono hydrate", Bulletin of the Korean Chemical Society, 1995: 16(4), pp. 374-377.

Rao et al., "Synthesis, structure analysis, and antitumor activity of 3,6-disubstituted-1,4-dihydro-1,2,4,5-tetrazine derivatives", Bioorganic & Medicinal Chemistry Letters, 16, 2006, pp. 3702-3705.

Robins et al., "Diazocinones: Synthesis, and Conformational Analysis", Journal of Organic Chemistry, 71, 2006, 29 pages.

Selvaraj et al., "An Efficient and Mild Oxidant for the Synthesis of S-tetrazines", Tetrahedron Letters, 2014, 55(34), 6 pages.

Taylor et al., "Design and Synthesis of Highly Reactive Dienphiles for the Teirazine-trans-Cyclooctene Ligation", J. Am. Chem. Soc., Jun. 29, 2011; 133(25), 13 pages.

Zhang et al., "Interfacial Bioorthogonal Cross-Linking", ACS Macro Lett., 2014, 3, 5 pages.

Zhang et al., "Rapid Bioorthogonal Chemistry Turn-on through Enzymatic or Long Wavelength Photocatalytic Activation of Tetrazine Ligation", Journal of the American Chemical Society, Apr. 14, 2016, 138, 66 pages.

International Preliminary Report on Patentability for International Application No. PCT/US2016/066793, dated Jun. 19, 2018, 6 pages.

International Search Report and Written Opinion for International Application No. PCT/US2016/066793, dated Feb. 26, 2016, 7 pages.

Liu et al., "Meter-long multiblock copolymer microfibers via interfacial bioorthogonal polymerization", Adv Mater., May 6, 2015, 27(17), 15 pages.

Agard et al., "A Strain-Promoted [3+2] Azide-Alkyne Cycloaddition for Covalent Modification of Biomolecules in Living Systems", Journal of American Chemical Society, 2004(126): p. 15046-15047.

Chan et al., "Polytriazoles as Copper(I)-Stabilizing Ligands in Catalysis", Org. Lett., 2004, 6(17): p. 2853-2855.

Curtius et al., "Einwirkung von llydrazin auf m-Cyanbenzoesanre", Prakt. Chem., 1930, 125: p. 40-53.

Hofmann et al., "Einwirkung von Hydrazln auf Dicyandiamid", Ber. Dtsch. Chem. Ges, 1912, 45: p. 2731-2740.

Hopkins, C., "Chimeric molecules employing horseradish peroxidase as reporter enzyme for protein localization in the electron microscope", Methods in Enzymology, 2000, 327: p. 35-45.

Liu et al., "One-Enzyme Triple Catalysis: Employing the Promiscuity of Horseradish Peroxidase for Synthesis and Functionalization of Well-Defined Polymers", ACS Macro Letters, 2018, 7(1): p. 1-6.

Patterson et al., "Crystal structure of recombinant pea cytosolic ascorbate peroxidase." Biochemistry, 1995, 34(13): p. 4331-41.

Pinner, A., "Ueber die Einwirkung von Hydrazin auf Imidoather", Ber. Dtsch. Chem. Ges., 1893, 26: p. 2126-2135.

Rodionov et al., "Ligand-Accelerated Cu-Catalyzed Azide-Alkyne Cycloaddition: A Mechanistic Report", J. Am. Chem. Soc., 2007, 129(42): p. 12705-12712.

Rostovtsev et al., "A Stepwise Huisgen Cycloaddition Process: Copper(I)-Catalyzed Regioselective "Ligation" of Azides and Terminal Alkynes", Angew. Chem., 2002, 114 (14): p. 2708.

Sletten E.M., "Bioorthogonal Chemistry: fishing for selectivity in a sea of functionality", Angewandte Chemie (International Ed. in English), 2009, 48(38): p. 6974-6998.

Tornoe et al., "Peptidotriazoles on solid phase: [1 2,3]-triazoles by regiospecific copper(i)-catalyzed 1,3-dipolar cycloadditions of terminal alkynes to azides", J. Org. Chem., 2002, 67(9): p. 3057-64.

Truong et al., "Red Light Activation of Tetrazine-Norbornene Conjugation for Bioorthogonal Polymer Cross-Linking across Tissue", Chemistry of Materials, 2017, 29(8): p. 3678-3685.

Dunford, B., "Peroxidases and catalases: biochemistry, biophysics, biotechnology and physiology." (2010), p. 183.

Veltch, N.C., "Horseradish peroxidase: a modern view of a classic enzyme", Phytochemistry, 2004, 65(3): p. 249-259.

Fang et al., "Photochemical syntheses, transformations, and bioorthogonal chemistry of trans-cycloheptene and sila trans-cycloheptene Ag(I) complexes", Chemical Science, 2018. 9: p. 1953-1963.

Fukai et al., "Superoxide dismutases: rote in redox signaling, vascular function, and diseases", Antioxidants & Redox Signaling, 2011, 15(6): p. 1583-1606.

Jewett et al., "Rapid Cu-Free Click Chemistry with Readily Synthesized Biarylazacyclooctynones", J. Am. Chem. Soc., 2010, 132(11): p. 3688-3690.

Korshunov et al., "Detection and Quantification of Superoxide Formed within the Periplasm of *Escherichia coli*", Journal of Bacteriology, 2006, 188(17): p. 6326-6334.

Kwon et al., "Direct visualization of a Fe(IV)-OH intermediate in a heme enzyme", Nature Communications, 2016. 7(1): p. 13445.

Lam et al., "Directed evolution of APEX2 for electron microscopy and proteomics", Nature Methods, 2015, 12(1): p. 51-54.

Lambert et al., "Computationally guided discovery of a reactive hydrophilic trans-5-oxocene dienophile for bioorthogonal labeling", Organic and Biomolecular Chemistry, 2017, 15(31): p. 6640-6644.

Martelli et al., "Engineered ascorbate peroxidase as a genetically-encoded reporter for electron microscopy", Nature Biotechnology, 2012, 30(11): p. 1143-1148.

Oliveira et al., "Inverse electron demand Diels-Alder reactions in chemical biology", Chemical Society Reviews, 2017, 46(16): p. 4811-5174.

Rodriguez-Lopez et al., "The Inactivation and Catalytic Pathways of Horseradish Peroxidase with m-Chloroperoxybenzoic Acid", The Journal of Biological Chemistry, 1997, 272(9): p. 5469-5476.

Sletten, C., "From Mechanism to Mouse: A Tale of Two Bioorthogonal Reactions", Acc. Chem. Res., .2011, 44(9): p. 666-676.

Çelik et al. "Engineering the active site of ascorbate peroxidase." European Journal of Biochemistry, 2001, 268(1): p. 78-85.

Urlacher, V., Peroxidases and Catalases: Biochemistry, Biophysics, Biotechnology and Physiology. By H. Brian Dunford. ChemBioChem, 2010. 11(12): p. 1782-1783.

\* cited by examiner

A *Interfacial polymerization* produces dihydrotetrazine containing fibers that can be activated for bioorthogonal chemistry

B

SEQUENCE LISTING

<160> NUMBER OF SEQ ID NOS: 1

<210> SEQ ID NO 1
<211> LENGTH: 250
<212> TYPE: PRT
<213> ORGANISM: Artificial Sequence
<220> FEATURE:
<223> OTHER INFORMATION: APEX2; an engineered variant of ascorbate

```
                                  peroxidase
<300> PUBLICATION INFORMATION:
<308> DATABASE ACCESSION NUMBER: PDB/5L86
<309> DATABASE ENTRY DATE: 2016-06-07
<313> RELEVANT RESIDUES IN SEQ ID NO: (1)..(249)

<400> SEQUENCE: 1

Met Gly Lys Ser Tyr Pro Thr Val Ser Ala Asp Tyr Gln Asp Ala Val
1               5                   10                  15

Glu Lys Ala Lys Lys Lys Leu Arg Gly Phe Ile Ala Glu Lys Arg Cys
            20                  25                  30

Ala Pro Leu Met Leu Arg Leu Ala Phe His Ser Ala Gly Thr Phe Asp
                35                  40                  45

Lys Gly Thr Lys Thr Gly Gly Pro Phe Gly Thr Ile Lys His Pro Ala
    50                  55                  60

Glu Leu Ala His Ser Ala Asn Asn Gly Leu Asp Ile Ala Val Arg Leu
65                  70                  75                  80

Leu Glu Pro Leu Lys Ala Glu Phe Pro Ile Leu Ser Tyr Ala Asp Phe
                85                  90                  95

Tyr Gln Leu Ala Gly Val Val Ala Val Glu Val Thr Gly Gly Pro Lys
            100                 105                 110

Val Pro Phe His Pro Gly Arg Glu Asp Lys Pro Glu Pro Pro Pro Glu
            115                 120                 125

Gly Arg Leu Pro Asp Pro Thr Lys Gly Ser Asp His Leu Arg Asp Val
        130                 135                 140

Phe Gly Lys Ala Met Gly Leu Thr Asp Gln Asp Ile Val Ala Leu Ser
145                 150                 155                 160

Gly Gly His Thr Ile Gly Ala Ala His Lys Glu Arg Ser Gly Phe Glu
                165                 170                 175

Gly Pro Trp Thr Ser Asn Pro Leu Ile Phe Asp Asn Ser Tyr Phe Thr
            180                 185                 190

Glu Leu Leu Ser Gly Glu Lys Glu Gly Leu Leu Gln Leu Pro Ser Asp
        195                 200                 205

Lys Ala Leu Leu Ser Asp Pro Val Phe Arg Pro Leu Val Asp Lys Tyr
    210                 215                 220

Ala Ala Asp Glu Asp Ala Phe Phe Ala Asp Tyr Ala Glu Ala His Gln
225                 230                 235                 240

Lys Leu Ser Glu Leu Gly Phe Ala Asp Ala
            245                 250
```

METHODS FOR INDUCING BIOORTHOGONAL REACTIVITY

This application is a continuation-in-part of U.S. patent application Ser. No. 16/062,423, filed Jun. 14, 2018, now U.S. Pat. No. 10,875,840, issued Dec. 29, 2020, which claims priority benefit of a national stage application under 35 U.S.C. 371 of International Application No. PCT/US2016/066793, titled "Methods For Inducing Bioorthogonal Reactivity," filed Dec. 15, 2016, which claims priority to U.S. Provisional Patent Application No. 62/267,450, filed Dec. 15, 2015, the disclosures of each of these applications being incorporated herein by reference in their entireties for all purposes.

STATEMENT REGARDING FEDERALLY SPONSORED RESEARCH

This invention was made with government support under NSF Grant Nos. CHE-0840401 and CHE-1229234 awarded by National Science Foundation and NIH Grant Nos. GM132460, P20GM104316, P30GM110758, S10RR026962, and 5100D016267 awarded by National Institutes of Health. The government has certain rights in the invention.

REFERENCE TO SEQUENCE LISTING

The Sequence Listing for this application is labeled "UOD-522US_SubstituteSequenceListing.txt", which was created on Feb. 3, 2021 and is 2,850 bytes in size. The contents of the Sequence Listing are incorporated herein by reference in their entireties.

BACKGROUND OF THE INVENTION

Bioorthogonal chemistry has evolved into a field with broad-reaching applications in biology, medicine and materials science. Driving the field has been the vigorous development of unnatural transformations that proceed selectively in the presence of Nature's functional groups. Recently, bioorthogonal chemistry has been utilized in payload release strategies, with the aim of triggering diverse events including drug delivery, gene expression, and modulating materials properties. There has also been a growing interest in using external stimuli to induce bioorthogonal reactivity. In particular, photoinducible reactions have emerged as a method for turning on bioorthogonal reactions with temporal and spatial control. Key advances include tetrazole and cyclopropenone based ligations, where photolysis produces reactive nitrile imines and cyclooctyne derivatives, respectively. Such 'photoclick' reactions generally utilize short-wavelength light to unleash more reactive species. The direct use of red or near IR light to induce bioorthogonal reactivity has not been described. Lin has recently described two-photon based photoinducible tetrazole reactions that utilize near IR light, and Popik has shown that cyclopropenones can be photodecarbonylated by a two photon process. While two-photon methods provide high spatial resolution, their very small focal volumes currently limit many practical applications. Recently, near-IR photodecaging strategies have been described based on cyanine, BODIPY, and phthalocyanine dyes. A current challenge for red- and near-IR photodecaging strategies lies is the need to improve the kinetics of photorelease.

SUMMARY OF THE INVENTION

The invention provides a method for catalytically converting a dihydrotetrazine 1 into a tetrazine 2, wherein the dihydrotetrazine 1 comprises a first R group and a second R group, wherein the first R group is a substituted or unsubstituted aryl, heteroaryl, alkyl, alkenyl, alkynyl, carbonyl, or heteroatom-containing group, and the second R group is selected from the group consisting of H and substituted or unsubstituted aryl, heteroaryl, alkyl, alkenyl, alkynyl, carbonyl, and heteroatom-containing groups;

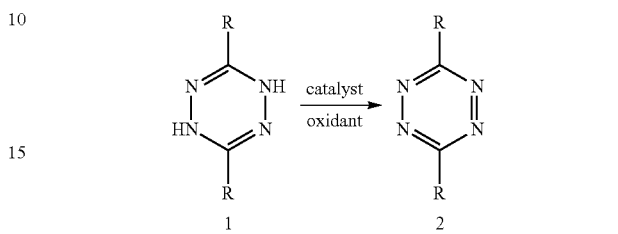

wherein the method comprises (a) providing the dihydrotetrazine 1 in a reaction medium, and (b) adding an enzyme as a catalyst and an oxidant to the reaction medium, whereby the dihydrotetrazine 1 is converted to the tetrazine 2.

In an embodiment, the enzyme is a horseradish peroxidase (HRP) or an ascorbate peroxidase.

In an aspect, the ascorbate peroxidase is APEX2 (SEQ ID NO:1), an engineered variant of ascorbate peroxidase. In another embodiment, the ascorbate peroxidase has a substantially identical sequence as that of APEX2 (SEQ ID NO:1). The sequence listing of APEX2 (SEQ ID NO:1) is provided herein in Table 5 and can also be retrieved from, e.g., Protein Data Bank (ID number PDB:5L86).

In another aspect, the ascorbate peroxidase is a mutated APEX2. The mutated APEX2 may comprise one or more mutations selected from the group consisting of F41A, A19V, D222G and a combination thereof. In an embodiment, the ascorbate peroxidase has a substantially identical sequence as that of mutated APEX2.

As used herein, the phrase "substantially identical" refers to two or more sequences having at least 50%, 60%, 70%, 80%, 90%, 95%, or 99%, and in some aspects 90-95% nucleotide identity or amino acid residue identity. There may be substantial identity over a region of at least about 100 residues, or at least about 150-200 residues. In some embodiments, such sequences may be substantially identical over the entire coding region.

In addition, a "substantially identical" amino acid sequence may be a sequence that differs from a reference sequence by one or more conservative or non-conservative amino acid substitutions, deletions or insertions, particularly where the substitution is not the active site of the molecule. When it occurs at the site, provided that the polypeptide retains at least 50%, 60%, 70%, 80%, 90%, 95%, or 99% of the original functional properties or activities. A conservative amino acid substitution, for example, substitutes one amino acid for another amino acid of the same class (e.g., substitution of a hydrophobic amino acid such as isoleucine, valine, leucine or methionine for one other hydrophobic amino acid, Or substitution of one polar amino acid for another polar amino acid, such as substitution of arginine for lysine, substitution of glutamic acid for aspartic acid or substitution of glutamine for asparagine). One or more amino acids can be deleted from, for example, an ascorbate peroxidase, resulting in alteration of the structure of the polypeptide without significantly altering its oxidative/biological activity. The modified polypeptide sequences of the present invention can be assayed for ascorbate peroxidase oxidative/biological activity by several methods known in the art.

In an embodiment, the ascorbate peroxidase may comprise an amino acid sequence at least 50%, 60%, 70%, 80%, 90%, or 95% identical to the amino acid sequence of APEX2 (SEQ ID NO:1). In another embodiment, the ascorbate peroxidase may consist of an amino acid sequence at least 50%, 60%, 70%, 80%, 90%, or 95% identical to the amino acid sequence of mutated APEX2. The mutated APEX2 may comprise one or more mutations selected from the group consisting of F41A, A19V, D222G and a combination thereof.

In an embodiment, the dihydrotetrazine 1 is converted to the tetrazine 2 in the presence of superoxide dismutase (SOD).

In one embodiment, the oxidant is $O_2$, optionally atmospheric $O_2$, or atmospherically-derived dissolved $O_2$ in media. In another embodiment, the $O_2$ is at a lower partial pressure than that found under atmospheric conditions. In yet another embodiment, the $O_2$ is at a higher partial pressure than that found under atmospheric conditions.

In an aspect, the method is carried out in a biological milieu selected from the group consisting of living cells and tissues, cell media, blood, serum, and cell lysates.

In an embodiment, at least one of the first R group and the second R group contains an aryl vinyl ether, and the method further comprises releasing an aryl alcohol from the aryl vinyl ether.

In an aspect, the method further comprises trapping the tetrazine with a dienophile. In an embodiment, the method further comprises:

(i) uniting one or more bimolecular entities selected from the group consisting of proteins, DNA, and RNA;

(ii) attaching a fluorescent molecule or a fluorescent protein to another small molecule or a biomolecule; or (iii) attaching a molecule to the surface of a fiber or a glass slide.

The invention also provides compounds according to the following structures, useful in performing the methods described herein or resulting from performing those method:

In an aspect, the dihydrotetrazine 1 has the following structure:

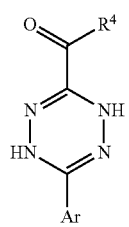

wherein $R^4$ is selected from the group consisting of H, aryl, heteroaryl, alkyl, alkenyl, alkynyl, and heteroatom-containing groups, and Ar is an aromatic or heteroaromatic group.

In an embodiment, the dihydrotetrazine 1 has one of the following structures:

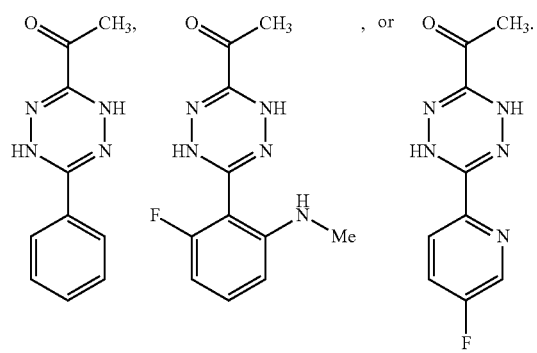

In another embodiment, the dihydrotetrazine 1 is conjugated to a compound having the following structure:

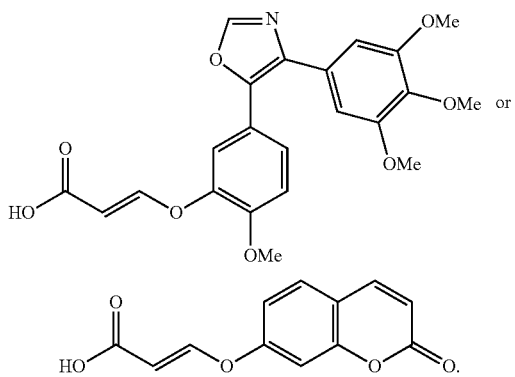

In an aspect, the dihydrotetrazine 1 has one of the following structures:

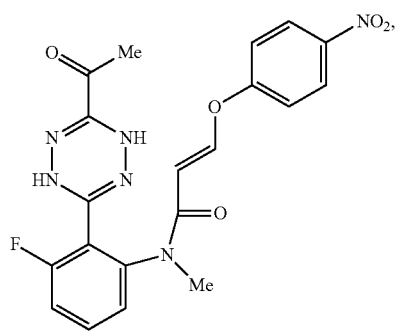

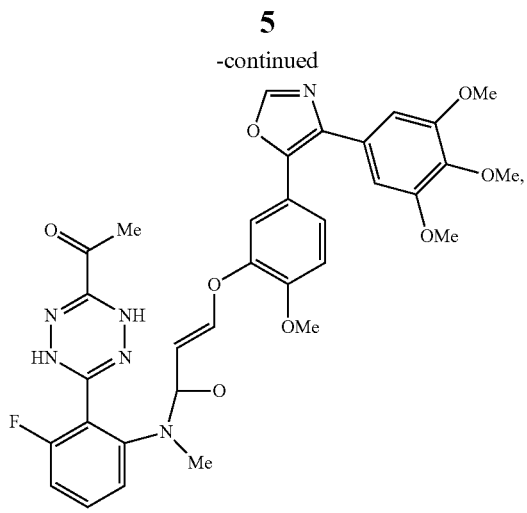
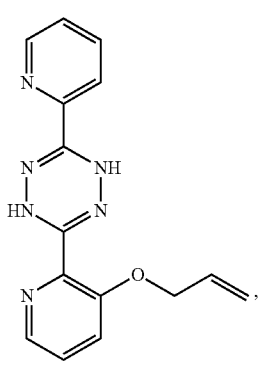
In an embodiment, the dihydrotetrazine 1 has one of the following structures:
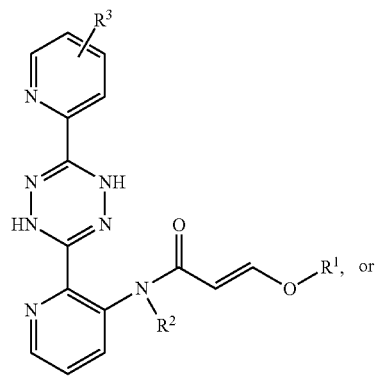
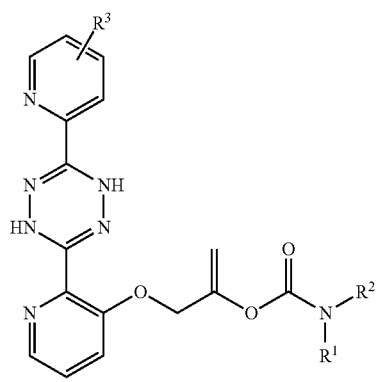
wherein $R^1$, $R^2$ and $R^3$ are each individually selected from the group consisting of H, aryl, heteroaryl, alkyl, alkenyl, alkynyl, carbonyl, and heteroatom-containing groups.
In another embodiment, the dihydrotetrazine 1 has one of the following structures:
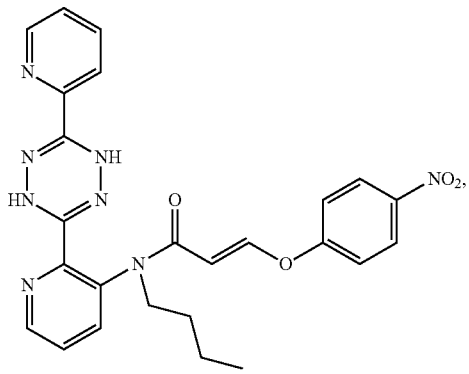

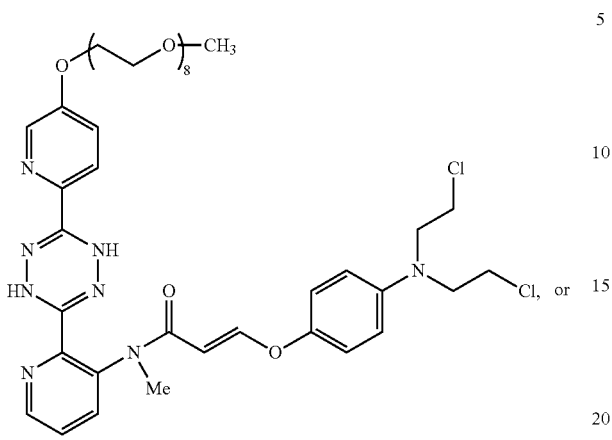

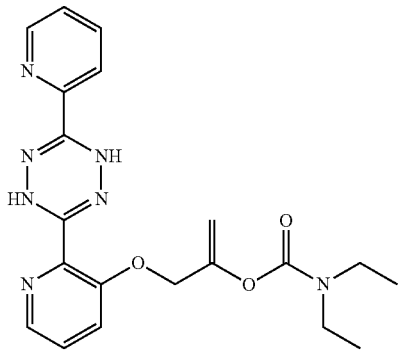

wherein $R^1$, $R^2$ and $R^3$ are each individually selected from the group consisting of H, aryl, heteroaryl, alkyl, alkenyl, alkynyl, carbonyl, and heteroatom-containing groups.

In an aspect, the tetrazine 2 has the following structure:

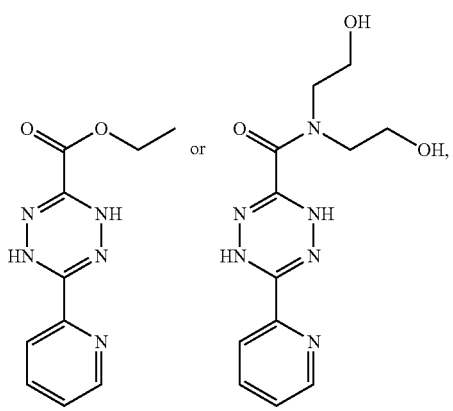 [SMILES: CCOC(=O)C1=NNC(c2ccccn2)=NN1 ; "or" ; O=C(C1=NNC(c2ccccn2)=NN1)N(CCO)CCO]

and
the tetrazine 2 has the following structure:

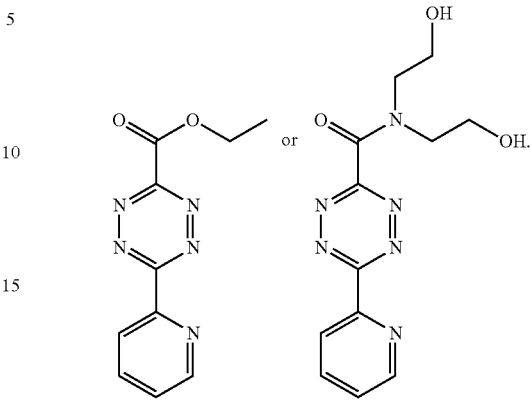

Figure 12:
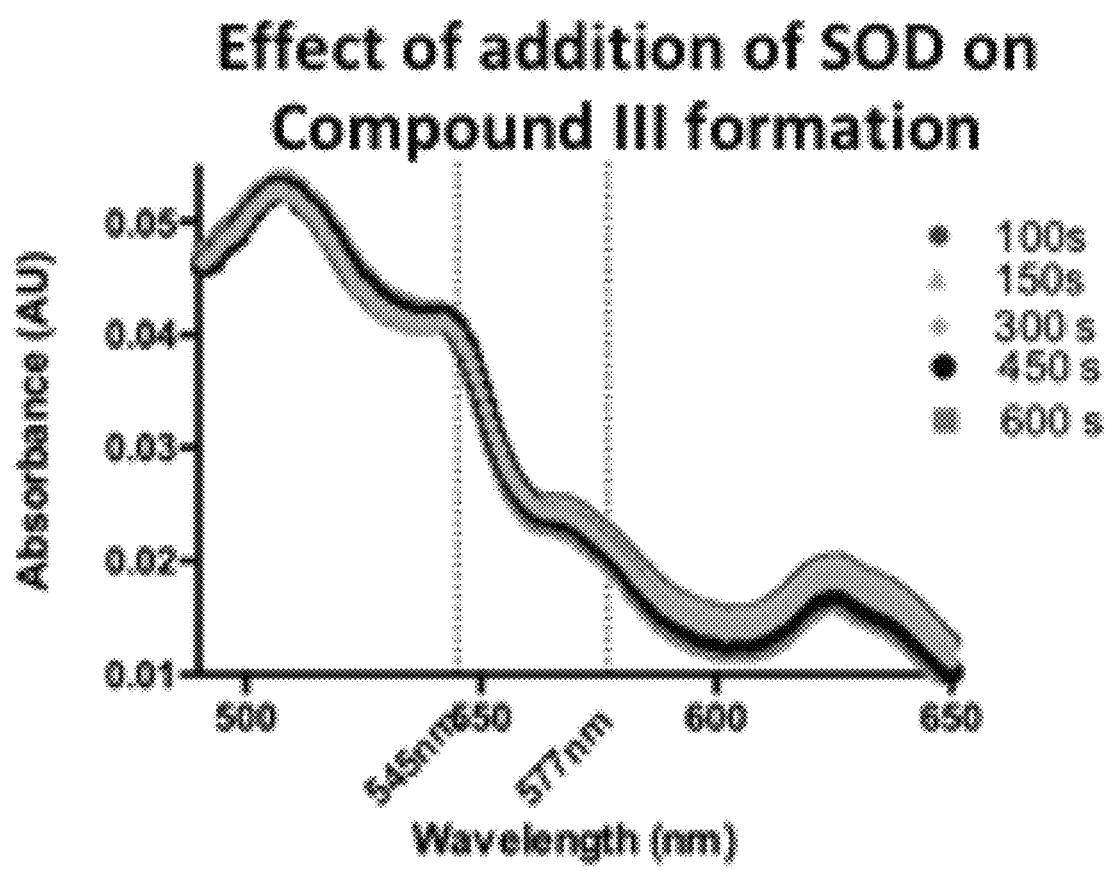

FIG. 12 shows Absorption spectrum during oxidation of 50 µM 16, 2.75 µM APEX2 (SEQ ID NO:1), and 50 µM SOD in PBS with EDTA. No apparent compound III formation when SOD added as there is no increase in absorbance at $\lambda_{max}$=545 nm and 577 nm.

Figure 13:
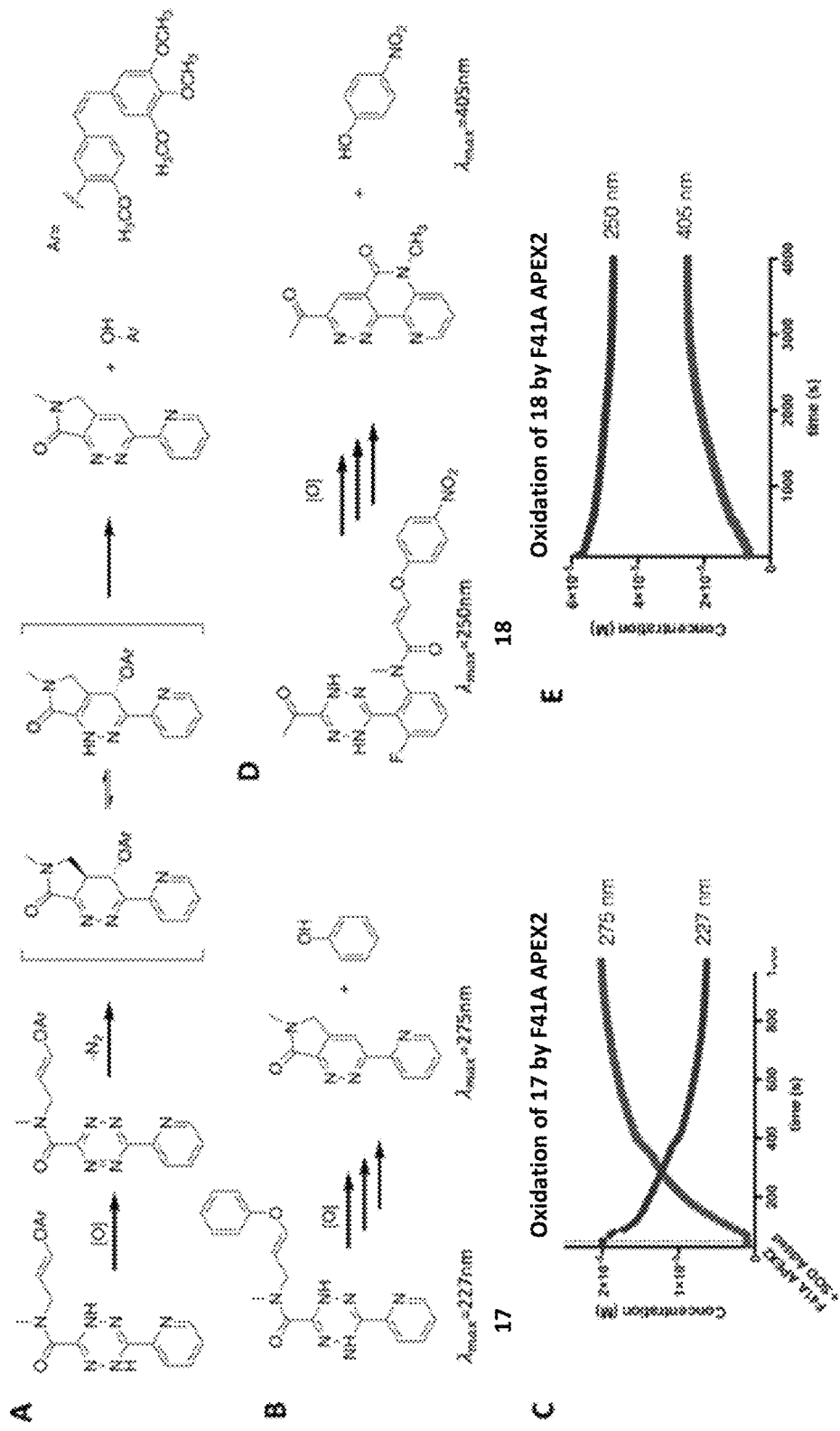

FIG. 13 shows DHT Prodrug Scaffolds A. Oxidation of DHT Prodrug, Ar=CA4 as cytotoxic drug. B. DHT Prodrug model 17(3) and released products. C. Oxidation of 3 by 275 nM F41A APEX2 in the presence of 1 µM SOD in PBS with EDTA where phenol mimics cytotoxic drug. D. DHT prodrug model 18(4). E. Oxidation of 18 by 275 nM F41A APEX2 in the presence of 1 µM SOD in PBS with EDTA where nitrophenol mimics cytotoxic drug.

Figure 14:
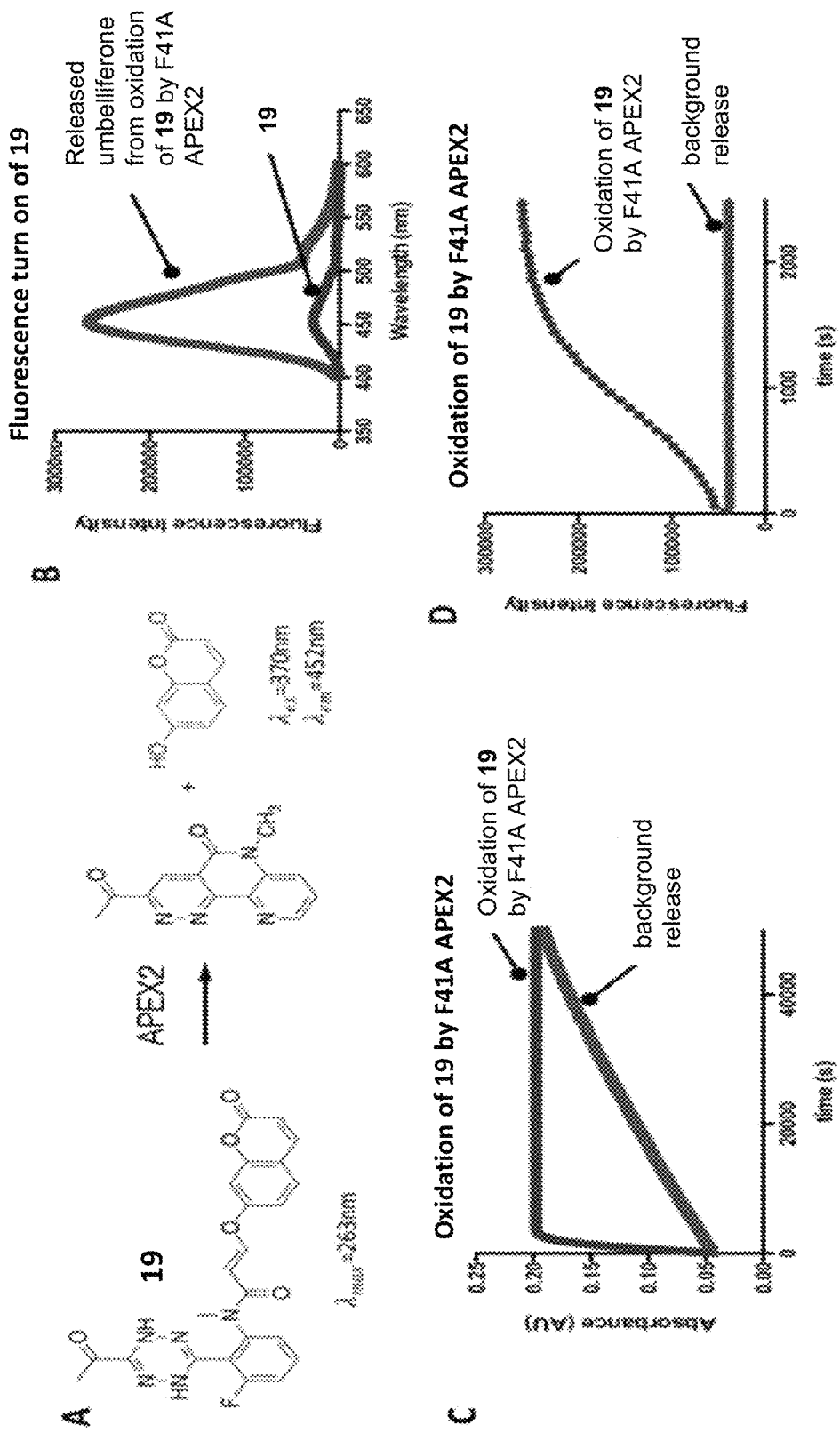

FIG. 14 shows: A. Oxidation of fluorogenic DHT releases free umbelliferone for increased fluorescence emission. B. Fluorescence emission spectrum of 19(5) and released umbelliferone from oxidation of 19 by F41A APEX2. C. UV-Vis spectrum of oxidation of 19 by 275 nM F41A APEX2 in the presence of 1 µM SOD in PBS with EDTA and background release of 19 in PBS with EDTA. Monitoring at 370 nm. D. Fluorescence spectrum of oxidation of 19 by 275 nM F41A APEX2 in the presence of 1 µM SOD in PBS with EDTA and background release of 19 in PBS with EDTA.

Figure 15:
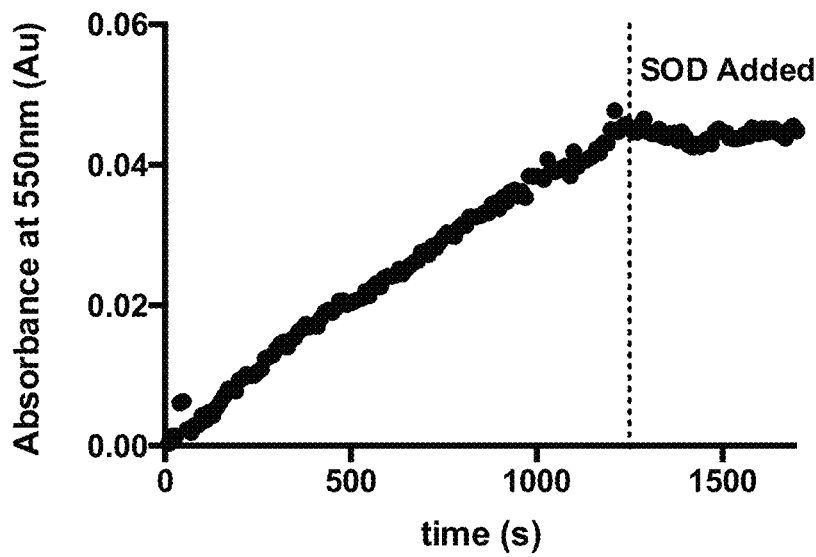

FIG. 15 shows reduction of Cytochrome C followed at 550 nm.

Figure 16:
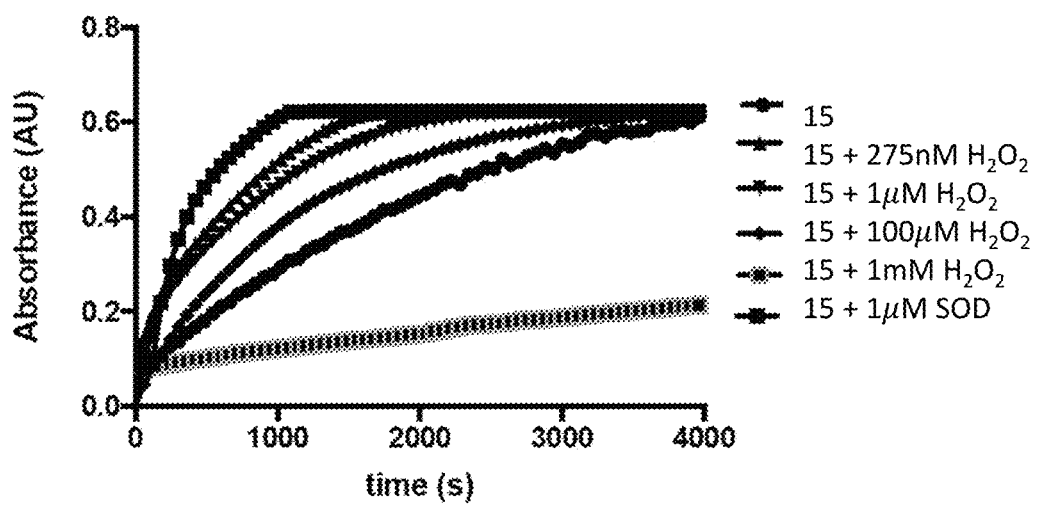

FIG. 16 shows effect of $H_2O_2$ on rate of oxidation of 15 by F41A APEX2.

Figure 17:
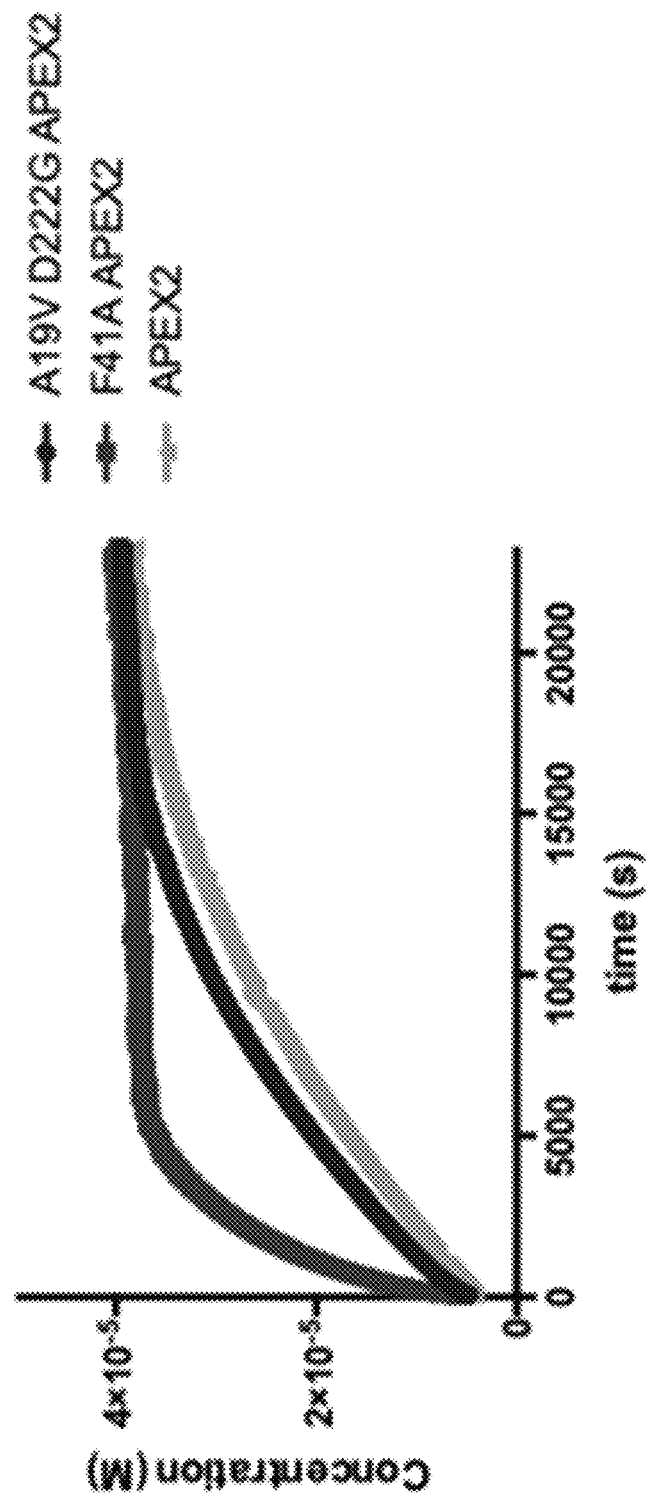

FIG. 17 shows oxidation of 15 by APEX2 and APEX2 variants: F41A APEX2 and A19V D222G APEX2 followed by monitoring of tetrazine formation at 325 nm by UV-Vis spectrometry.

DETAILED DESCRIPTION OF THE INVENTION

Rapid bioorthogonal reactivity can be induced by controllable, catalytic stimuli using air as the oxidant. Methylene blue (4 µM) irradiated with red light (660 nm) catalyzes the rapid oxidation of a dihydrotetrazine ("DHTz") to a tetrazine ("Tz"), thereby turning on reactivity toward trans-cyclooctene dienophiles. Alternately, the aerial oxidation of dihydrotetrazines can be efficiently catalyzed by nanomolar levels of horseradish peroxidase under peroxide-free conditions. Selection of dihydrotetrazine/tetrazine pairs of sufficient kinetic stability in aerobic aqueous solutions is key to the success of these approaches. In this work, polymer fibers carrying dihydrotetrazines were catalytically activated and covalently modified by trans-cyclooctene conjugates of small molecules, peptides and proteins. In addition to visualization with fluorophores, fibers conjugated to a cell adhesive peptide exhibited a dramatically increased ability to mediate contact guidance of cells.

Figure 1:
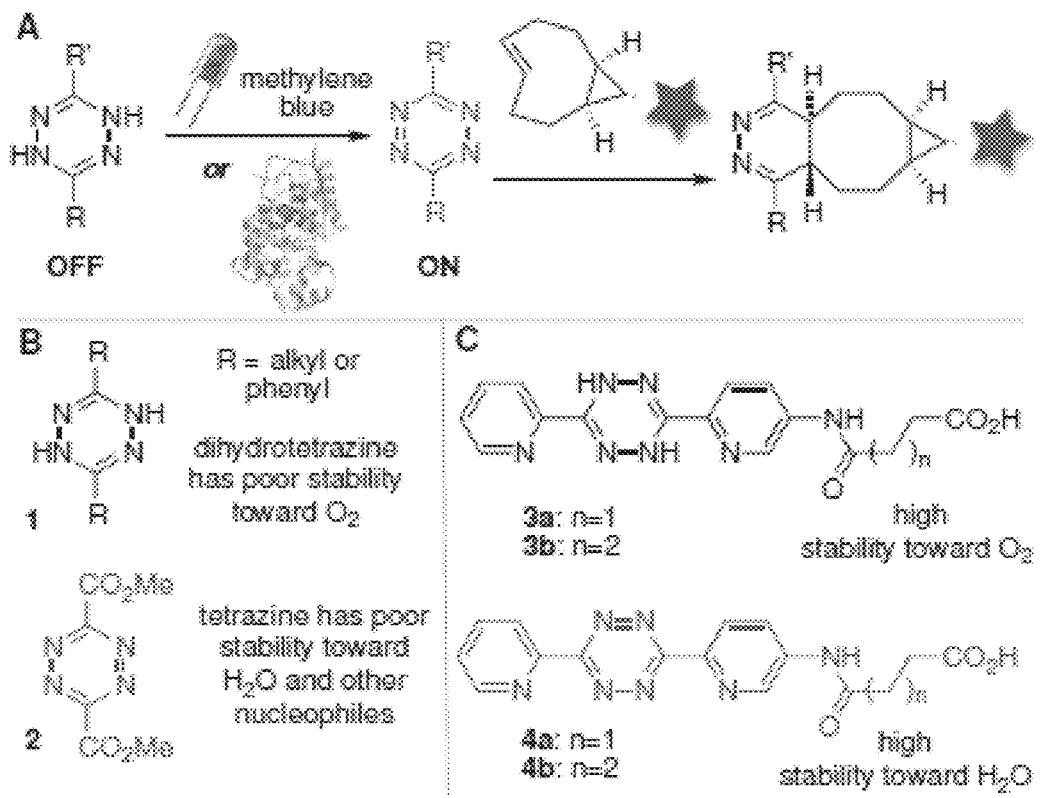
FIG. 1 shows dihydrotetrazine/tetrazine pairs according to the invention.

Described herein are the first examples of catalytic turn-on of the tetrazine ligation, where rapid bioorthogonal reactivity can be induced by a controllable, catalytic stimulus (FIG. 1, panel A). Inverse electron demand Diels-Alder adduction of a conformationally strained trans-cycloalkene (the star represents an arbitrary functional group) with the tetrazine occurs with an extremely high reaction rate. Either visible light and a photosensitizer, or very low loadings of horseradish peroxidase can be used to catalyze the oxidation of a dihydrotetrazine to a tetrazine.

Dienophiles other than trans-cycloalkenes can be used as well. For example, in some embodiments the invention provides compositions and methods in which a muted drug (e.g., a nitrogen mustard or doxorubicin) can be delivered locally to a tumor. See Scheme 1. Here an antibody-catalyst construct (either a photocatalyst, HRP catalyst, or synthetic Fe-porphyrin catalyst) can be retargeted to a tumor, and with a later injection of the prodrug could be used to trigger the oxidation reaction locally in vivo. The inventors have demonstrated that this conjugation/release works and is faster than can be observed by NMR.

Scheme 1

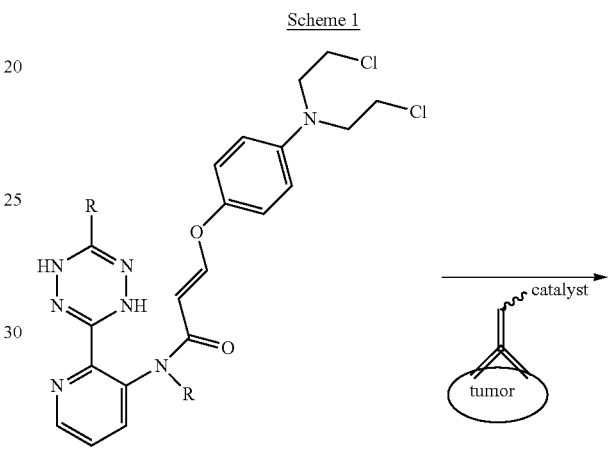

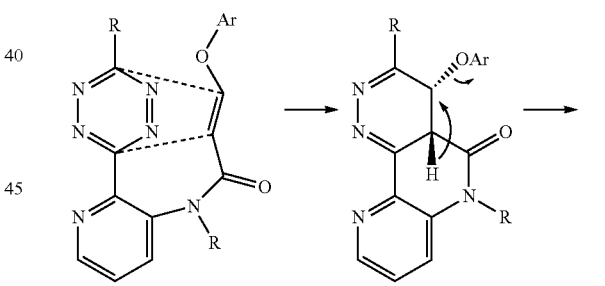

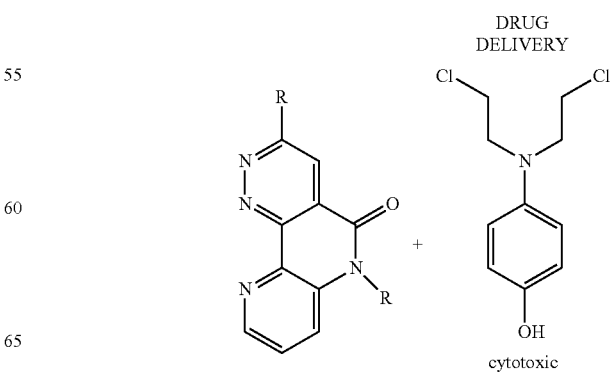

DRUG DELIVERY cytotoxic

-continued

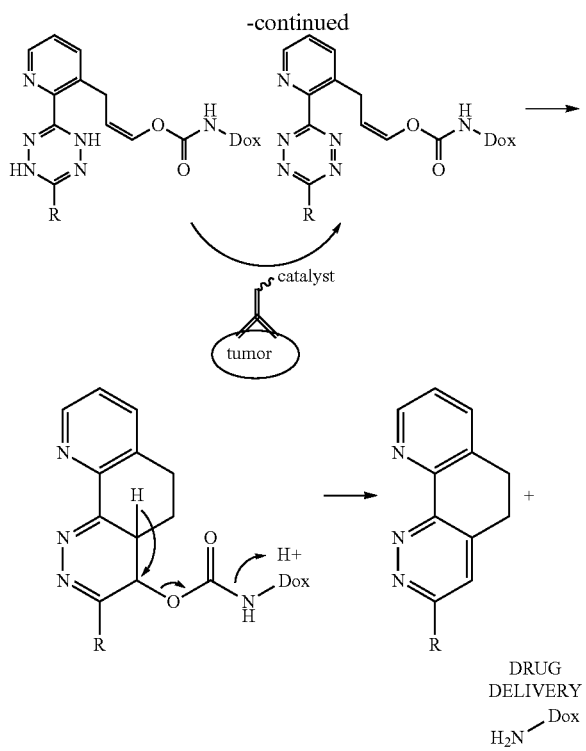

A challenge to the development of catalytic methods for turning on the tetrazine ligation was the identification of a DHTz/Tz pair that would be stable in both oxidation states (FIG. 1, panel B). For most redox couples, either the DHTz is too readily oxidized in air (e.g., 1), or the Tz is too reactive toward water and other nucleophiles (e.g., 2). The inventors show here that the dipyridyl DHTz/Tz pair (3/4) has good stability in both states (FIG. 1, panel C). Dihydrotetrazines 3 are highly resistant toward background oxidation in organic solvents, and a number of derivatives have been synthesized and shown stable even to silica gel chromatography. In ambient light, a 35 µM solution of 3a in MeOH was shown to retain 99 and 98% of the DHTz oxidation state after 1 and 2 hours, respectively. Aqueous solutions of 3a were handled in glassware that had been first rinsed with 2.0 mM EDTA in PBS to remove adventitious metal impurities. After standing in the dark at 25° C. in PBS buffer, a solution of 3a was monitored by UV-vis and shown to retain 99 and 96% of the DHTz oxidation state over 30 min and 2.5 hours respectively. In ambient light at 25° C. in PBS buffer, a solution of 3a was shown to retain 97 and 94% of the DHTz oxidation state after 1 and 2 hours, respectively. In PBS containing 10% mouse serum, 90% of 3a was retained in the DHTz oxidation state after 1 h. Analogs of tetrazines 4 have been described previously and used broadly for applications in nuclear medicine and cell imaging. In PBS buffer at 25° C., tetrazine 4a (800 µM) shows 98% and 83% fidelity after 2 h and 24 h, respectively. The stability of a radiolabeled derivative of tetrazine 4b has been studied by Robillard at 37° C. in PBS, serum and blood, with 97%, 87% and 59% retention of the tetrazine observed after 2 hours.

Figure 2:
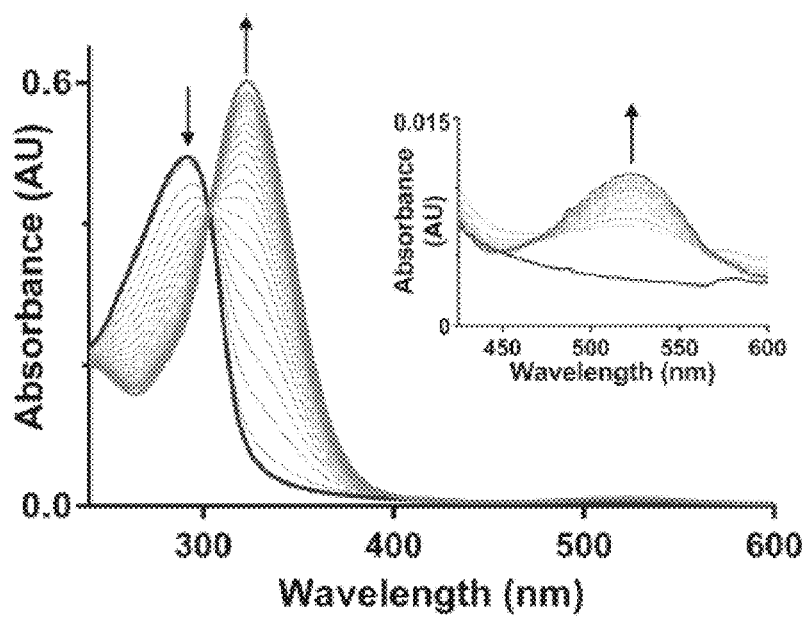
FIG. 2 shows UV-vis spectra of several compounds used in the practice of the invention.

Compound 3a has a maximum in the UV-vis spectrum at 292 nm, and 4a has a maximum at 325 nm with a less intense peak at 525 nm (FIG. 2). As a reference for their catalytic studies, the inventors first monitored the electrochemical oxidation of 3a in phosphate buffer, for which the voltammogram displays a single peak centered at 0.02 V. Under mildly oxidizing conditions (0.18 V relative to Ag/AgCl), a 1.1 mM solution of 3a turns pink and the oxidation to 4a proceeds cleanly with an isosbestic point at 303 nm. This isosbestic point was also conserved in the photocatalytic and enzymatic (FIG. 2) oxidations of 3a described below, and the spectroscopic changes at 292 and 325 nm were routinely used for monitoring reaction progress.

Figure 3:
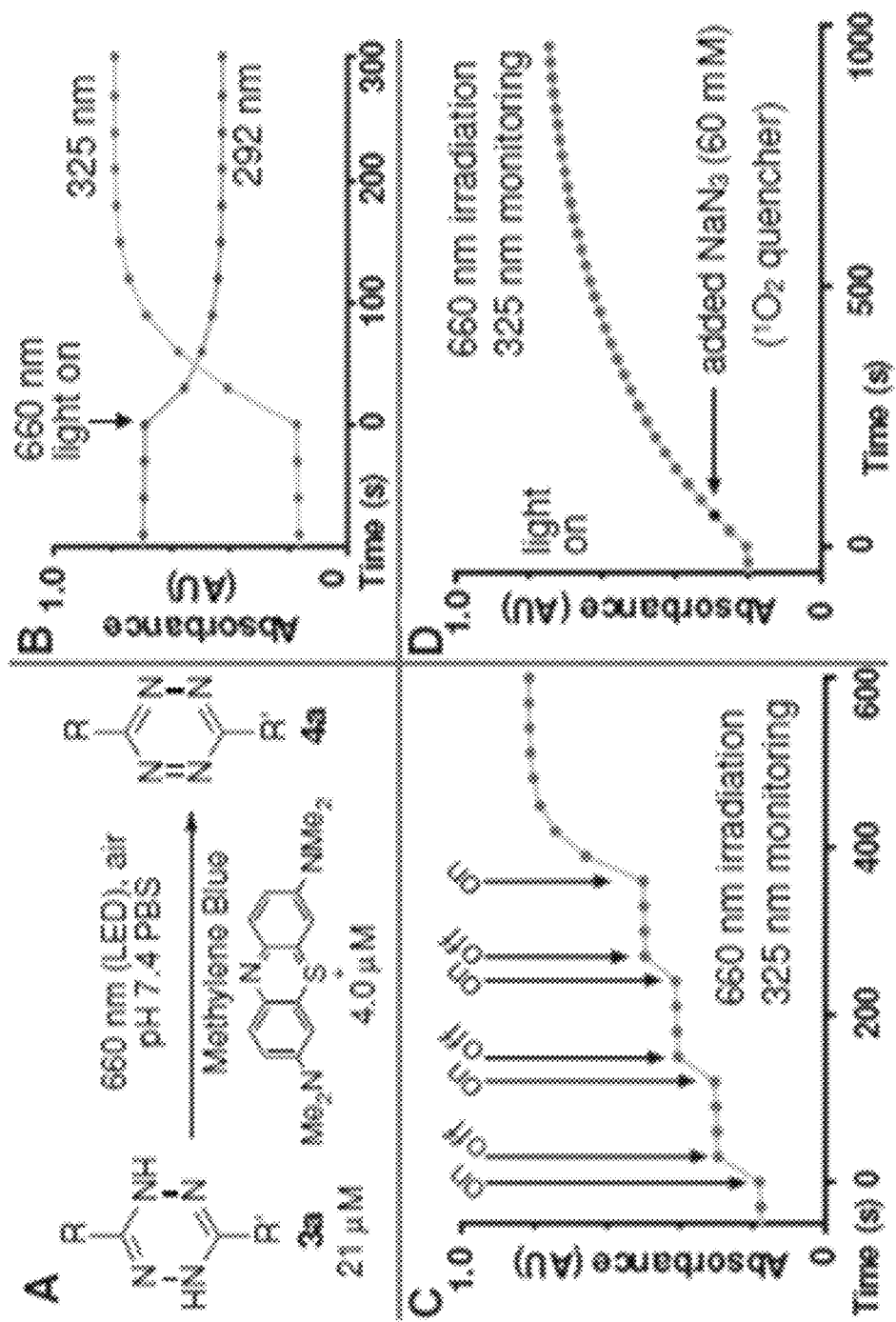
FIG. 3 shows the progress of photooxidation of a tetrahydrotetrazine to a tetrazine according to the invention.

Upon addition of horseradish peroxidase (15 nM) the UV-vis spectrum was monitored every 10 seconds. With 50% conversion after 100 seconds, complete conversion of 3a to 4a is observed after 600 seconds, as evidenced by the decrease in the absorption at 292 nm and increase at 325 nm with an isosbestic point at 303 nm. Similar spectral changes are observed when 3a is electrochemically oxidized to 4a in aqueous solution, or when the oxidation of 3a to 4a is photocatalyzed by methylene blue. The inventors have found that a number of photosensitizers in the presence of long wavelength visible light were found to catalyze the oxidation of 3a to 4a in the presence of air. Methylene blue was considered a particularly attractive sensitizer due to its clinical relevance, low molecular weight, low toxicity, high solubility, and an absorption spectrum ($\lambda$max 665 nm) that extends to the near IR. Further, methylene blue has previously been explored for applications in photodynamic therapy based on oxidation of indole-3-acetic acid. Rose bengal ($\lambda$max 550 nm), used in a range of biomedical applications, was also identified as an excellent sensitizer. Other successful sensitizers (irradiation wavelength) include acridine orange (528 nm), coomassie brilliant blue (528 nm), rhodamine B (590 nm), BODIPY (475 nm), safranin (528 nm), phenol red (528 nm), carboxylfluorescein (528 nm), and SiR Silarhodamine (purchased from Spirochrome. Experiments to study the catalytic photooxidation were conducted at 25° C. in a thermostatted cuvette with stirring capability and a single top-mounted LED. A custom 3D printed light fixture was used to mount the LED directly above the cuvette and block ambient light. As shown in FIG. 3, panel B, irradiation of 3a (21 µM) with a 660 nm LED (9.1 mW/cm$^2$) in the presence of methylene blue (4 µM) in pH 7.4 PBS caused conversion to tetrazine 4a with quantitative yield within 200 seconds. Methylene blue (4 µM) also catalyzed the conversion of 3a to 4a in the presence of ambient light, with 47% conversion noted after 2 h. The light dependence of the methylene blue catalyzed oxidation was demonstrated by turning the LED on and off (FIG. 3, panel C). Similar light dependent on/off behavior was exhibited with either rose bengal or carboxyfluorescein with irradiation centered at 528 nm (2.3 mW/cm$^2$. Both methylene blue and rose bengal are known $^1O_2$ sensitizers, and the inventors therefore queried the influence of a $^1O_2$ quencher on the oxidation rate of 3a. Neither the methylene blue (FIG. 3, panel D) nor the rose bengal catalyzed photooxidations are impeded by the addition of 60 mM NaN$_3$. By contrast, the rate of the reaction between 2,5-diphenylisofuran with $^1O_2$ was greatly reduced when 23 mM NaN$_3$ was added. These experiments strongly imply that $^1O_2$ is not the oxidant of 3a under photocatalytic conditions. The mechanism of photooxidation more likely involves electron transfer and is the subject of ongoing study.

As a model of hypoxia, the inventors also demonstrated catalytic oxidation of 3a to 4a in solutions that were depleted in oxygen. Thus, a PBS solution of 3a was sparged with 98% nitrogen and 2% air, such that the final O$_2$ concentration was 5 µM. Addition of methylene blue (7 µM) and irradiation at 660 nm with monitoring by UV-vis indicated that conversion of 3a to 4a was complete within 30 minutes.

Figure 4:
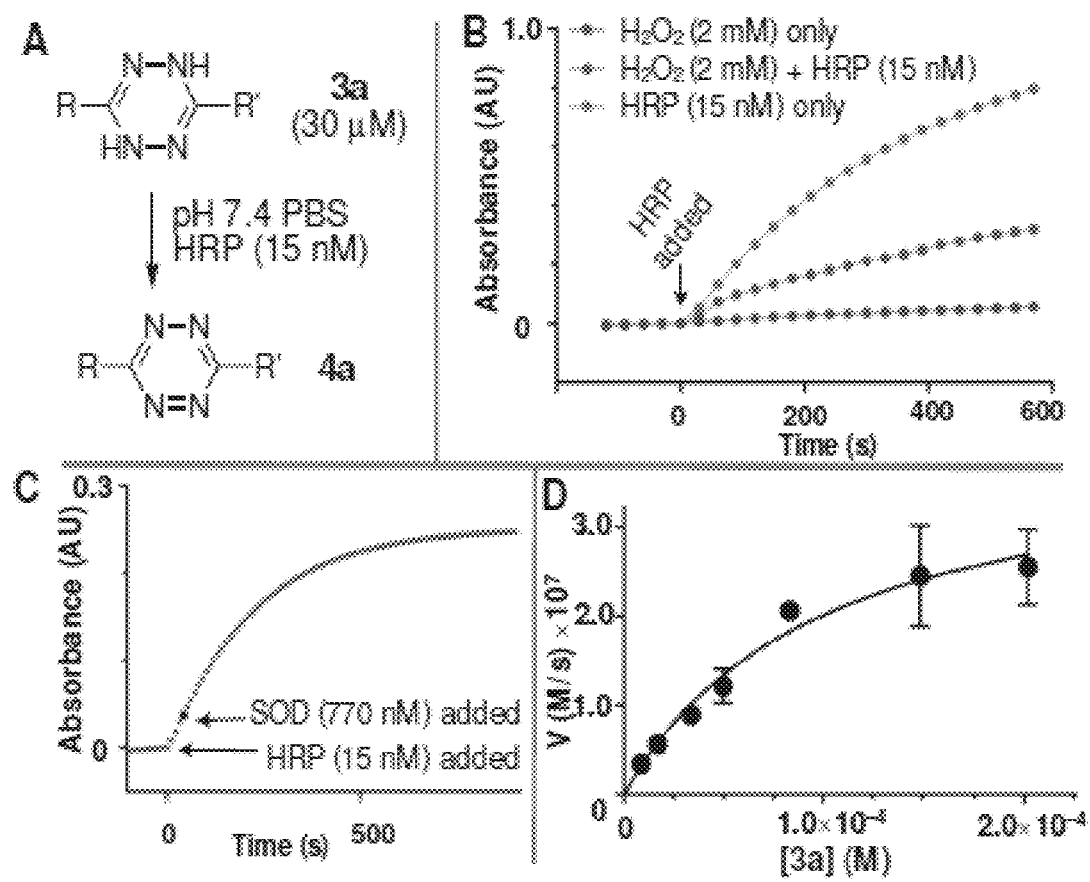
FIG. 4 shows the progress of horseradish peroxidase catalyzed oxidation of a tetrahydrotetrazine to a tetrazine according to the invention.

As a complement to these photocatalyzed reactions, the inventors observed that HRP can efficiently catalyze the oxidation of 3a in the dark at low enzyme concentration (15 nM) (FIG. 4). While HRP typically requires $H_2O_2$ as the terminal oxidant, the addition of HRP to a peroxide-free solution of 3a (30 μM) in PBS led to the rapid formation of 4a (FIG. 4, panel B). The rate of formation of 4a was significantly slower in the presence of 2 mM $H_2O_2$, and was near baseline in the presence of $H_2O_2$ but absence of HRP. Neither cytochrome c nor hemoglobin were effective catalysts of DHTz oxidation, with only slow conversion of 3a to 4a even with heme concentrations that were nearly 3 orders of magnitude higher than that used with HRP. As shown in FIG. 4, panel C, the addition of superoxide dismutase (SOD, 770 nM) in PBS does not suppress the rate of the oxidation of 3a by HRP, providing evidence that superoxide is not responsible for the oxidation. Finally, it was observed that the oxidation of 3a by HRP in PBS containing EDTA (2.0 mM) follows Michaelis-Menten kinetics, with $K_m = 1.0 \times 10^{-4}$ M, $k_{cat} = 27$ s$^{-1}$, and $k_{cat}/K_m = 2.7 \times 10^5$ M$^{-1}$s$^{-1}$ (FIG. 4, panel D).

The light and enzyme-catalyzed reactions developed here enable the functionalization of polymeric materials with potential biomedical applications. The inventors previously disclosed [Adv Mater, 2015, 27, 2783-90] the production of peptide-containing polymer fibers through interfacial bioorthogonal polymerization based on tetrazine ligation using bis-tetrazine and bis-TCO monomers dissolved in immiscible solvents. These hydrogel-like polymer fibers, with diameters ranging from 6 to 11 μm when dry, are cytocompatible, biologically active and mechanically robust; they resemble many fibrous structures found in the human body and can be woven into complex, higher order assemblies for tissue engineering purposes. However, the use of interfacial polymerization to fabricate protein-containing polymer fibers is not trivial due to the possibility of protein denaturation by the required organic solvent.

Figure 5:
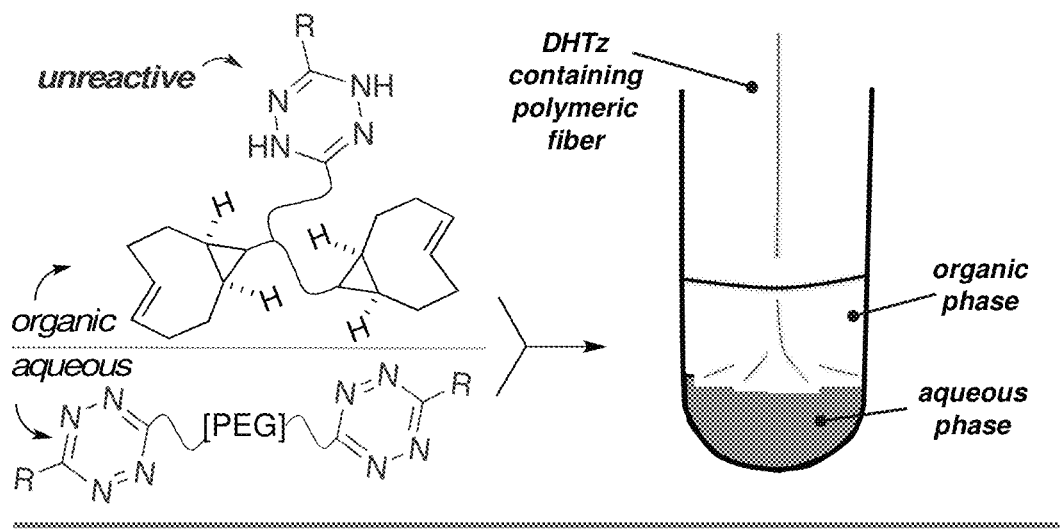
FIG. 5 is a schematic representation of interfacial polymerization involving a dihydrotetrazine-derived monomer according to the invention.
Figure 5:
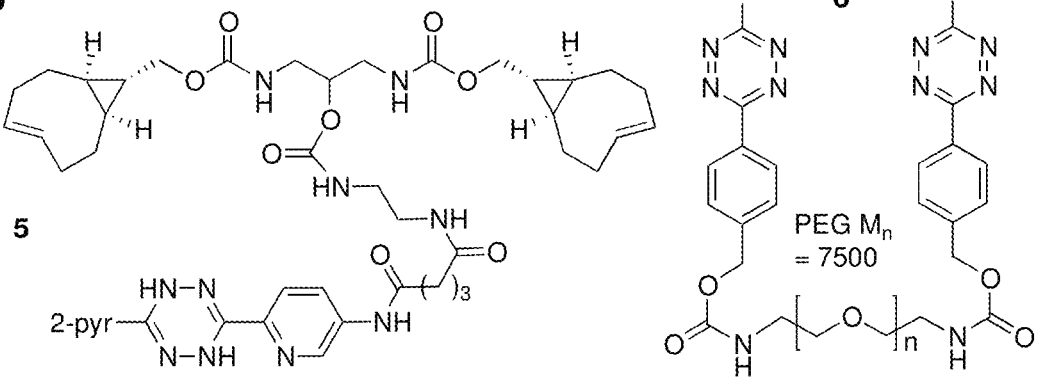
Figure 5:
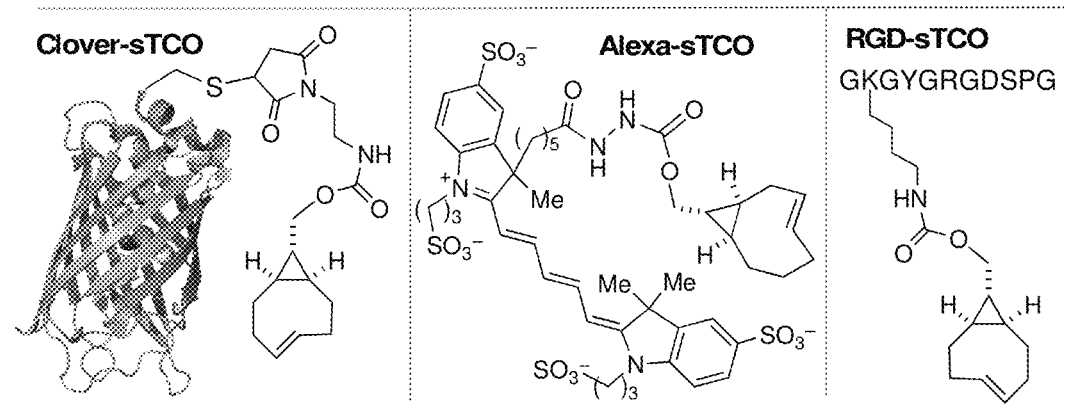

The inventors hypothesized that fibers could be synthesized with dihydrotetrazines and subsequently be activated and functionalized through bioconjugation. Thus, an aqueous solution of a water soluble bis-tetrazine monomer was combined with an organic soluble bis-sTCO containing a tethered dihydrotetrazine (FIG. 5, panel A). Again, meter-long, mechanically robust polymer fibers were continuously pulled from the liquid-liquid interface without fiber breakage (Video 1), confirming that the molecular weight of the polymer exceeds that required for chain entanglement. Subsequent oxidation by long wavelength photocatalysis was used to generate reactive tetrazine functionality, and the fibers could then be functionalized by sTCO conjugates of proteins, fluorophores or peptides. Shown in FIG. 5, panel B are the monomers 5 and 6 that were used to create the DHTz fibers. Notably, the DHTz containing bis-sTCO 5 was readily purified, stored and handled without special precautions. The sTCO conjugates used to elaborate the fibers are displayed in FIG. 5, panel B.

Figure 6:
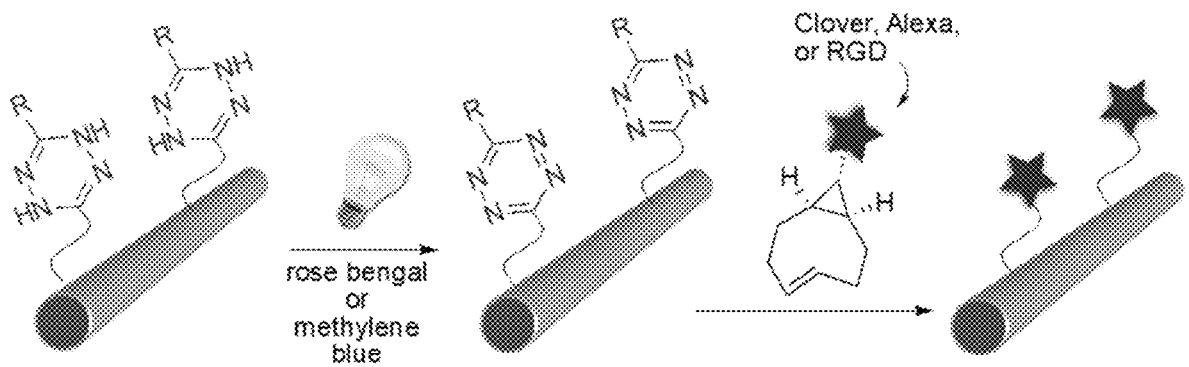
FIG. 6 is a schematic representation of fiber activation and subsequent conjugation according to the invention.

As shown in FIG. 6, the DHTz-fibers could be activated and then post-synthetically modified by treatment with Alexa-sTCO, Clover-sTCO or RGD-sTCO. The fibers were immersed in 100 μM sensitizer in PBS and irradiated with a simple incandescent bulb for 5 min. Methylene blue was used to activate fibers toward conjugations of Clover-sTCO or RGD-sTCO, and rose bengal was used as the sensitizer in experiments with Alexa-sTCO due to the spectral overlap of the Alexa dye with methylene blue. After irradiation, the fibers were rinsed, allowed to react with an sTCO conjugate for 1 min, and rinsed again. Confocal microscopy images of activated fibers conjugated by Alexa-sTCO or Clover sTCO showed that this short incubation time afforded labeling that was localized to the exterior of the fibers. Control experiments illustrated that dye conjugation was not efficient if the sensitizer or light was excluded. The inventors also found that HRP-catalyzed oxidation of dihydrotetrazines can be used to activate fibers toward bioconjugation, although in this instance photocatalytic activation is faster and more efficient.

The photocatalytic activation of tetrazines was also employed in the post-synthetic modification of the fibers with peptidic cues that promote cell adhesion and contact guidance. RGD-sTCO was conjugated to activated fibers through tetrazine ligation, and the resulting fibers were immobilized in silicone wells coated with poly(2-hydroxyethyl acrylate) to eliminate cellular adhesion to the culture wells. Here, imaging studies revealed fibroblasts selectively attached to RGD-tagged fibers and elongated along the long axis of the fibers, adopting a healthy fibroblastic morphology. Cell attachment and spreading was not observed in control experiments where the sensitizer and/or the RGD-sTCO were excluded. Instead, cells clustered to form multicellular spheroids, indicating the initiation of nemesis. These studies demonstrate the ability to functionalize biomimetic fibers with molecules that can enable visualization or promote cell adhesion.

As disclosed herein, photocatalytic and enzymatic methods for turning on the tetrazine ligation provide a new tool for modulating the cell adhesive properties of a biomaterial.

The inventors hypothesized that an intramolecular version of the Diels-Alder reaction would be rapid even when using an unstrained alkene, thereby enabling the synthesis of a drug delivery construct.

Figure 7:
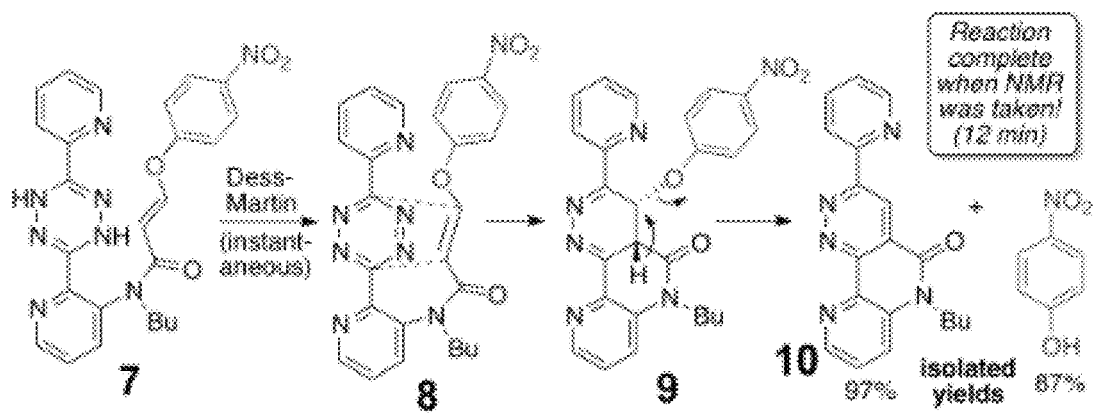
FIG. 7 shows experimental results demonstrating the viability of near infrared (NIR) photocatalytic payload release according to the invention.
Figure 7:
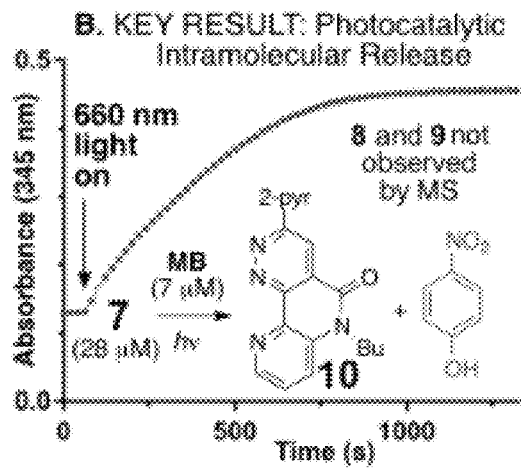
Figure 7:
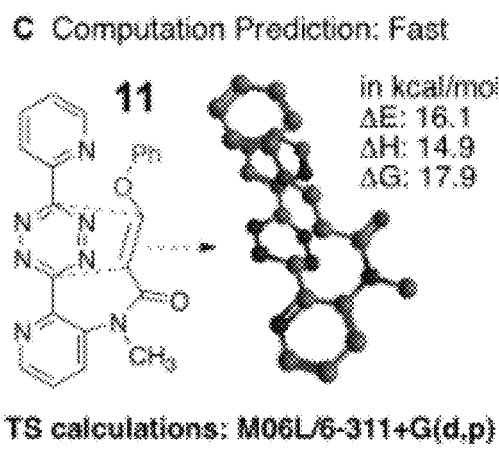

Shown in FIG. 7 are results that demonstrate the viability of NIR photocatalytic payload release. As shown in FIG. 7, panel C, high-level transition state calculations predicted that the intramolecular reaction of 11 would be rapid. Encouraged by calculation, the inventors synthesized the compound 7, where p-nitrophenol serves as a model payload that can be readily monitored by UV and NMR (FIG. 7, panel A). To study the Diels-Alder/elimination sequence (849410), the inventors chose to oxidize 7 with Dess-Martin periodinane—a reagent that instantaneously oxidizes dihydrotetrazines to tetrazines. They found that 7 reacts rapidly with Dess-Martin reagent, and upon the first ability to monitor by $^1$H NMR in CDCl$_3$ observed only product 10 and p-nitrophenol, which can be isolated in 97% and 87% yields, respectively. Upon LED irradiation (660 nm, 9.1 mW/cm$^2$) of 7 (28 μM) in MeOH in the presence of catalytic methylene blue (7 μM), complete oxidation/Diels-Alder/payload release within 15 minutes was observed (FIG. 7, panel B). In this photocatalytic reaction, aliquots by ESI-MS were analyzed, and intermediates 8 and 9 were not detected.

Figure 8:
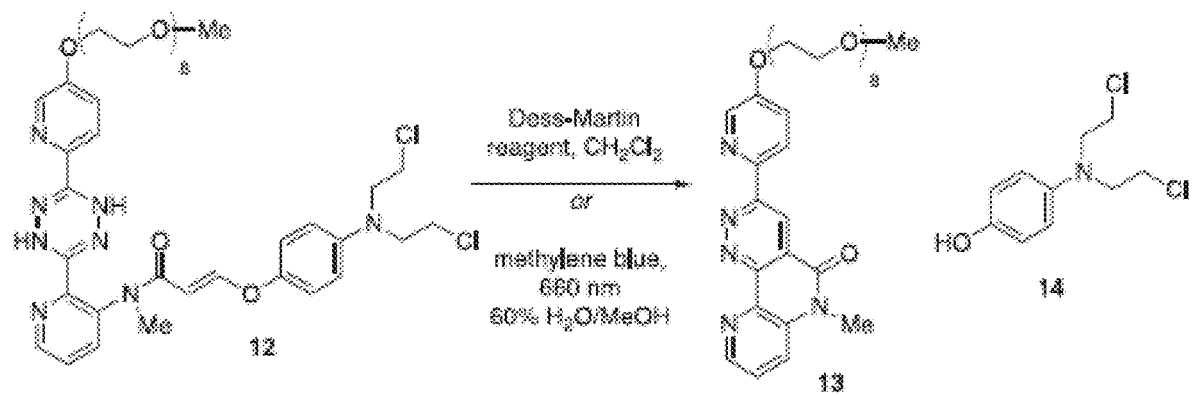
FIG. 8 shows a compound capable of functioning as a prodrug that, in the presence of an appropriate catalyst, can produce a phenolic nitrogen mustard drug, according to the invention.

Based on these findings, the inventors synthesized the compound 12, seen in FIG. 8, which has the potential to function as a prodrug that, in the presence of an appropriate catalyst, can produce the phenolic nitrogen mustard drug 14. Upon oxidation with Dess-Martin reagent, compound 12 was converted to the product 13 and the mustard 14. Monitoring by TLC and $^1$H NMR showed that the reaction was complete within 10 minutes. The reaction of 12 to produce 13 and 14 could also be promoted by irradiating a solution of 12 in 60% H$_2$O/MeOH for 30 min with a 660 nm LED light source in the presence of catalytic amounts of methylene blue with monitoring by UV-Vis. The complete conversion to product 13 could be observed by UV-vis within 30 minutes.

Inventive Methods

The invention provides a method for catalytically converting a dihydrotetrazine 1 into a tetrazine 2, wherein the dihydrotetrazine 1 comprises a first R group and a second R group, wherein the first R group is a substituted or unsubstituted aryl, heteroaryl, alkyl, alkenyl, alkynyl, carbonyl, or heteroatom-containing group, and the second R group is selected from the group consisting of H and substituted or unsubstituted aryl, heteroaryl, alkyl, alkenyl, alkynyl, carbonyl, and heteroatom-containing groups;

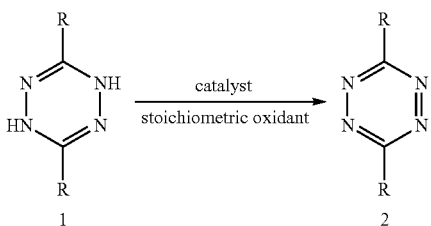

wherein the method comprises (a) providing the dihydrotetrazine 1 in a reaction medium, and (b) adding a catalyst and an oxidant to the reaction medium, whereby the dihydrotetrazine 1 is converted to the tetrazine 2.

The method may comprise adding an enzyme as a catalyst. The enzyme catalyst may be a horseradish peroxidase (HRP) or an ascorbate peroxidase. The ascorbate peroxidase may be APEX2 (SEQ ID NO:1), an engineered variant of ascorbate peroxidase or a mutated APEX2. The mutated APEX2 may comprise one or more mutations selected from the group consisting of F41A, A19V, D222G and a combination thereof. The method may also comprise converting the dihydrotetrazine 1 to the tetrazine 2 in the presence of superoxide dismutase (SOD).

The method may further comprise trapping the tetrazine with a dienophile, which may be an alkene or an alkyne, for example a strained alkene or strained alkyne. Specific examples include substituted trans-cyclooctenes or substituted cyclooctynes. The dienophile may be present with the dihydrotetrazine in the reaction medium before the catalyst is added. The method may unite one or more bimolecular entities selected from the group consisting of proteins, DNA, and RNA, or it may attach a fluorescent molecule or a fluorescent protein to another small molecule or a biomolecule. The method may attach a molecule to the surface of a fiber or a glass slide.

The dihydrotetrazine 1 used in performing a method according to the invention may comprises a first R group and a second R group, wherein the first R group is a substituted or unsubstituted aryl, heteroaryl, alkyl, alkenyl, alkynyl, carbonyl, or heteroatom-containing group, and the second R group is an aryl, heteroaryl, alkyl, or heteroatom-containing group to which is attached an alkene or alkyne moiety; wherein the alkene or alkyne moiety reacts intramolecularly with the tetrazine by Diels-Alder cycloaddition to form an adduct. In such cases said alkene moiety is attached, that moiety can bear a leaving group directly attached to the C1 or C2 carbon thereof, and the adduct undergoes elimination to produce a cycloadduct and liberate the leaving group. The leaving group may be an $OR^1$, $SR^1$, or $NR^1R^2$ group, wherein $R^1$ and $R^2$ are each individually selected from the group consisting of H, aryl, heteroaryl, alkyl, alkene, alkyne, carbonyl, and heteroatom-containing groups. Or, the leaving group may be $OR^1$ in which $R^1$ is an aryl or heteroaryl group, wherein the elimination produces a phenol or a heterophenol. Or, the leaving group may be $O(CO)NR^1R^2$, wherein $R^1$ and $R^2$ are each individually selected from the group consisting of H, aryl, heteroaryl, alkyl, alkene, alkyne, carbonyl, and heteroatom-containing groups. Elimination of the leaving group may result in formation of a biologically active material, for example a drug. The color and/or fluorescence properties of the products formed after said elimination differ from those prior to said oxidizing.

The catalyst may be a photocatalyst, and the method includes exposing the reaction mixture to light to activate the catalyst. The light may have a wavelength of 650 nm or longer.

The photocatalyst may be one of the following compounds or a derivative thereof:

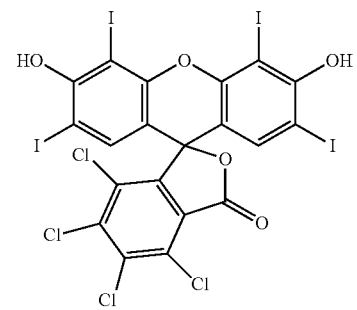

Rose Bengal

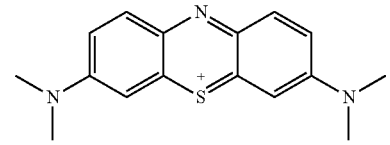

Methylene Blue

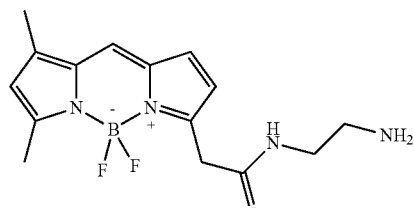

BODIPY FL DEA

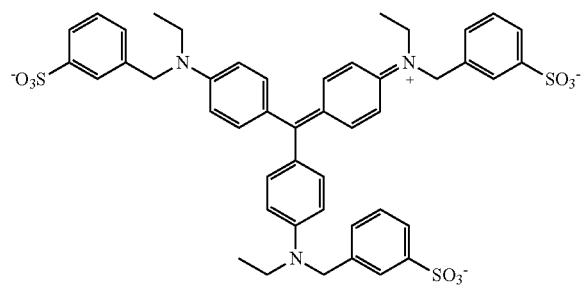

Coomassie Brilliant Blue

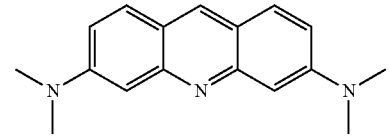

Acridine Orange

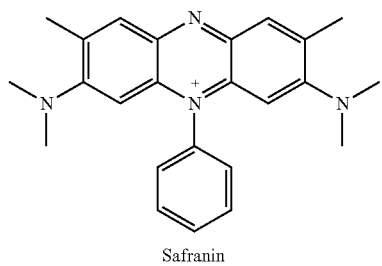

Safranin

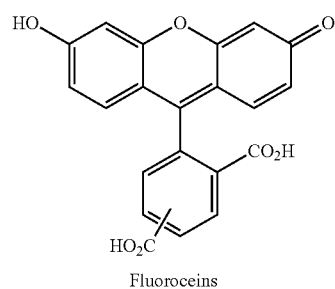

Fluoroceins

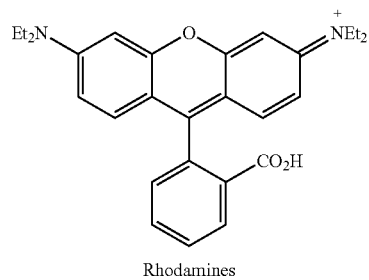

Rhodamines

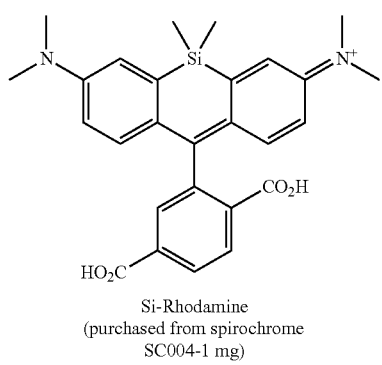

Si-Rhodamine
(purchased from spirochrome SC004-1 mg)

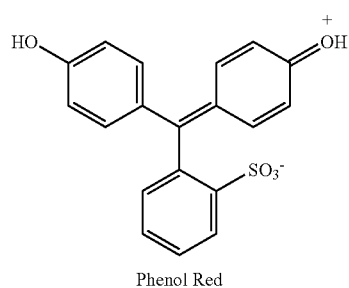

Phenol Red

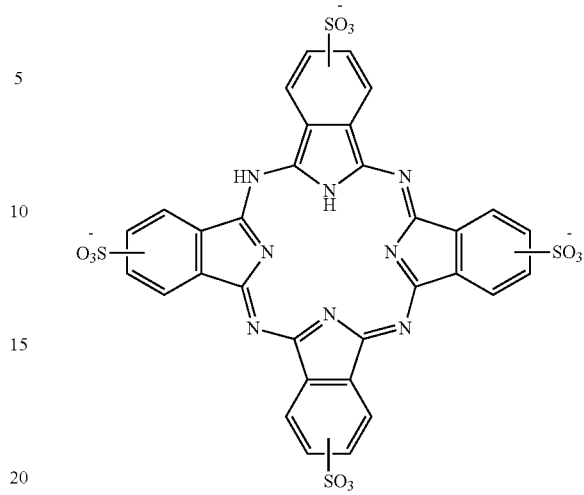

Phthalocyanine tetrasulfonate

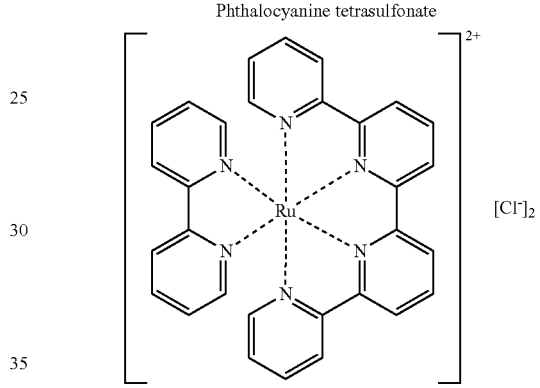

Tris(bipyridine)ruthenium(II) chloride

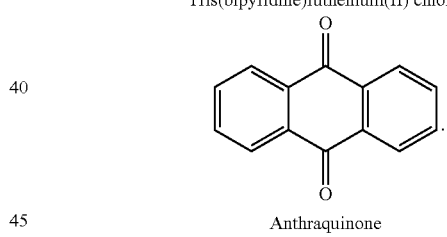

Anthraquinone

Or, the catalyst may be an enzyme, for example horseradish peroxidase. The catalyst may also be a metal compound, for example $FeCl_2$ or a metal-ligand complex. Exemplary metal-ligand complexes include iron-ligand complexes, for example an iron-porphyrin. Specific examples include Fe(III)tetrakis (1-methyl-4-pyridyl) porphyrin pentachloride and Fe(III)5,10,15,20-tetrakis(4-sulfonatophenyl)porphyrinato chloride.

The stoichiometric oxidant may be $O_2$, optionally atmospheric $O_2$ or atmospherically-derived dissolved $O_2$ in media. The $O_2$ may be at a concentration lower than that found under atmospheric conditions. Alternatively, the stoichiometric oxidant may be hydrogen peroxide or a disulfide.

The methods described herein may be carried out in a biological milieu, including but not limited to for example living cells and tissues, cell media, blood, serum, and cell lysates.

Inventive Compounds

The invention provides compounds useful in performing the methods described herein, or resulting from performing them. Examples of such compounds follow:

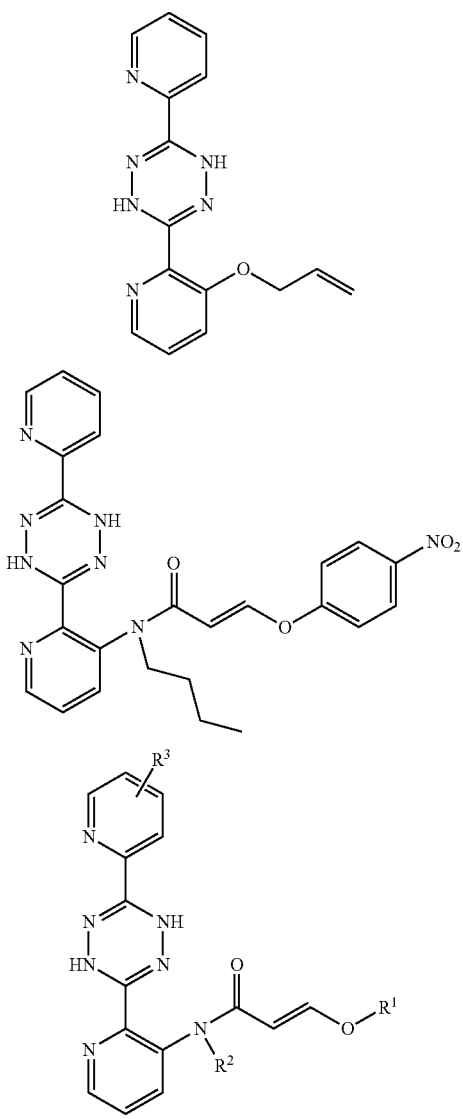

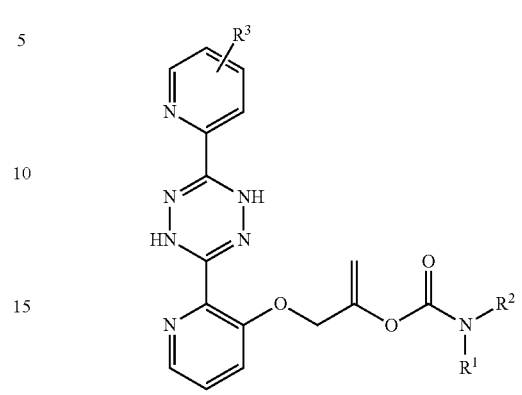

wherein R[1], R[2] and R[3] are each individually selected from the group consisting of H, aryl, heteroaryl, alkyl, alkenyl, alkynyl, carbonyl, and heteroatom-containing groups;

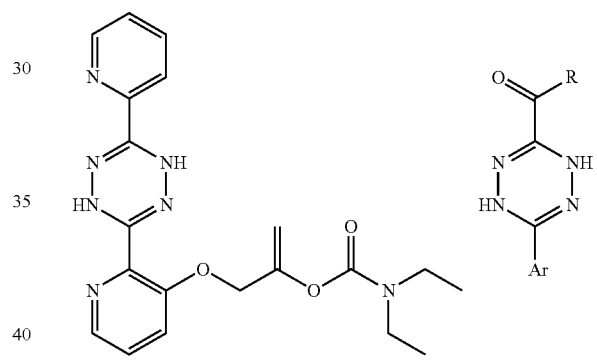

wherein R is selected from the group consisting of H, aryl, heteroaryl, alkyl, alkenyl, alkynyl, and heteroatom-containing groups, and Ar is an aromatic or heteroaromatic group wherein R[1], R[2] and R[3] are each individually selected from the group consisting of H, aryl, heteroaryl, alkyl, alkenyl, alkynyl, carbonyl, and heteroatom-containing groups;

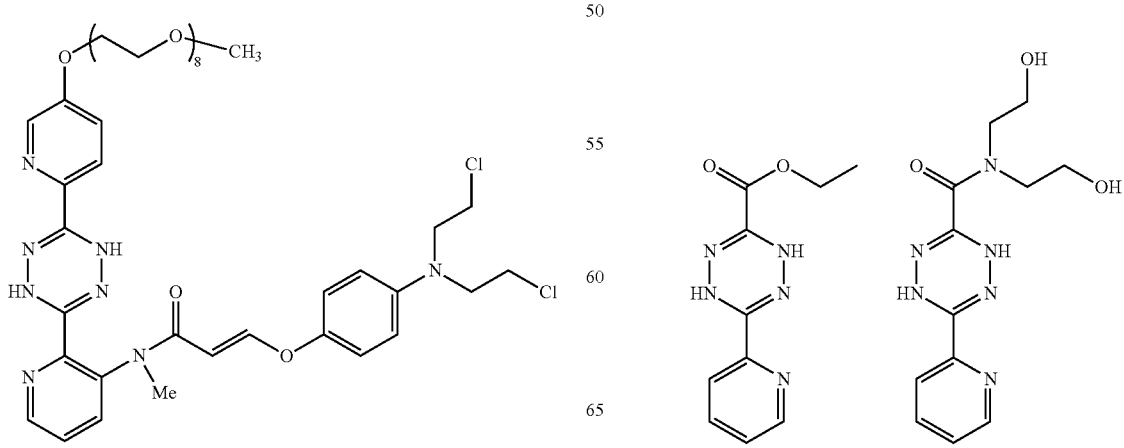

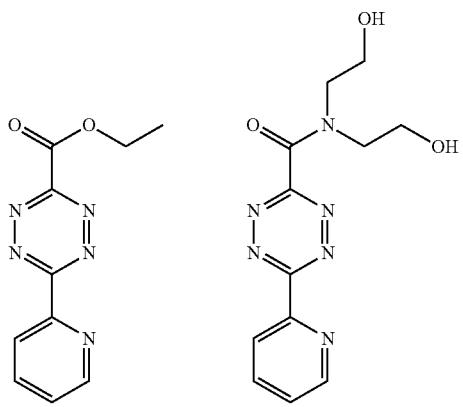

The dihydrotetrazine 1 may have the following structure:

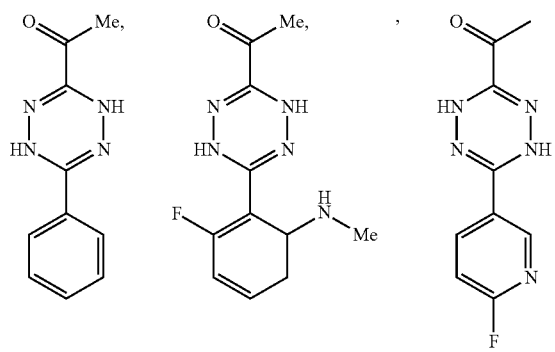

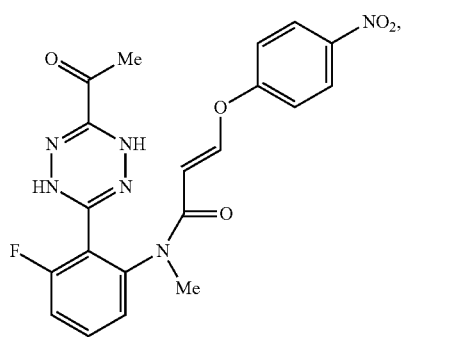

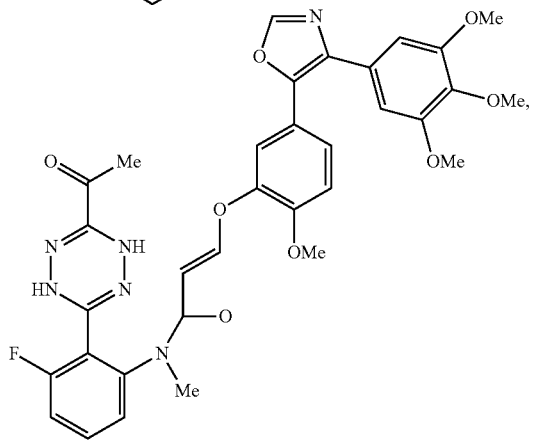

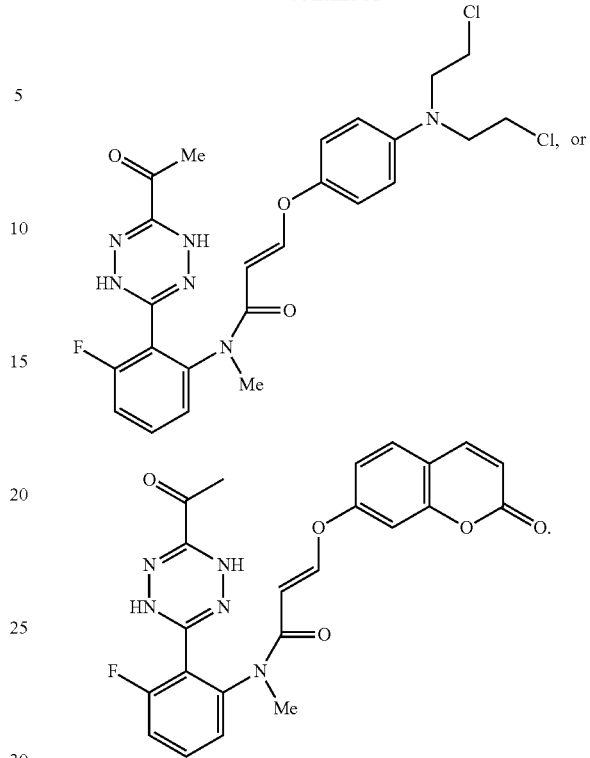

The dihydrotetrazine 1 may be conjugated to a compound having the following structure:

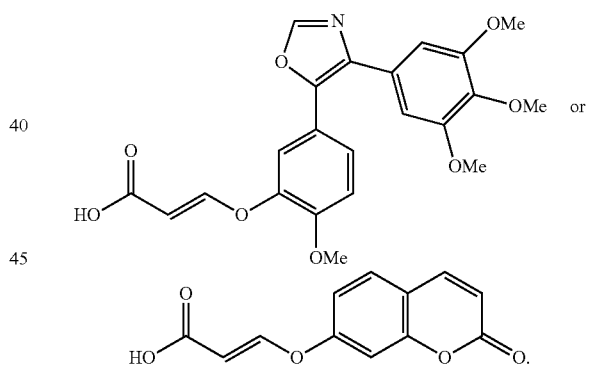

EXAMPLES

Synthetic Procedures
General Considerations

All reactions were carried out in glassware that was flame-dried under vacuum and cooled under nitrogen. THF was purified by distillation from Na/benzophenone. Phosphate-buffered saline (PBS) was prepared from diluting PBS 10× stock solution (Fisher Scientific). Flash Chromatography was performed using normal phase Silicycle silica gel (40-63D, 60 Å). An APT pulse sequence was used for $^{13}$C NMR spectra, where methylene and quaternary carbons appear 'up' (u), and methine and methyl carbons appear 'down' (dn). Other solvents and reagents were purchased from commercial sources without additional purification.

Synthesis of 4-oxo-4-((6-(6-(pyridin-2-yl)-1,4-dihydro-1,2,4,5-tetrazin-3-yl)pyridin-3-yl)amino)butanoic Acid (3a)

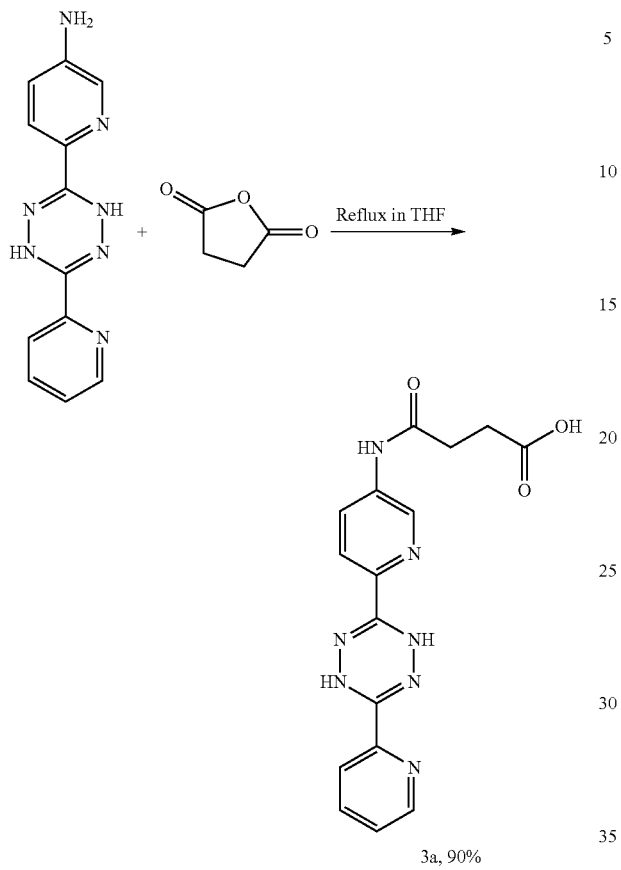

3a, 90%

To a dry round-bottom flask was added 6-(6-(pyridin-2-yl)-1,4-dihydro-1,2,4,5-tetrazin-3-yl)pyridin-3-amine (200 mg, 0.79 mmol, prepared as described in R. Selvaraj, J. M. Fox, *Tetrahedron Lett.* 2014, 55, 4795-4797), succinic anhydride (400 mg, 4.00 mmol) and anhydrous THF (8 mL). The mixture was refluxed for 24 hours at 60° C. and then cooled by an ice bath. The precipitate was filtered and sequentially washed by THF (2 mL) and ethyl acetate (3×3 mL) and dried to yield the title compound (251 mg, 0.71 mmol, 90%) as an orange solid.

Synthesis of 5-oxo-5-((6-(6-(pyridin-2-yl)-1,4-dihydro-1,2,4,5-tetrazin-3-yl)pyridin-3-yl)amino)pentanoic Acid (3b)

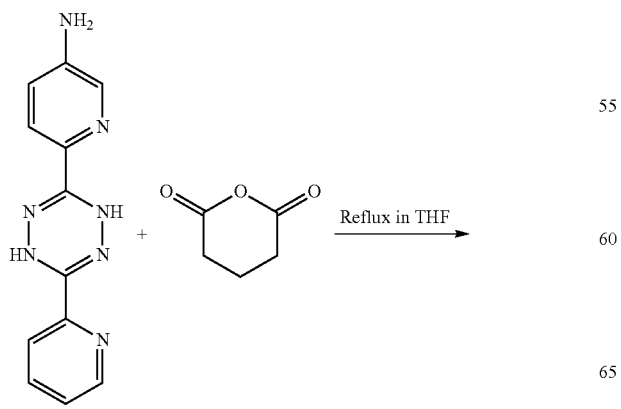

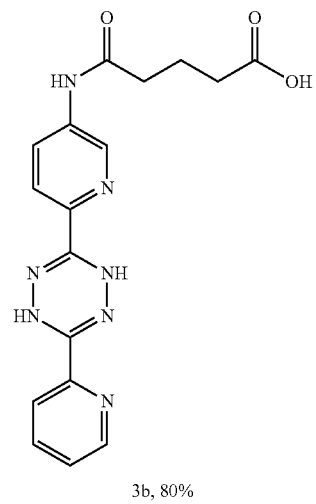

3b, 80%

To a dry round-bottom flask was added 6-(6-(pyridin-2-yl)-1,4-dihydro-1,2,4,5-tetrazin-3-yl)pyridin-3-amine (1.87 g, 7.39 mmol, prepared as described in R. Selvaraj, J. M. Fox, *Tetrahedron Lett.* 2014, 55, 4795-4797), glutaric anhydride (1.01 g, 8.87 mmol) and anhydrous THF (70 mL). The mixture was refluxed for 24 hours at 60° C. and then cooled by an ice bath. The precipitate was filtered on a Buchner funnel and sequentially rinsed by THF (10 mL) and ethyl acetate (3×10 mL) and dried to yield the title compound (2.16 g, 5.89 mmol, 80%) as an orange solid.

Synthesis of 4-oxo-4-((6-(6-(pyridin-2-yl)-1,2,4,5-tetrazin-3-yl)pyridin-3-yl)amino)butanoic Acid (4a)

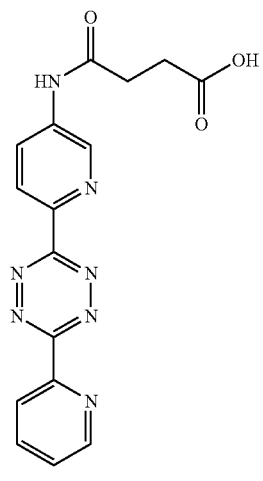

4a, 46%

To a flame dried flask under nitrogen, 6-(6-(pyridin-2-yl)-1,2,4,5-tetrazin-3-yl)pyridin-3-amine (50 mg, 0.20 mmol, prepared as described in R. Selvaraj, J. M. Fox, *Tetrahedron Lett.* 2014, 55, 4795-4797) and succinic anhydride (114 mg, 1.14 mmol) were added. The flask was charged with tetrahydrofuran (4 mL) and heated to 70° C. for 21 hours. The reaction solution was cooled to room temperature before diluting with ethyl acetate (4 mL) and further chilling to 0° C. for 15 minutes. Filtering and rinsing with ethyl acetate and diethyl ether (3×5 mL) yielded a dark, cherry red powder. The solid was dissolved in 1.5 mL warm dimethylformamide and purified by chromatography (10-100% acetone in hexanes then 1% acetic acid in acetone on 10% triethylamine in hexanes treated silica). After drying in vacuo, the recovered pink solid was rinsed with ice water yielding the title compound (32 mg, 46%). An additional 12 mg (24%) of 6-(6-(pyridin-2-yl)-1,2,4,5-tetrazin-3-yl)pyridin-3-amine was recovered during chromatography.

Synthesis of 2,5-dioxopyrrolidin-1-yl 5-oxo-5-((6-(6-(pyridin-2-yl)-1,4-dihydro-1,2,4,5-tetrazin-3-yl)pyridin-3-yl)amino)pentanoate (S1)

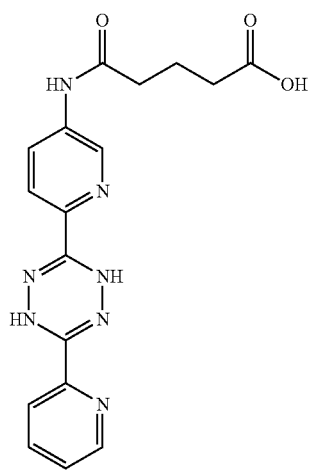

+

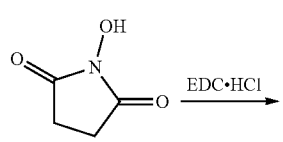

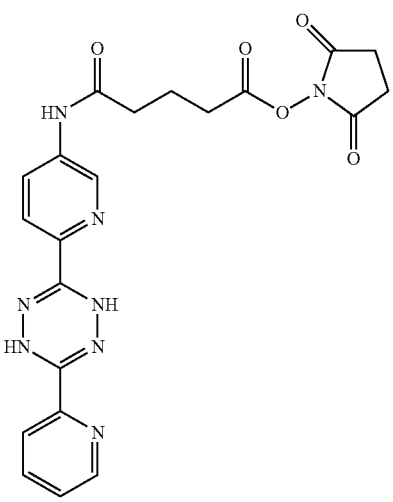

S1, 80%

To a dry round-bottom flask was added 1 (200 mg, 0.54 mmol), N-hydroxysuccinimide (125 mg, 1.09 mmol), N-(3-dimethylaminopropyl)-N'-ethylcarbodiimide hydrochloride (209 mg, 1.09 mmol) and anhydrous DMF (2 mL). The mixture was stirred for 1 hour at room temperature. DMF was removed by rotary evaporation at 50° C. using an efficient vacuum pump (<1 torr). The crude product was dissolved in acetone and then concentrated onto silica gel. Purification by column chromatography using a gradient (10%-70%) of acetone in hexanes yielded 202 mg (0.44 mmol, 80%) of the title compound as an orange solid.

Synthesis of bis(((E)-bicyclo[6.1.0]non-4-en-9-yl)methyl) (2-hydroxypropane-1,3-diyl)dicarbamate (S2)

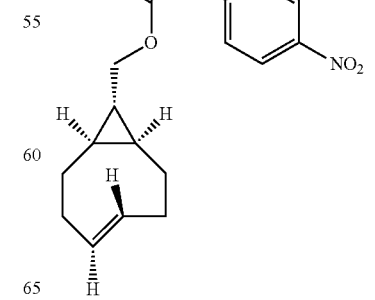

+

27

-continued

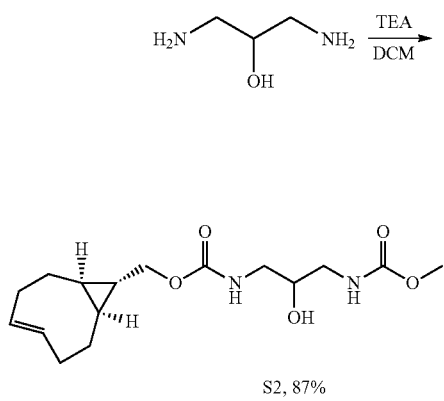

S2, 87%

A dry round-bottom flask was sequentially charged via syringe with a solution of 1,3-diamino-2-propanol (120 mg, 1.33 mmol) in anhydrous dichloromethane (20 mL) followed by anhydrous triethylamine (744 µL, 5.37 mmol) and (1R,8S,9R,4E)-bicyclo[6.1.0]non-4-en-9-ylmethyl(4-nitrophenyl) carbonate (930 mg, 2.93 mmol, prepared as described in M. T. Taylor, M. L. Blackman, O. Dmitrenko, J. M. Fox, *J. Am. Chem. Soc.* 2011, 133, 9646-9649). The mixture was stirred overnight at room temperature, diluted with dichloromethane (30 mL) followed by exhaustive aqueous wash (5×50 mL). The organic layer was dried with MgSO₄, filtered and then the solvent was removed with a rotary evaporator. Purification by column chromatography first using 10% ethyl acetate in hexanes then switching to 30% acetone in hexanes yielded the title compound (520 mg, 1.16 mmol, 87%) as a colorless oil.

28

Synthesis of bis(((E)-bicyclo[6.1.0]non-4-en-9-yl)methyl) (2-(((4-nitrophenoxy)carbonyl)oxy)propane-1,3-diyl)dicarbamate (S3)

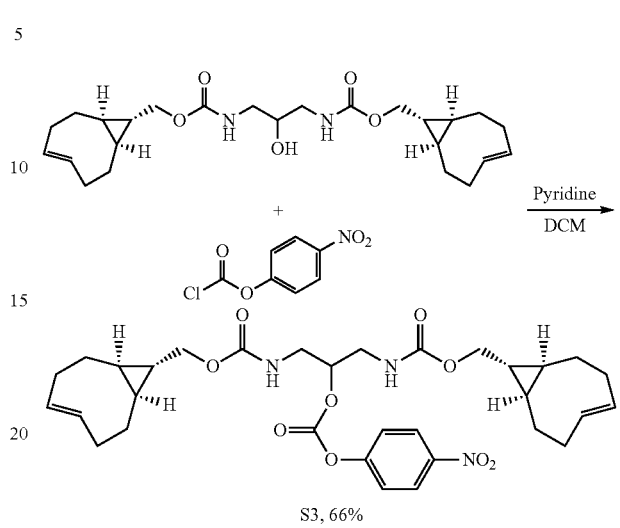

S3, 66%

A dry round-bottled flask was charged with S2 (500 mg, 1.12 mmol). Anhydrous dichloromethane (30 mL) and pyridine (0.23 mL, 2.80 mmol) were added to the flask. A solution of 4-nitrophenylchloroformate (271 mg, 1.34 mmol) in anhydrous dichloromethane (4 mL) was added to the flask via syringe and the solution was stirred for 1 h at room temperature. Saturated aq. NH₄Cl was added to the mixture and the layers were separated, and the aqueous layer was extracted twice with dichloromethane. The organic layers were combined, dried with MgSO₄ and filtered, and the solvent was removed using a rotary evaporator. Purification by column chromatography (10% to 30% ethyl acetate/hexanes) yielded 450 mg (0.74 mmol, 66%) of the title compound as a white solid.

Synthesis of bis(((E)-bicyclo[6.1.0]non-4-en-9-yl)methyl) (2-M2-aminoethyl)carbamoyl)oxy)propane-1,3-diyl)dicarbamate (S4)

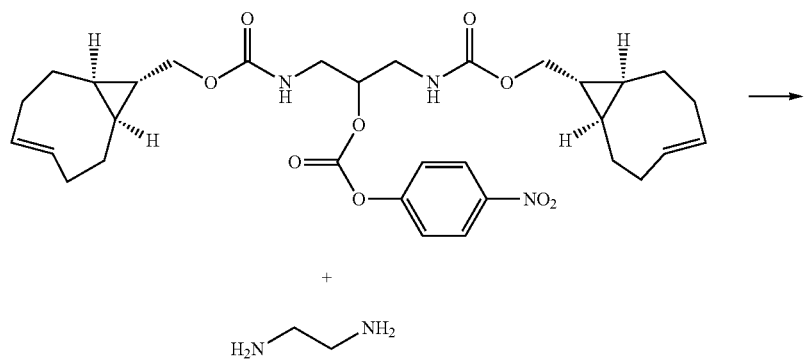

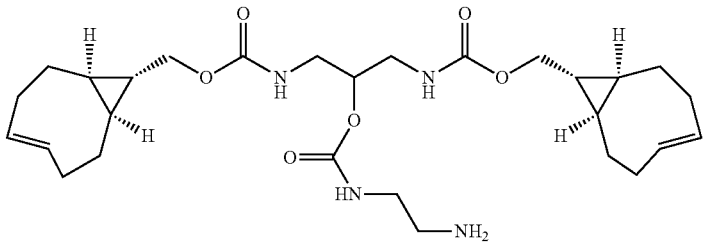

S4

A dry round-bottom flask was sequentially charged via syringe with ethylenediamine (218 µL, 3.27 mmol) followed by a solution of S3 (100 mg, 0.16 mmol) in anhydrous dichloromethane (4 mL). The solution was stirred for 1 h at room temperature, diluted with dichloromethane (15 mL) and followed by exhaustive aqueous washes (5×30 mL). The organic layer was dried with MgSO₄, filtered and concentrated down with a rotary evaporator to afford the title compound (80 mg, 92% crude yield) as a pale yellow solid. The crude product was carried to the next step of synthesis without further purification.

Synthesis of bis(((E)-bicyclo[6.1.0]non-4-en-9-yl)methyl) (2-(((2-(5-oxo-5-((6-(6-(pyridin-2-yl)-1,4-dihydro-1,2,4,5-tetrazin-3-yl)pyridin-3-yl)amino)pentanamido)ethyl)carbamoyl)oxy)propane-1,3-diyl) dicarbamate (5)

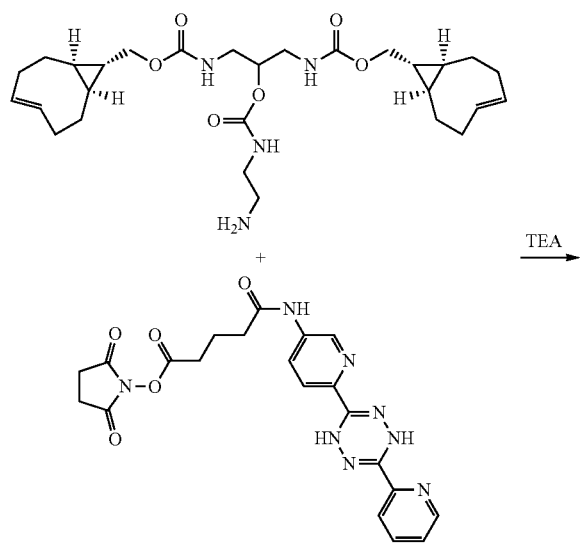

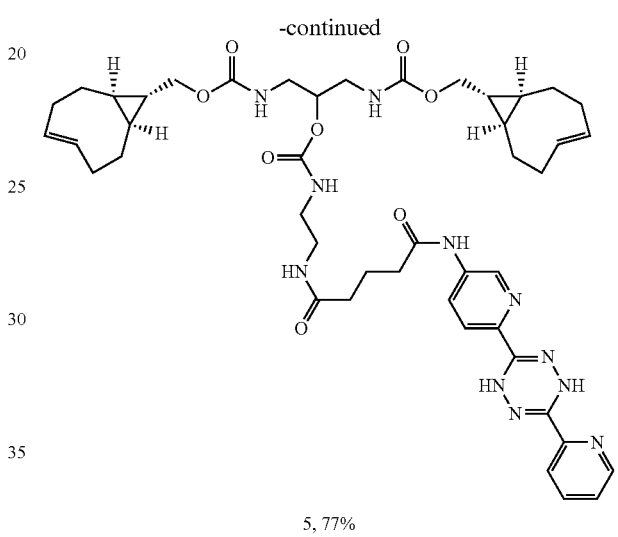

5, 77%

To a dry round-bottom flask was added S4 (39 mg, 73.3 µmol), S1 (25 mg, 53.9 µmol) and a solution of triethylamine (17 µL, 0.12 mmol) in dichloromethane (2 mL). The mixture was stirred for 1 hour under room temperature and then concentrated onto silica gel using a rotary evaporator. Purification by column chromatography using a gradient (20%-70%) of acetone in hexanes yielded the title compound (37 mg, 42.0 µmol, 77%) as an orange solid.

N-Terminal Cysteine-Tagged Clover-GFP

The Clover construct sequence (A. J. Lam, F. St-Pierre, Y. Gong, J. D. Marshall, P. J. Cranfill, M. A. Baird, M. R. McKeown, J. Wiedenmann, M. W. Davidson, M. J. Schnitzer, et al., *Nat. Methods* 2012, 9, 1005-12) coding for this green fluorescent protein with an additional N-terminal extension (MGSGSCGSGS), was ordered from GeneWiz and inserted into the pET28a vector via XbaI and NcoI restriction sites. Plasmids were transformed and expressed in BL21(DE3) cells. Cells were grown at 37° C. in 2 L of Luria-Bertani medium containing 30 µg/mL kanamycin and induced by the addition of 1.0 mM isopropyl β-D-1-thiogalactopyranoside when the absorbance at 600 nm reached 0.6 AU. Cells were grown for 6 h and collected by centrifugation (at 3,000 g for 10 minutes at 4° C.). Cell pellets were resuspended in 50 mM phosphate buffer, pH 7.5, containing 500 mM NaCl, 1 mM phenylmethylsulfonyl fluoride, 300 µg/mL lysozyme, and 1 µM leupeptin. Cells were disrupted by two passes through a French pressure cell (at 10,000 psi), and the resulting homogenate was briefly sonicated to shear DNA. The suspension was clarified by centrifugation (at 17,000 g for 30 minutes at 4° C.), and the supernatant was rocked with 3 mL of a nickel affinity resin (Sigma HIS-Select Nickel Affinity Gel) for 1 hour at 4° C. The resin-bound protein was loaded into a small column and washed with 40 mL of 50 mM phosphate buffer, pH 7.5, containing 500 mM NaCl, followed by 40 and 20 mL washes of the same buffer with an additional 5 and 20 mM imidazole respectively. The constructs were then eluted from the column with 20 mL of 50 mM phosphate buffer, pH 7.5, containing 500 mM NaCl and 200 mM imidazole, and then dialysed overnight against 4 L of 50 mM phosphate buffer, pH 7.5, containing 1 mM EDTA. The protein was then concentrated to 1 mL and stored at −20° C. The protein construct was >95% pure by SDS-PAGE.

Figure 9:
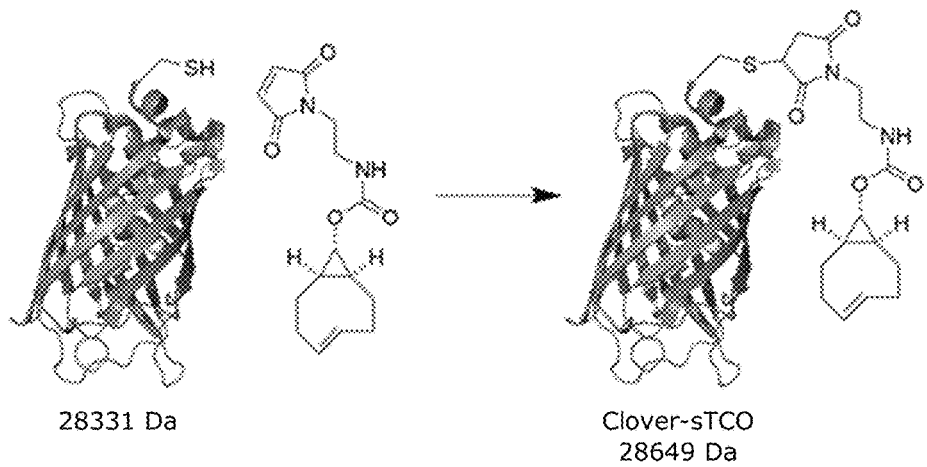
FIG. 9 shows an exemplary preparation of Clover-sTCO, according to the invention.

Preparation of Clover-sTCO, as Shown in FIG. 9

A 0.5 mL solution of 1.02 mM Clover protein solution in phosphate buffer (50 mM, 1 mM EDTA, pH 7.5) was reduced with an aqueous solution of tris(hydroxypropyl)phosphine (THP) (50 µL of a 100 mM solution, 10 mM final concentration) for 2 hours at room temperature. The reduced protein was loaded onto a desalting column (GE Healthcare PD-10) pre-equilibrated and eluted with phosphate buffer (50 mM, 1 mM EDTA, pH 7.5). Approximately 1.2 mL of pure fractions was collected, containing fully reduced 104 µM Clover protein. The thiol content of the resulting solution was verified by treating a small volume with Ellman's reagent. Concentration was determined by UV-Vis spectrometry using the Clover extinction coefficient of 111,000 $M^{-1}cm^{-1}$. Approximately 1.2 mL of a 104 µM reduced Clover solution in phosphate buffer (50 mM, 1 mM EDTA, pH 7.5) was incubated with a 10 mM DMSO solution of sTCO-MaleimideI (62.4 µL, final concentration 520 µM) for 30 minutes. The reaction solution was concentrated using a centrifugal filter (Millipore Ultracel 3k MWCO) at 4,000 rpm for 15 minutes. The concentrated solution was loaded onto a desalting column (GE Healthcare PD-10) pre-equilibrated and eluted with phosphate buffer (50 mM, 1 mM EDTA, pH 7.5). Approximately 1.0 mL of 103 µM conjugated Clover protein was collected.

Synthesis of RGD-sTCO

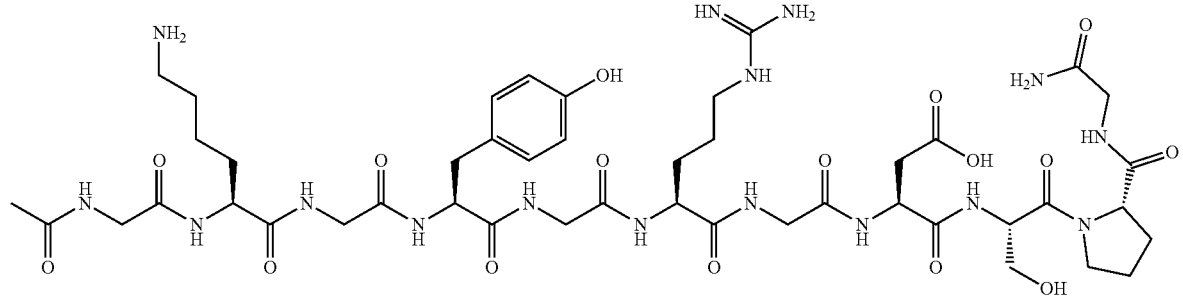 [SMILES: CC(=O)NCC(=O)N[C@@H](CCCCN)C(=O)NCC(=O)N[C@@H](Cc1ccc(O)cc1)C(=O)NCC(=O)N[C@@H](CCCNC(=N)N)C(=O)NCC(=O)N[C@@H](CC(=O)O)C(=O)N[C@@H](CO)C(=O)N1CCC[C@H]1C(=O)NCC(N)=O]

A cell-adhesive peptide with sequence of GKGYGRGD-SPG was prepared on a PS3 peptide synthesizer (Protein technologies Tucson, Ariz.) using the Rink Amide resin (EMD Millipore, Ill.) following standard Fmoc solid phase peptide synthesis protocols. The Rink Amide-MBNA resin (0.25 mmol) was swollen in DMF for 15 minutes on the peptide synthesizer before the Fmoc group was removed by a piperidine/DMF solution (20 vol %). After the resin was thoroughly washed with DMF, a 4-fold excess of Fmoc-protected amino acid (1.0 mmol) HBTU (379 mg, 1.0 mmol) and 4-methylmorpholine DMF solution were added to the reaction vessel for standard amine-carboxylic acid coupling. A coupling time of 1 hour was used for all the amino acids. After each coupling step, excess reactants were washed off using DMF, and the Fmoc group was removed before the addition of the next residue. At the end of the peptide synthesis, the amine group at the N-terminus was acetylated with acetic anhydride (5 mL, 20% in DMF, with 0.3 mL DIPEA) for 20 min. The peptide was cleaved and deprotected in TFA/$H_2O$/triisopropylsilane (95/2.5/2.5, v/v) for 3 hours and precipitated in cold diethyl ether, leaving and amide functionality at the C-terminus of the peptide product. HPLC purification followed by lyophilization afforded the title compound as dry powder.

RGD-sTCO

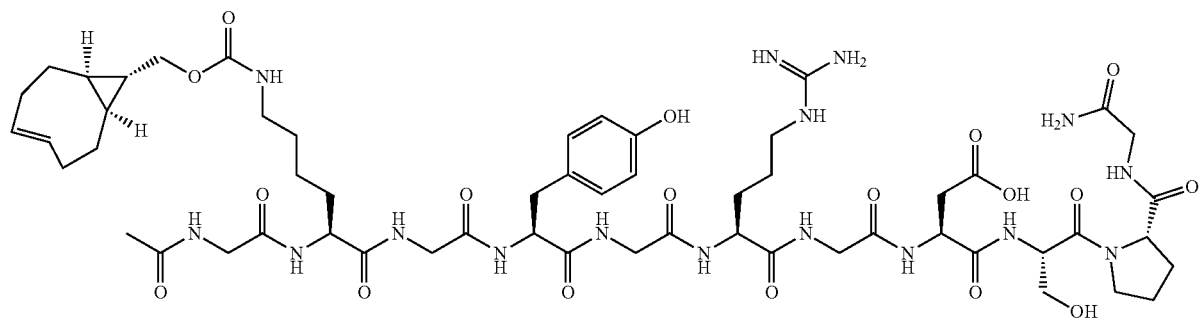

RGD peptide (42 mg, 38.5 μmol) was dissolved in 550 μL of anhydrous DMF and N,N-diisopropylethylamine (17 μL, 97.6 μmol) was added followed by (1R,8S,9R,4E)-bicyclo[6.1.0]non-4-en-9-ylmethyl(4-nitrophenyl) carbonate[1] (18 mg, 56.7 μmol). The reaction was stirred at room temperature for 3 hours. The resulting solution was added dropwise to 35 mL of diethyl ether. The crude product was obtained by precipitation followed by centrifugation (5,000 rpm, 5 minutes). The precipitation/centrifugation procedure was repeated two additional times and then the crude product was purified by HPLC using a gradient of 5% to 95% acetonitrile in pH neutral water (i.e. without TFA or formic acid modifier). Collected fractions were lyophilized and stored in −20° C. freezer. HPLC purification afforded 39 mg of sTCO-RGD conjugate (30.8 μmol, 80%).

DHTz Drug Release

Intermolecular Diels-Alder/aromatization sequence between 3,6-di(pyridin-2-yl)-1,2,4,5-tetrazine and vinyl diethylcarbamate

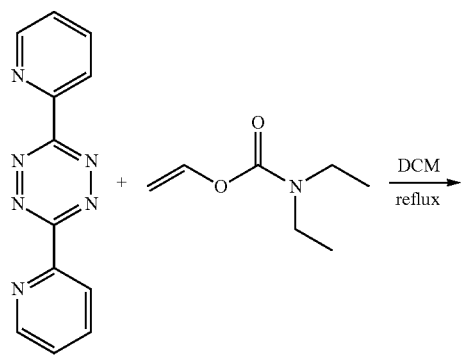

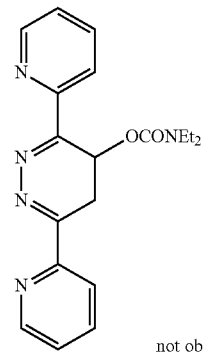

not observed

In a typical experiment, vinyl diethylcarbamate (60.0 mg, 0.420 mmol, 5.00 equiv) and 3,6-di(pyridin-2-yl)-1,2,4,5-tetrazine and vinyl diethylcarbamate (20.0 mg, 0.0846 mmol, 1.00 equiv) were dissolved in 2 mL CD₃OD. The reaction was stirred at room temperature for 48 hours, after which ¹H NMR was taken. Diethyl amine (36% NMR yield) was released and shown on NMR. Aromatization product was also present on NMR.

Dess-Martin Periodinane Oxidation and Intramolecular Diels-Alder/Aromatization Sequence: 3-(pyridin-2-yl)-5H-pyrido[2′,3′:5,6]pyrano[4,3-c]pyridazine

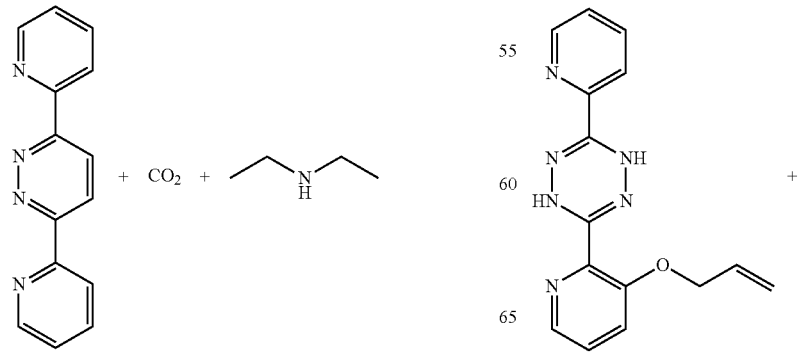

+

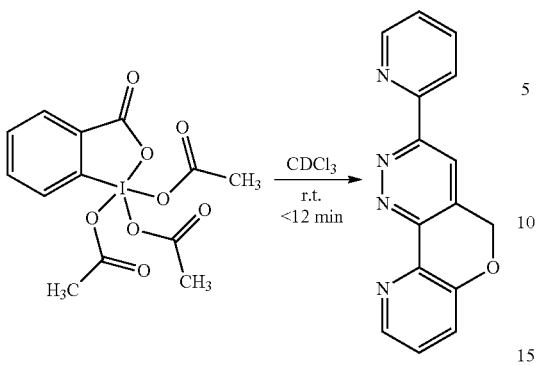 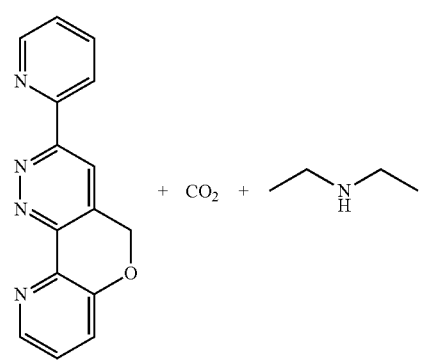

NMR experiment: A typical Dess-Martin oxidation and intramolecular Diels-Alder/aromatization reaction sequence was performed in CDCl$_3$ and $^1$H NMR. Thus, 3-(3-(allyloxy)pyridin-2-yl)-6-(pyridin-2-yl)-1,4-dihydro-1,2,4,5-tetrazine (10.3 mg, 0.034 mmol, 1.00 equiv) was dissolved in 1 mL CDCl$_3$ in a 7 mL vial. Dess-Martin periodinane (22.2 mg, 0.051 mmol, 1.50 equiv) was added to the reaction. The mixture was stirred at room temperature for 3 min. The mixture was then transferred to a NMR tube and $^1$H NMR experiment was performed quickly. The overall time duration (from the beginning of reaction to final NMR spectrum) was 12 minutes. No alkene peak of 3-(3-(allyloxy)pyridin-2-yl)-6-(pyridin-2-yl)-1,4-dihydro-1,2,4,5-tetrazine was shown on proton NMR, indicating the intramolecular Diels-Alder was finished.

Preparative experiment: Dess-Martin periodinane (30.0 mg, 0.0707 mmol, 2.00 equiv.) was added to a DCM 4.00 mL solution of 3-(3-(allyloxy)pyridin-2-yl)-6-(pyridin-2-yl)-1,4-dihydro-1,2,4,5-tetrazine (10.4 mg, 0.0353 mmol, 1.00 equiv). After 30 min, the reaction mixture was quenched with 10 mL NaHCO$_3$ (sat.) and 10 mL DCM. The aqueous layer was extract with 10 mL DCM three times. The organic layers were combined, dried over MgSO$_4$ and concentrated via rotary evaporator. Purification by flash chromatography (1%-2% methanol/dcm) gave 3-(pyridin-2-yl)-5H-pyrido[2',3':5,6]pyrano[4,3-c]pyridazine (9.00 mg, 97%) as a white solid.

UV-Vis Experiment with HRP and 3-((2-(6-(pyridin-2-yl)-1,4-dihydro-1,2,4,5-tetrazin-3-yl)pyridin-3-yl)oxy)prop-1-en-2-yl Diethylcarbamate 50 μM 3-((2-(6-(pyridin-2-yl)-1,4-dihydro-1,2,4,5-tetrazin-3-yl)pyridin-3-yl)oxy)prop-1-en-2-yl diethylcarbamate (in 90% 1×PBS, 10% MeOH, no EDTA, 25 degree) was mixed with 15 μL HRP (2.06 μM). The reaction was monitored by UV-Vis over 60 min. Aromatized product was formed eventually.

Synthesis Procedure for Dihydrotetrazine Substrates: N-(tert-butyl)-3-methylpicolinamide

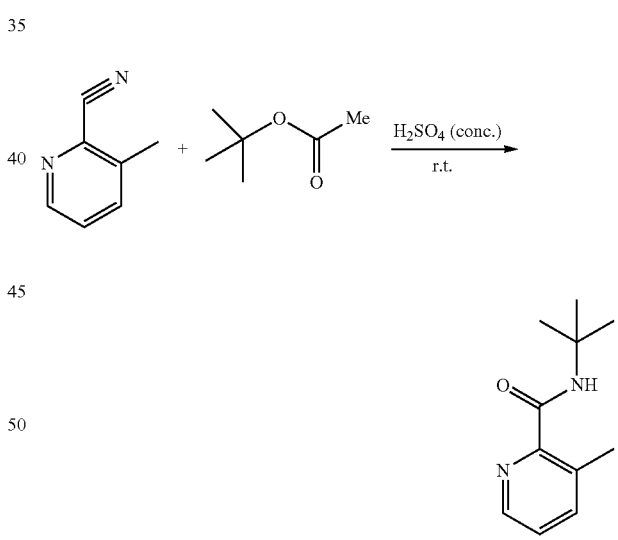

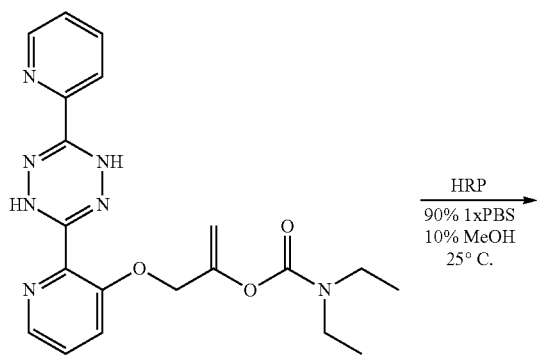

To a solution of 2-cyano-3-methylpyridine (1.20 g, 12.0 mmol) in tert-butyl acetate (10.0 mL) was added concentrated H$_2$SO$_4$ (1.00 mL), and the mixture was stirred at room temperature overnight before it was diluted with water. The mixture was then carefully neutralized by adding NH$_4$OH at 0° C. and then extracted twice with 1:1 hexane-EtOAc. The combined organics were washed with saturated brine, dried (Na$_2$SO$_4$), filtered, and concentrated. The residue was chromatographed on silica gel to give N-(tert-butyl)-3-methylpicolinamide (1.85 g, 95%) as a colorless solid.

3-(but-3-en-1-yl)-N-(tert-butyl)picolinamide

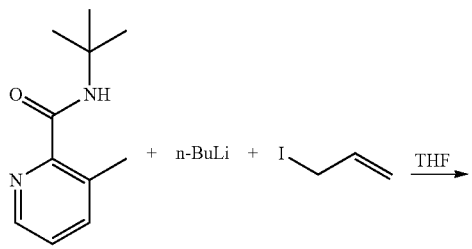

N-(tert-butyl)-3-methylpicolinamide (1.45 g, 7.54 mmol, 1.00 equiv.) was dissolved in 29.0 mL dry THF. The solution was chilled to −40° C. nBuLi (6.03 mL 15.08 mmol, 2.00 equiv., 2.50 M in) was added dropwise to the solution at −40° C. The reaction was stirred at −40° C. for 10 min. Allyl iodide was added to the reaction dropwise. The reaction mixture was further stirred for 30 min, during which time the solution was allowed to be warmed up to room temperature. The reaction was then quenched with 2.00 mL water. THF was removed via rotary evaporator. The reaction mixture was diluted with 30 mL Brine and 30 mL ethyl acetate. The aqueous layer was extracted with 30 mL ethyl acetate three times. The organic layers were combined, dried over MgSO$_4$ and concentrated. Purification by flash chromatography (5% ethyl acetate/hexane) gave 3-(but-3-en-1-yl)-N-(tert-butyl) picolinamide (1.49 g, 85%) as a yellow oil.

3-(but-3-en-1-yl)picolinonitrile

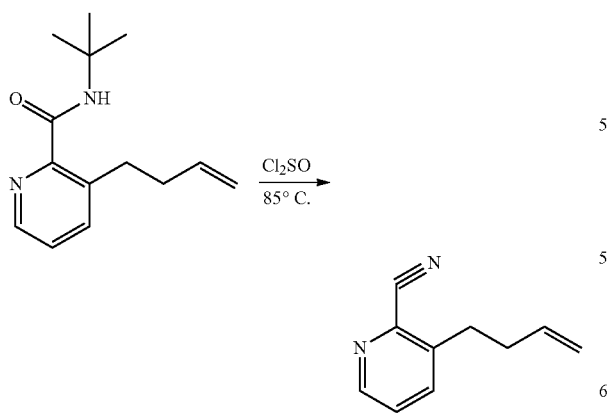

A mixture of 3-(but-3-en-1-yl)-N-(tert-butyl)picolinamide (1.00 g, 4.06 mmol, 1.00 equiv) and thionyl chloride (10.0 mL 138 mmol, 34.0 equiv.) was heated at 85° C. for 3 hours. The mixture was then cooled down to room temperature. Excess amount of thionyl chloride was removed via distillation. The mixture was quenched with 10 mL 10% NaOH solution and 10 mL DCM. The aqueous layer was extract with 10 mL DCM for three times. The organic layers were combined, dried over MgSO$_4$ and concentrated. Purification by flash chromatography (5%-15% ethyl acetate/hexane) gave 3-(but-3-en-1-yl)picolinonitrile (0.524 g, 75%) as a yellow oil.

3-(3-(but-3-en-1-yl)pyridin-2-yl)-6-(pyridin-2-yl)-1,4-dihydro-1,2,4,5-tetrazine

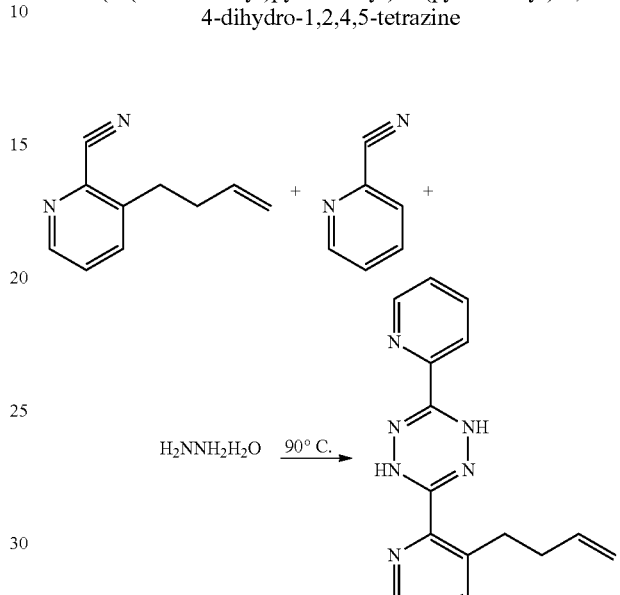

To a 25 mL round bottom flask, 3-(but-3-en-1-yl)picolinonitrile (228 mg, 1.44 mmol, 1.00 equiv.), picolinonitrile (451 mg, 4.33 mmol, 3.00 equiv.) and hydrazine monohydrate (0.564 mL 11.5 mmol, 8.00 equiv.) were added. The reaction mixture was stirred at 90° C. for overnight. After the reaction, 10 mL Brine and 10 mL ethyl acetate were added to the mixture. The aqueous layer was extract with 10 mL ethyl acetate for four times. The organic layers were combined, dried over MgSO$_4$ and concentrated. Purification by flash chromatography (5% ethyl acetate/hexane) gave 3-(3-(but-3-en-1-yl)pyridin-2-yl)-6-(pyridin-2-yl)-1,4-dihydro-1,2,4,5-tetrazine (84 mg, 20%) as a yellow solid.

3-(allyloxy)picolinonitrile

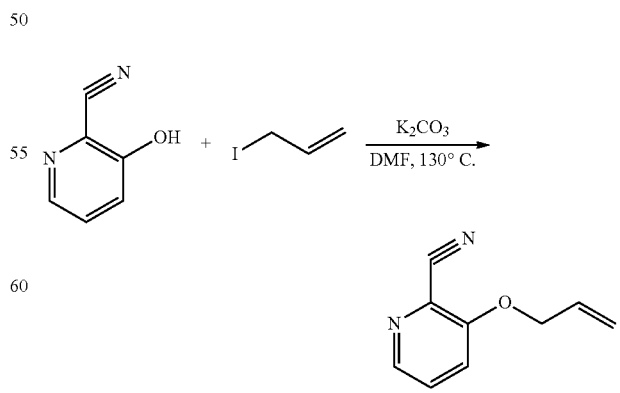

To a stirred DMF (29.5 mL) solution of 3-hydroxypicolinonitrile (500 mg, 4.16 mmol, 1.00 equiv) and potassium carbonate (3.45 g, 24.96 mmol, 6.00 equiv) was added allyl iodide (1.15 mL, 12.5 mmol, 3.00 equiv). The reaction was heated up to 130° C. overnight. The reaction mixture was cooled to room temperature. DMF was removed via high vacuum rotary evaporation. The mixture was diluted with 30 mL Brine and extracted with ethyl acetate (3×30 mL). The organics were combined and dried over MgSO₄, filtered, and concentrated via rotary evaporation. Purification by flash column chromatography (15%-30% ethyl acetate/hexane) afforded the title compound as yellow oil (503 mg, 76% yield)

3-(3-(allyloxy)pyridin-2-yl)-6-(pyridin-2-yl)-1,4-dihydro-1,2,4,5-tetrazine

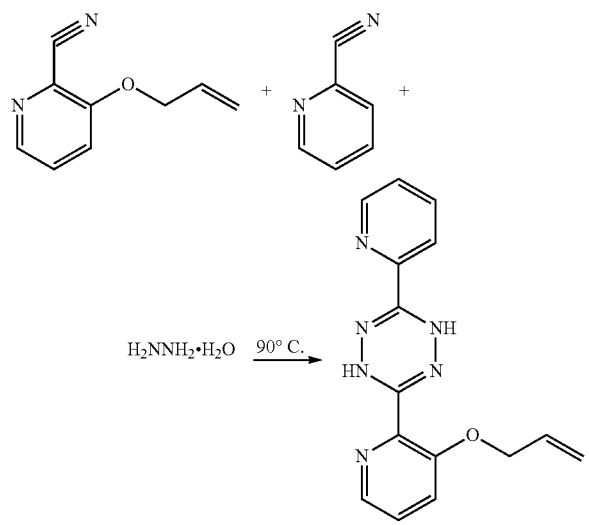

A 10 mL single neck round-bottom flask was charged with 3-(allyloxy)picolinonitrile (200 mg, 1.25 mmol, 1.00 equiv). In a separate flask, 2-cyanopyridine (0.361 mL, 3.74 mmol, 3.00 equiv) was melted by gentle warming, and added to the flask containing 3-(allyloxy)picolinonitrile. Hydrazine hydrate (0.609 mL, 12.5 mmol, 10.00 equiv) was added, and the flask was fitted with reflux condenser and heated to 90° C. overnight under N₂. The reaction mixture was cooled to r.t. and 10 mL Brine was added. The aqueous layer was extract with 3×10 mL ethyl acetate. The organics were combined and dried over MgSO₄, filtered, and concentrated via rotary evaporation. Purification by flash column chromatography (20%-30% ethyl acetate/hexane) afforded the title compound as yellow solid (84.4 mg, 23% yield).

prop-1-en-2-yl Diethylcarbamate

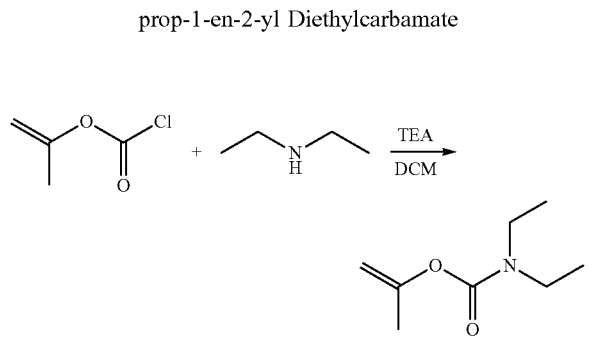

Diethyl amine (1.37 mL, 12.3 mmol, 2.00 equiv) and triethyl amine (2.78 mL, 19.9 mmol, 3.00 equiv) were dissolved in dry DCM (32 mL) and cooled to 0° C. Isopropenyl chloroformate (800 mg, 6.64 mmol, 1.00 equiv) was added dropwise and the reaction mixture was warmed to room temperature. The reaction was allowed to stir overnight. The reaction mixture was quenched with the addition of H₂O, DCM and aqueous layers were separated. The aqueous layer also further extract with 2×30 mL DCM. The organics were combined and dried over MgSO₄, filtered, and concentrated via rotary evaporation. Purification by flash column chromatography (5% ethyl acetate/hexane) afforded the title compound as colorless oil (950 mg, 91% yield).

3-bromoprop-1-en-2-yl Diethylcarbamate

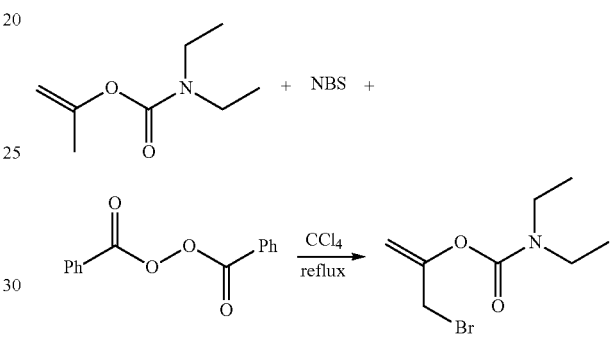

NBS (N-Bromosuccinimide)(543 mg, 3.06 mmol, 1.20 equiv), prop-1-en-2-yl diethylcarbamate (401 mg, 2.54 mmol, 1.00 equiv) and benzoyl peroxide (61.5 mg, 0.254 mmol, 0.100 equiv) were refluxed in dry CCl₄ (24 mL) overnight. The reaction was quenched with brine, and the aqueous layer was extract with 2×20 mL ethyl acetate. The organics were combined and dried over MgSO₄, filtered, and concentrated via rotary evaporation. Purification by flash column chromatography (5% ethyl acetate/hexane) afforded the title compound as colorless oil (179 mg, 30% yield).

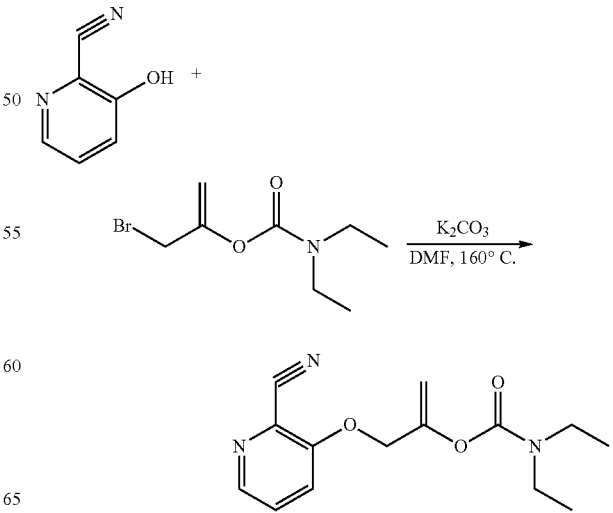

A DMF solution of 3-hydroxypicolinonitrile (281 mg, 2.34 mmol, 2.00 equiv), 3-bromoprop-1-en-2-yl diethylcarbamate (277 mg, 1.17 mmol, 1.00 equiv.) and $K_2CO_3$ (970 mg, 7.02 mmol, 6.00 equiv) was refluxed at 160° C. for 15 hours. DMF was removed via a high vacuum rotary evaporator. The mixture was diluted with 20 mL Brine solution and extract with 20 mL ethyl acetate for three times. The organic layers were combined and dried over $MgSO_4$. Purification by flash chromatography (20%-30% ethyl acetate/hexane) gave 3-((2-cyanopyridin-3-yl)oxy)prop-1-en-2-yl diethylcarbamate (123 mg, 38%) as a yellow oil.

3-((2-(6-(pyridin-2-yl)-1,4-dihydro-1,2,4,5-tetrazin-3-yl)pyridin-3-yl)oxy)prop-1-en-2-yl Diethylcarbamate

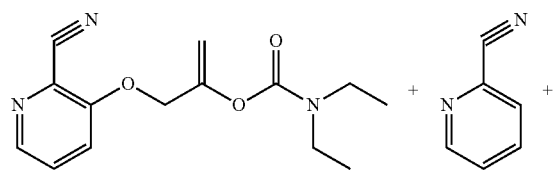

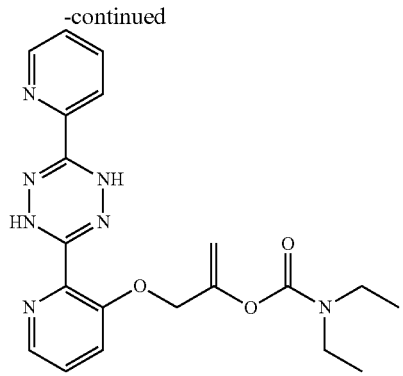

A 10 mL single neck round-bottom flask was charged with 3-((2-cyanopyridin-3-yl)oxy)prop-1-en-2-yl diethylcarbamate (64.0 mg, 0.232 mmol, 1.00 equiv). In a separate flask, 2-cyanopyridine (0.67 µl, 0.697 mmol, 3.00 equiv) was melted by gentle warming, and added to the flask containing 3-((2-cyanopyridin-3-yl)oxy)prop-1-en-2-yl diethylcarbamate. Hydrazine hydrate (113 µl, 2.32 mmol, 10.0 equiv) was added, and the flask was fitted with reflux condenser and heated to 90° C. overnight under $N_2$. The reaction mixture was cooled to r.t. and 10 mL Brine was added. The aqueous layer was extracted with 3×10 mL ethyl acetate. The organics were combined and dried over $MgSO_4$, filtered, and concentrated via rotary evaporation. Purification by flash column chromatography (10%-15% acetone/hexane) afforded the title compound as yellow oil (14.1 mg, 15% yield).

$FeCl_2$ Catalyzed Oxidation of a Dihydrotetrazine in the Presence of $H_2O_2$

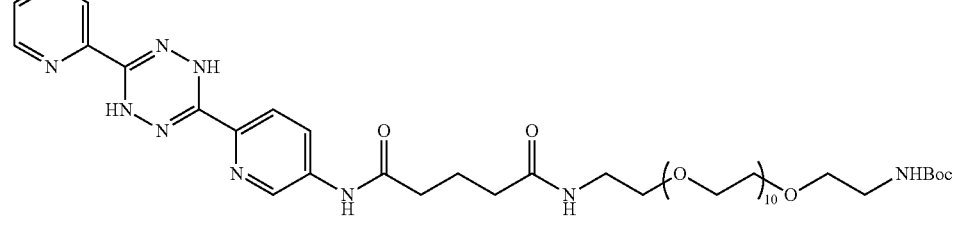

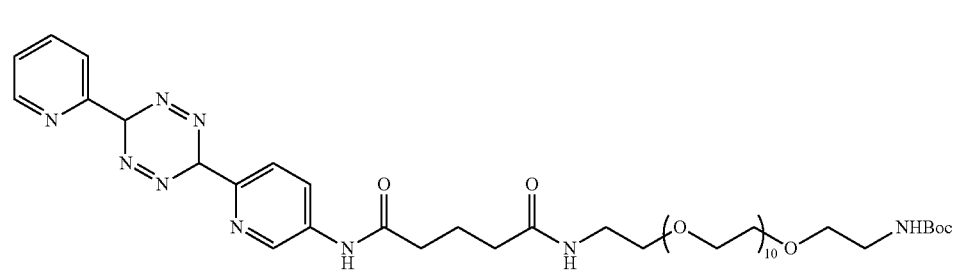

N'-Boc PEG$_{10}$ dipyridyl-dihydrotetrazine was dissolved in deionized water containing 1 mM H$_2$O$_2$ to give a final DHTz concentration of 100 μM. The UV absorbance at 330 nm wavelength was monitored over 10 min. Then a 5 mM FeCl$_2$ stock solution was added and mixed quickly to get a final FeCl$_2$ concentration of 0.05 mM., followed by continuous monitoring of UV absorbance at 330 nm over 10 min. Oxidation was rapid and complete within ~1 minute.

3-(methylamino)picolinonitrile

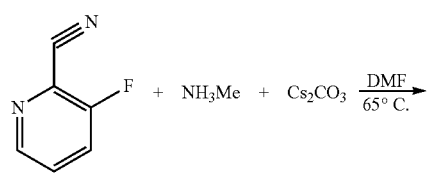

To a solution of 2-cyano-3-fluoropyridine (200 mg, 1.64 mmol, 1.00 equiv) in 5.12 mL DMF were added cesium carbonate (640 mg, 1.97 mmol, 1.20 equiv.) and methylamine (1.97 mL, 3.94 mmol, 2.0M in THF, 2.4 equiv.). The reaction mixture was stirred at 65° C. overnight. After the reaction, DMF was removed via a high vacuum rotary evaporator. The mixture was diluted with 15 mL Brine solution and extract with 15 mL ethyl acetate for three times. The organic layers were combined and dried over MgSO$_4$. Purification by flash chromatography (35% EA/Hexane) gave 3-(methylamino)picolinonitrile (211 mg, 97%) as a white solid.

6-(6-(3-(methylamino)pyridin-2-yl)-1,4-dihydro-1,2,4,5-tetrazin-3-yl)pyridin-3-ol To a 25 mL round bottom flask, 5-hydroxypicolinonitrile (565 mg, 4.70 mmol, 3.00 equiv.), 3-(methylamino)picolinonitrile (206 mg, 1.57 mmol, 1.00 equiv.) and hydrazine monohydrate (1.54 mL, 31.4 mmol, 20.0 equiv.) were added. The reaction mixture was stirred at 90° C. for 24 hours. After the reaction, 20 mL Brine and 20 mL ethyl acetate were added to the mixture. The aqueous layer was extract with 20 mL ethyl acetate for three times. The organic layers were combined, dried over MgSO$_4$ and concentrated. Purification by flash chromatography (30%-45% EA/Hexane) gave 6-(6-(3-(methylamino)pyridin-2-yl)-1,4-dihydro-1,2,4,5-tetrazin-3-yl)pyridin-3-ol (125 mg, 29%) as a yellow solid.

2-(6-(5-(2,5,8,11,14,17,20,23-octaoxapentacosan-25-yloxy)pyridin-2-yl)-1,4-dihydro-1,2,4,5-tetrazin-3-yl)-N-methylpyridin-3-amine

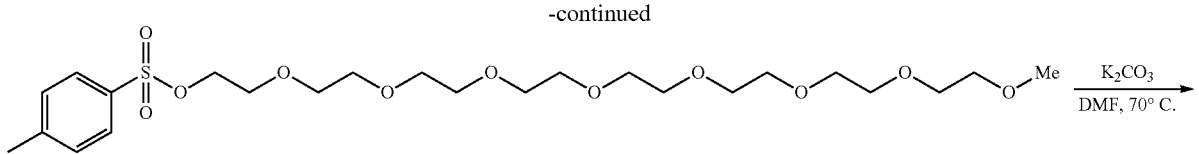

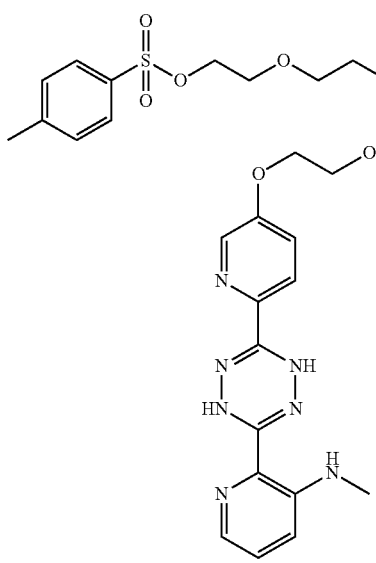

To a DMF (0.700 mL) solution of 6-(6-(3-(methylamino) pyridin-2-yl)-1,4-dihydro-1,2,4,5-tetrazin-3-yl)pyridin-3-ol (20.0 mg, 0.0706 mmol, 1.00 equiv.) and methyl-PEG9-toslate (57.0 mg, 0.106 mmol, 1.50 equiv.) was added potassium carbonate (19.6 mg, 0.142 mmol, 2.00 equiv). The reaction was stirred at 70° C. for 2 hours. After the reaction, DMF was removed via a high vacuum rotary evaporator. The mixture was diluted with 10 mL Brine solution and extract with 10 mL ethyl acetate for three times. The organic layers were combined and dried over MgSO$_4$. Purification by flash chromatography (1% methanol/DCM) gave 2-(6-(5-(2,5,8,11,14,17,20,23-octaoxapentacosan-25-yloxy)pyridin-2-yl)-1,4-dihydro-1,2,4,5-tetrazin-3-yl)-N-methylpyridin-3-amine (27.5 mg, 60%) as a yellow oil.

(E)-N-(2-(6-(5-(2,5,8,11,14,17,20,23-octaoxapenta-cosan-25-yloxy)pyridin-2-yl)-1,4-dihydro-1,2,4,5-tetrazin-3-yl)pyridin-3-yl)-3-(4-(bis(2-chloroethyl)amino)phenoxy)-N-methylacrylamide

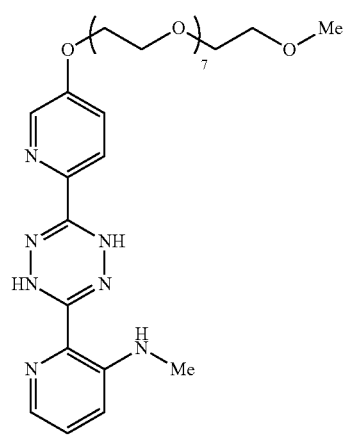

+

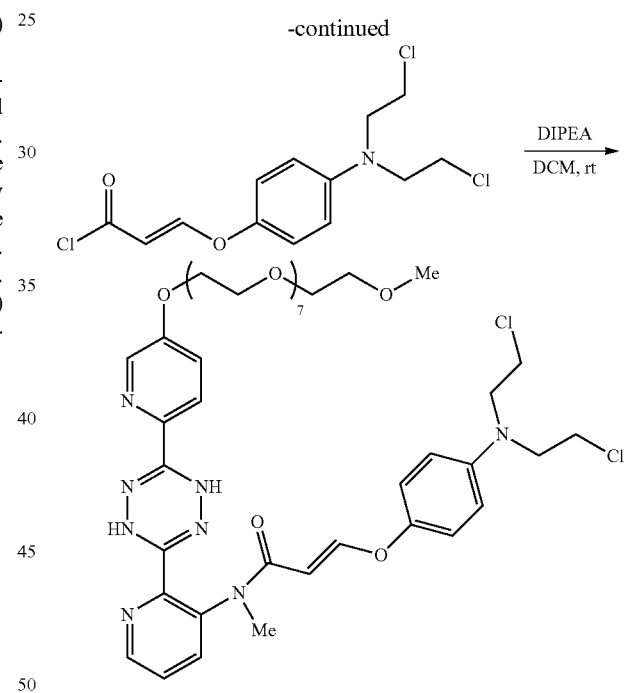

To a flame-dried 10 mL flask containing (E)-3-(4-(bis(2-chloroethyl)amino)phenoxy)acryloyl chloride (52.0 mg, 0.160 mmol, 3.00 equiv.), a dry DCM (0.530 mL) solution of 2-(6-(5-(2,5,8,11,14,17,20,23-octaoxapentacosan-25-yloxy)pyridin-2-yl)-1,4-dihydro-1,2,4,5-tetrazin-3-yl)-N-methylpyridin-3-amine (34.6 mg, 0.0530 mmol, 1.00 equiv.) and DIPEA (41.3 mg, 0.32 mmol, 6.00 equiv.) was added. The reaction mixture was stirred at room temperature for 3 hours. After the reaction, DCM was removed via rotary evaporator. Purification by flash chromatography (40%-60% acetone/hexane) gave (E)-N-(2-(6-(5-(2,5,8,11,14,17,20,23-octaoxapentacosan-25-yloxy)pyridin-2-yl)-1,4-dihydro-1,2,4,5-tetrazin-3-yl)pyridin-3-yl)-3-(4-(bis(2-chloroethyl)amino)phenoxy)-N-methylacrylamide (18.2 mg, 37%) as a yellow oil.

3-(5-(2,5,8,11,14,17,20,23-octaoxapentacosan-25-yloxy)pyridin-2-yl)-6-methylpyridazino[4,3-c][1,5]naphthyridin-5(6H)-one

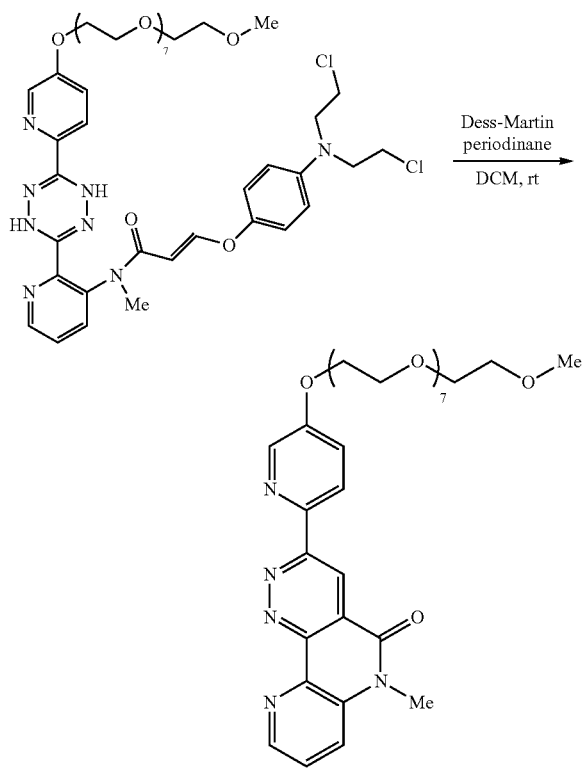

To a dry DCM (1.00 mL) solution of (E)-N-(2-(6-(5-(2,5,8,11,14,17,20,23-octaoxapentacosan-25-yloxy)pyridin-2-yl)-1,4-dihydro-1,2,4,5-tetrazin-3-yl)pyridin-3-yl)-3-(4-(bis(2-chloroethyl)amino)phenoxy)-N-methylacrylamide (11.1 mg, 0.0119 mmol, 1.00 equiv.) was added Dess-Martin periodinane (10.3 mg, 0.0242 mmol, 2.00 equiv). The reaction mixture was stirred at room temperature for 1 hour. After reaction, DCM was removed via rotary evaporator. Purification by flash chromatography (50% acetone/hexane, then 5% methanol/dcm) gave 3-(5-(2,5,8,11,14,17,20,23-octaoxapentacosan-25-yloxy)pyridin-2-yl)-6-methylpyridazino[4,3-c][1,5]naphthyridin-5(6H)-one (4.6 mg, 58%) as a yellow oil.

4-(bis(2-chloroethyl)amino)phenol

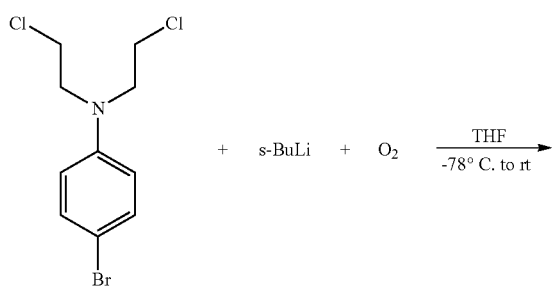

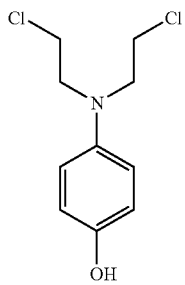

4-Bromo-N,N-bis(2-chloroethyl)aniline was prepared from ((4-bromophenyl)azanediyl)bis(ethane-2,1-diyl) dimethanesulfonate following the procedure previously described (*J. Med. Chem.* 2014, 4498). 4-Bromo-N,N-bis(2-chloroethyl)aniline (200 mg, 0.670 mmol, 1.00 equiv.) was dissolved in 6.70 mL dry THF. The solution was chilled to −78 C. After 10 min, 1.00 mL s-BuLi (1.35 mmol, 2.00 equiv, 1.40 M in cyclohexane) was added to the THF solution dropwise. The reaction was stirred at −78° C. for 20 min. Oxygen was then sparged into the reaction solution for 30 min at −78° C. Oxygen was sparged for another 30 min, during which time the reaction was allowed to warm up to 0° C. The reaction mixture was then stirred at room temperature for one hour. After the reaction, THF was removed via rotary evaporator. The mixture was diluted with 20 mL Brine and 20 mL ethyl acetate. The aqueous layer was extract with 20 mL ethyl acetate for three times. The organic layers were combined, dried over MgSO$_4$ and concentrated. Purification by flash chromatography (10%-15% ethyl acetate/hexane) gave 4-(bis(2-chloroethyl)amino)phenol (55.0 mg, 35%) as a colorless oil.

(E)-methyl 3-(4-(bis(2-chloroethyl)amino)phenoxy)acrylate

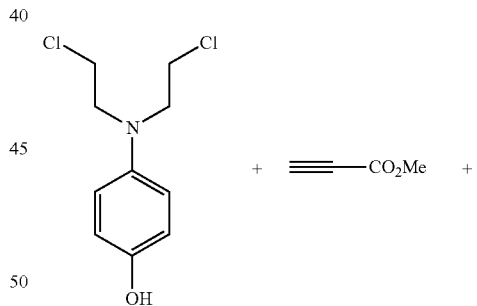

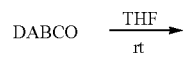

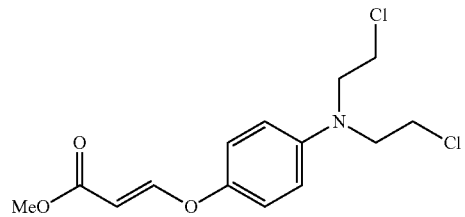

To a stirred solution of 1,4 diazabicyclo[2,2,2] octane (12.8 mg, 0.114 mmol, 0.100 equiv.) and 4-(bis(2-chloroethyl)amino)phenol (265 mg, 1.14 mmol, 1.00 equiv.) in 0.700 mL dry THF at room temperature was added methyl propiolate (111 μl, 1.25 mmol, 1.10 equiv) dropwise. The reaction mixture was stirred overnight at room temperature. After reaction, THF was removed via rotary evaporator. Sodium hydroxide (10% solution, 10 mL) was added and the aqueous was extracted with 10 mL DCM for three times. The organic layers were combined, dried over MgSO₄, and concentrated. Purification by flash chromatography (5%-10% ethyl acetate/hexane) gave (E)-methyl 3-(4-(bis(2-chloroethyl)amino)phenoxy)acrylate (276 mg, 76%) as a white solid.

(E)-3-(4-(bis(2-chloroethyl)amino)phenoxy)acrylic Acid

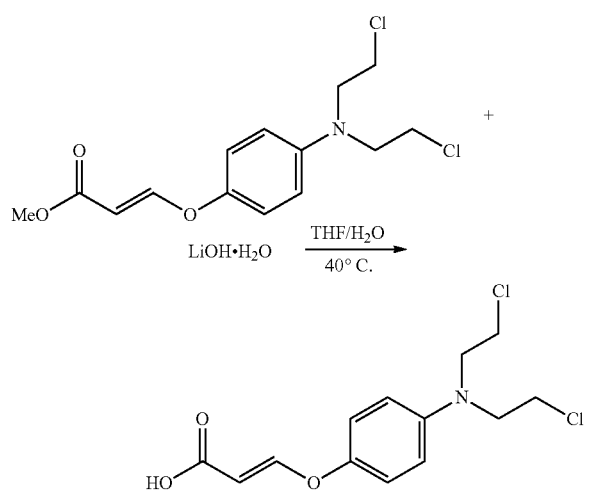

LiOH·H₂O (80.0 mg, 1.91 mmol, 2.00 equiv.) was added to 10.4 mL THF/H₂O (3:1) solution of (E)-methyl 3-(4-(bis(2-chloroethyl)amino)phenoxy)acrylate (304 mg, 0.950 mmol, 1.00 equiv.). The reaction was stirred at 40° C. for 72 hours. After reaction, the solution was neutralized to pH=7 with 1.0 M HCl. The mixture was diluted with 20 mL Brine and 20 mL ethyl acetate. The aqueous layer was extract with 20 mL ethyl acetate for three times. The organic layers were combined, dried over MgSO₄ and concentrated. Purification by flash chromatography (30% ethyl acetate/hexane) gave (E)-3-(4-(bis(2-chloroethyl)amino)phenoxy)acrylic acid (154 mg, 50%) as a colorless solid.

(E)-3-(4-(bis(2-chloroethyl)amino)phenoxy)acryloyl Chloride

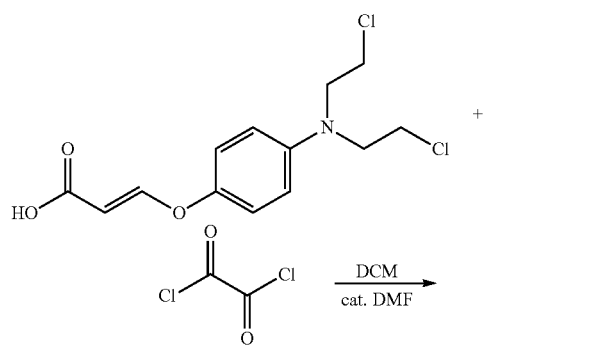

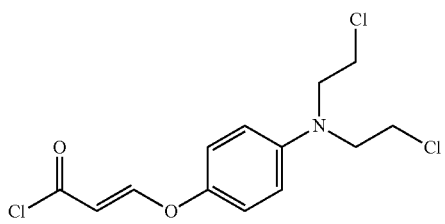

To a dry DCM (11.53 mL) solution of (E)-3-(4-(bis(2-chloroethyl)amino)phenoxy)acrylic acid (141 mg, 0.460 mmol, 1.00 equiv.) was added oxalyl chloride (59.0 μl, 0.700 mmol, 1.50 equiv.) at 0° C. One drop of dry DMF was added to the reaction mixture. The reaction was stirred at room temperature for 1.5 hours. After reaction, the mixture was concentrated via rotary evaporator to give (E)-3-(4-(bis(2-chloroethyl)amino)phenoxy)acryloyl chloride (236 mg, 90%) as a pale green solid, which was used in the next step without further purification.

3-(butylamino)picolinonitrile

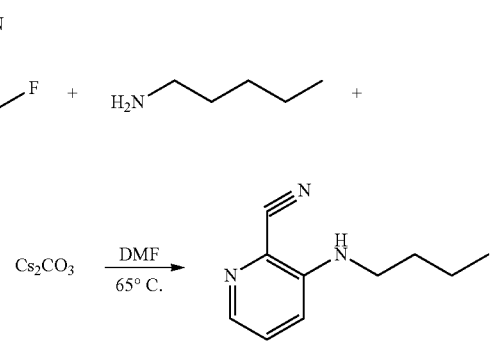

To a solution of 2-cyano-3-fluoropyridine (200 mg, 1.64 mmol, 1.00 equiv) in 5.10 mL DMF were added cesium carbonate (640 mg, 1.97 mmol, 1.20 equiv.) and butylamine (0.195 mL, 1.97 mmol, 1.20 equiv.). The reaction mixture was stirred at 65° C. overnight. After the reaction, DMF was removed via a high vacuum rotary evaporator. The mixture was diluted with 15 mL Brine solution and extract with 15 mL ethyl acetate for three times. The organic layers were combined and dried over MgSO₄. Purification by flash chromatography (20% EA/Hexane) gave 3-(butylamino)picolinonitrile (257 mg, 90%) as a colorless oil.

N-butyl-2-(6-(pyridin-2-yl)-1,4-dihydro-1,2,4,5-tetrazin-3-yl)pyridin-3-amine

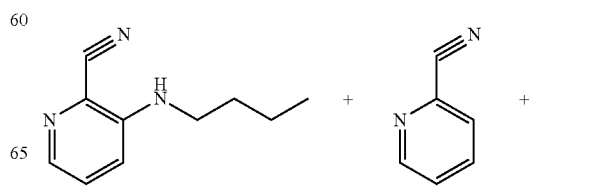

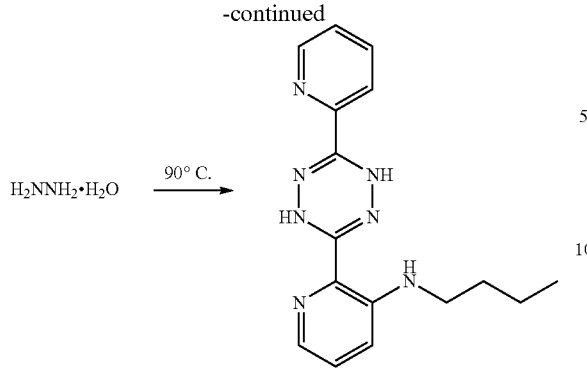

To a 25 mL round bottom flask, 3-(butylamino)picolinonitrile (200 mg, 1.14 mmol, 1.00 equiv.), picolinonitrile (297 mg, 2.85 mmol, 2.50 equiv.) and hydrazine monohydrate (0.445 mL 9.13 mmol, 8.00 equiv.) were added. The reaction mixture was stirred at 90° C. for 24 hours. After the reaction, 10 mL Brine and 10 mL ethyl acetate were added to the mixture. The aqueous layer was extract with 10 mL ethyl acetate for four times. The organic layers were combined, dried over MgSO$_4$ and concentrated. Purification by flash chromatography (5%-10% EA/Hexane) gave N-butyl-2-(6-(pyridin-2-yl)-1,4-dihydro-1,2,4,5-tetrazin-3-yl)pyridin-3-amine (64.8 mg, 17%) as a yellow solid.

(E)-methyl 3-(4-nitrophenoxy)acrylate

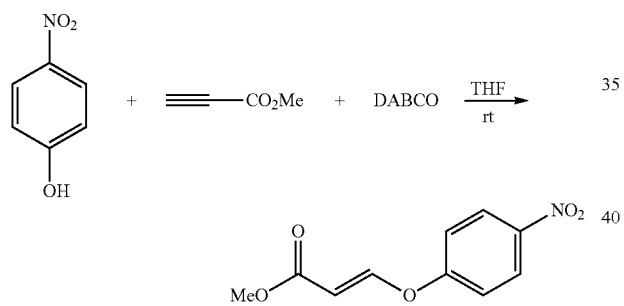

To a stirred solution of 1,4 diazabicyclo[2,2,2] octane (269 mg, 2.40 mmol, 0.100 equiv.) and 4-nitrophenol (3.62 g, 26.0 mmol, 1.10 equiv.) in 15 mL dry THF at room temperature was added methyl propiolate (2.14 mL, 24.0 mmol, 1.00 equiv) dropwise. The reaction mixture was stirred overnight at room temperature. After reaction, THF was removed via rotary evaporator. Sodium hydroxide (10% solution, 100 mL) was added and the aqueous was extracted with 100 mL DCM for three times. The organic layers were combined, dried over MgSO$_4$, and concentrated. Purification by flash chromatography (5%-10% ethyl acetate/hexane) gave (E)-methyl 3-(4-nitrophenoxy)acrylate (4.82 g, 90%) as a white solid.

(E)-3-(4-nitrophenoxy)acrylic Acid

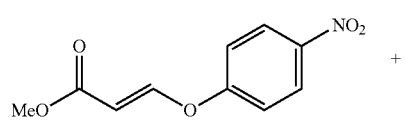

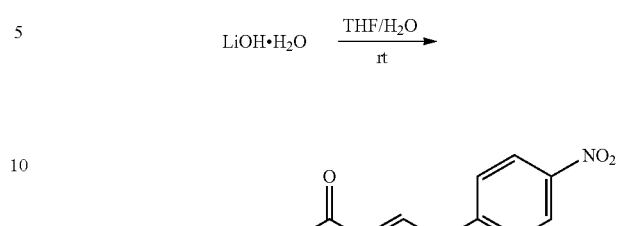

LIOH.H$_2$O (2.10 g, 50.0 mmol, 2.00 equiv.) was added to 272 mL THF/H$_2$O (3:1) solution of (E)-methyl 3-(4-nitrophenoxy)acrylate (5.78 g, 25.0 mmol, 1.00 equiv.). The reaction was stirred at room temperature overnight. After reaction, the solution was acidified to pH=3.0 with 1.0 M HCl. The mixture was diluted with 100 mL Brine and 100 mL ethyl acetate. The aqueous layer was extract with 100 mL diethyl ether for three times. The organic layers were combined, dried over MgSO$_4$ and concentrated. Purification by flash chromatography (1% methanol/dcm) gave (E)-3-(4-(bis(2-chloroethyl)amino)phenoxy)acrylic acid (4.90 g, 90%) as a white solid.

(E)-3-(4-nitrophenoxy)acryloyl Chloride

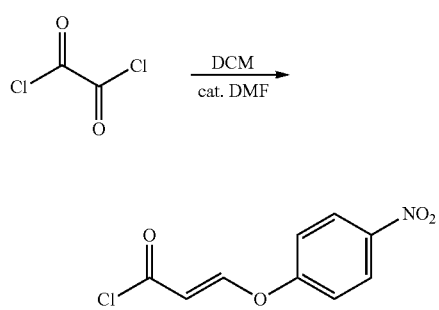

To a dry DCM (4.70 mL) solution of (E)-3-(4-(bis(2-chloroethyl)amino)phenoxy)acrylic acid (300 mg, 1.43 mmol, 1.00 equiv.) was added oxalyl chloride (0.388 mL, 4.59 mmol, 3.20 equiv.) at 0° C. One drop of dry DMF was added to the reaction mixture. The reaction was stirred at room temperature for 4 hours. After reaction, the mixture was concentrated via rotary evaporator to give (E)-3-(4-nitrophenoxy)acryloyl chloride (300 mg, 92%) as a pale yellow solid, which was used in the next step without further purification.

53

(E)-N-butyl-3-(4-nitrophenoxy)-N-(2-(6-(pyridin-2-yl)-1,4-dihydro-1,2,4,5-tetrazin-3-yl)pyridin-3-yl)acrylamide

54

6-butyl-3-(pyridin-2-yl)pyridazino[4,3-c][1,5]naphthyridin-5(6H)-one

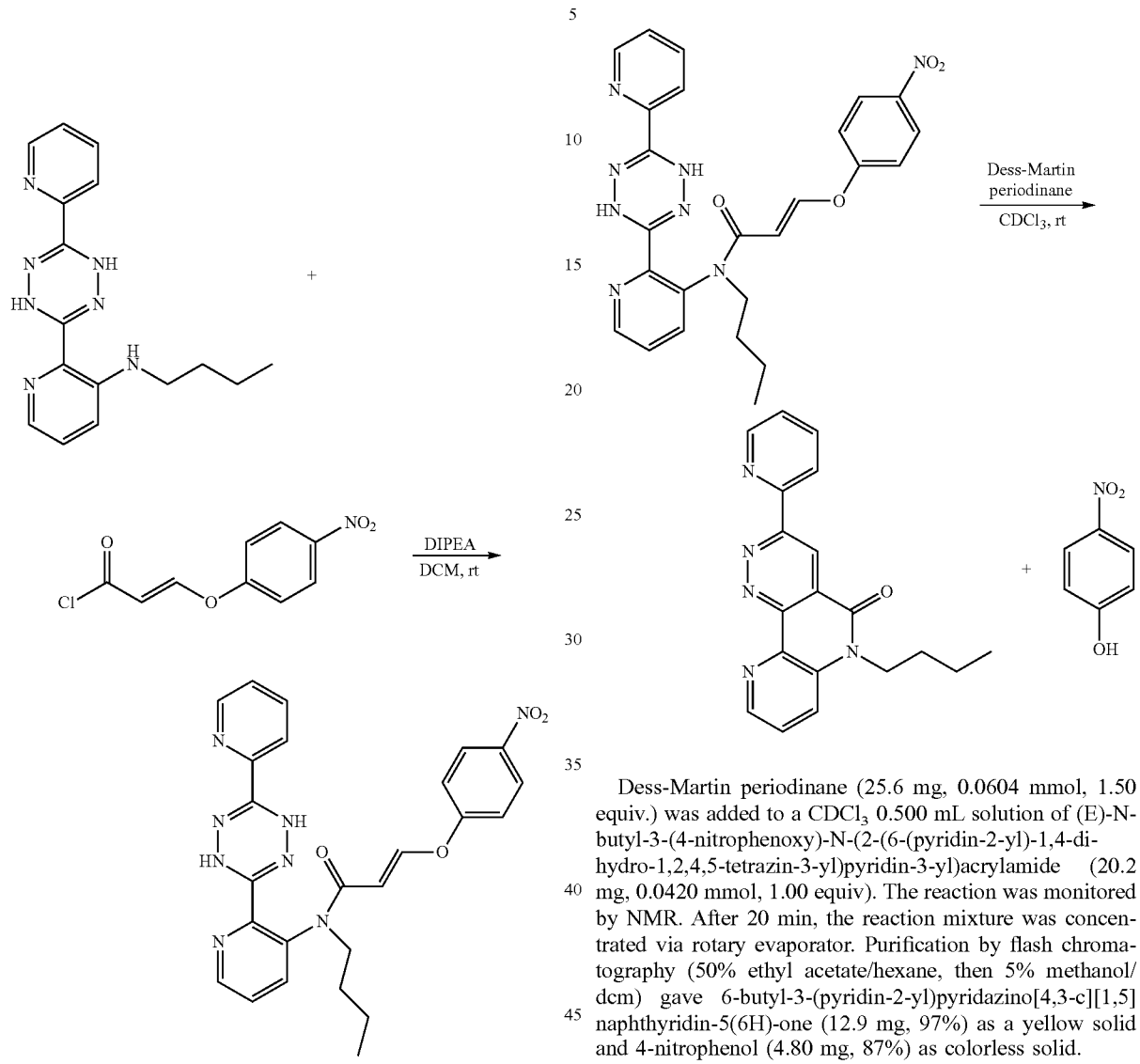

A 10 mL flame-dried flask was charged with (E)-3-(4-nitrophenoxy)acryloyl chloride (100 mg, 0.440 mmol, 2.44 equiv.). A 0.800 mL DCM (dry) solution of N-butyl-2-(6-(pyridin-2-yl)-1,4-dihydro-1,2,4,5-tetrazin-3-yl)pyridin-3-amine (55.0 mg, 0.180 mmol, 1.00 equiv) was added to the flask in one portion, followed by DIPEA (62.5 µl, 0.376 mmol, 2.09 equiv.). The reaction was stirred at room temperature overnight. The reaction was quenched by 10 mL NaHCO₃ (sat.) and 10 mL ethyl acetate. The aqueous layer was extract with 10 mL ethyl acetate for three times. The organic layers were combined, dried over MgSO₄ and concentrated. Purification by flash chromatography (15%-30% ethyl acetate/hexane) gave (E)-N-butyl-3-(4-nitrophenoxy)-N-(2-(6-(pyridin-2-yl)-1,4-dihydro-1,2,4,5-tetrazin-3-yl)pyridin-3-yl)acrylamide (20.2 mg, 22%) as a yellow solid.

Dess-Martin periodinane (25.6 mg, 0.0604 mmol, 1.50 equiv.) was added to a CDCl₃ 0.500 mL solution of (E)-N-butyl-3-(4-nitrophenoxy)-N-(2-(6-(pyridin-2-yl)-1,4-dihydro-1,2,4,5-tetrazin-3-yl)pyridin-3-yl)acrylamide (20.2 mg, 0.0420 mmol, 1.00 equiv). The reaction was monitored by NMR. After 20 min, the reaction mixture was concentrated via rotary evaporator. Purification by flash chromatography (50% ethyl acetate/hexane, then 5% methanol/dcm) gave 6-butyl-3-(pyridin-2-yl)pyridazino[4,3-c][1,5]naphthyridin-5(6H)-one (12.9 mg, 97%) as a yellow solid and 4-nitrophenol (4.80 mg, 87%) as colorless solid.

3-((2-hydroxyethyl)amino)picolinonitrile

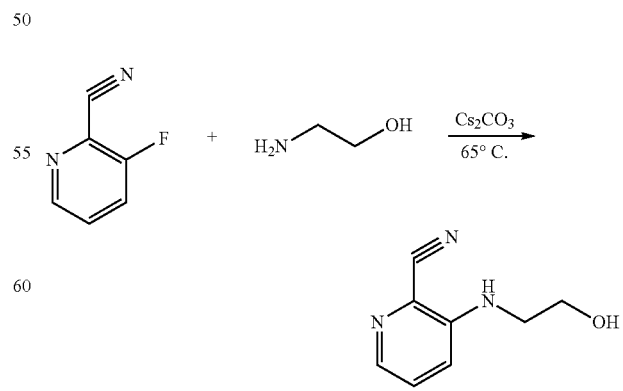

To a solution of 2-cyano-3-fluoropyridine (500 mg, 4.10 mmol, 1.00 equiv) in 12.8 mL DMF were added cesium carbonate (1.60 g, 4.91 mmol, 1.20 equiv.) and ethanolamine (0.295 mL, 4.91 mmol, 1.20 equiv.). The reaction mixture was stirred at 65° C. for 8 hours. After the reaction, DMF was removed via a high vacuum rotary evaporator. The mixture was diluted with 15 mL Brine solution and extract with 15 mL ethyl acetate for three times. The organic layers were combined and dried over MgSO$_4$. Purification by flash chromatography (1%-5% methanol/dcm) gave 3-((2-hydroxyethyl)amino)picolinonitrile (177 mg, 27%) as a white solid.

2-((2-(6-(pyridin-2-yl)-1,4-dihydro-1,2,4,5-tetrazin-3-yl)pyridin-3-yl)amino)ethanol

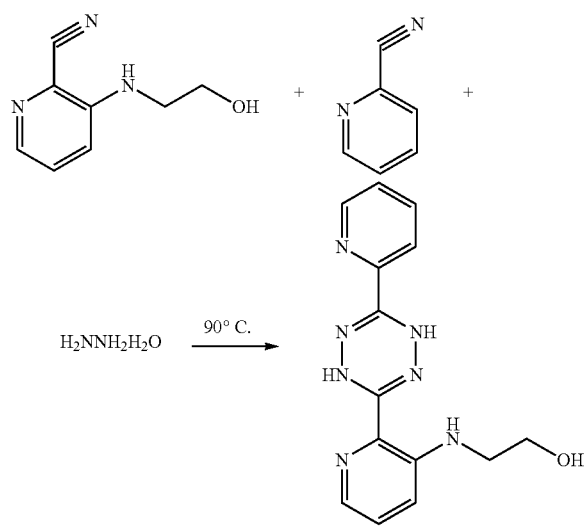

To a 25 mL round bottom flask, 3-((2-hydroxyethyl)amino)picolinonitrile (500 mg, 3.06 mmol, 1.00 equiv.), picolinonitrile (957 mg, 9.19 mmol, 3.00 equiv.) and hydrazine monohydrate (1.50 mL, 30.6 mmol, 10.0 equiv.) were added. The reaction mixture was stirred at 90° C. for overnight. After the reaction, 30 mL Brine and 30 mL ethyl acetate were added to the mixture. The aqueous layer was extract with 30 mL ethyl acetate for four times. The organic layers were combined, dried over MgSO$_4$ and concentrated. Purification by flash chromatography (15%-50% ethyl acetate/hexane) gave 2-((2-(6-(pyridin-2-yl)-1,4-dihydro-1,2,4,5-tetrazin-3-yl)pyridin-3-yl)amino)ethanol (339 mg, 37%) as a yellow solid.

4-nitrophenyl (2-((2-(6-(pyridin-2-yl)-1,4-dihydro-1,2,4,5-tetrazin-3-yl)pyridin-3-yl)amino)ethyl) Carbonate

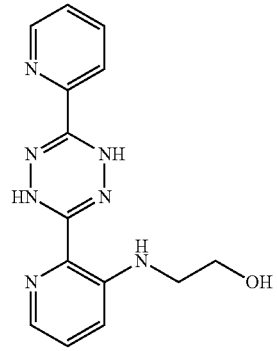

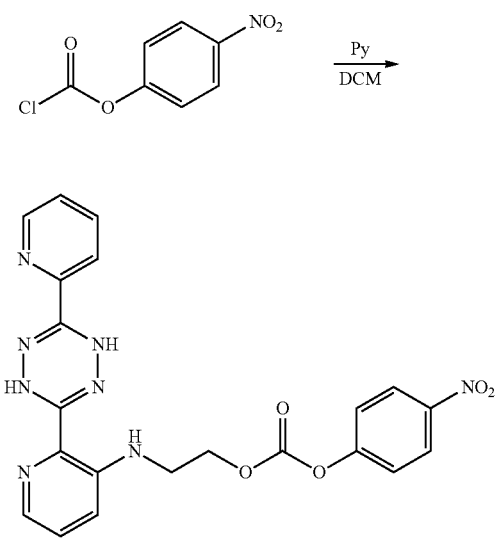

To a DCM (2.20 mL, dry) solution of pyridine (35.3 mg, 0.446 mmol, 2.00 equiv) and 2-((2-(6-(pyridin-2-yl)-1,4-dihydro-1,2,4,5-tetrazin-3-yl)pyridin-3-yl)amino)ethanol (66.3 mg, 0.223 mmol, 1.00 equiv) was added 4-nitrophenyl chloroformate (49.4 mg, 0.245 mmol, 1.10 equiv.) at room temperature. The reaction was stirred at room temperature for 1 hour. The reaction was then quenched with 10 mL Brine and 10 mL DCM. The aqueous layer was extract with 10 mL DCM for three times. The organic layers were combined, dried over MgSO$_4$ and concentrated. Purification by flash chromatography (10%-30% ethyl acetate/hexane) gave 4-nitrophenyl (2-((2-(6-(pyridin-2-yl)-1,4-dihydro-1,2,4,5-tetrazin-3-yl)pyridin-3-yl)amino)ethyl) carbonate (47.6 mg, 46%) as a yellow solid.

2-((2-(6-(pyridin-2-yl)-1,4-dihydro-1,2,4,5-tetrazin-3-yl)pyridin-3-yl)amino)ethyl 2,5,8,11,14,17,20,23,26,29,32,35-dodecaoxaheptatriacontan-37-ylcarbamate

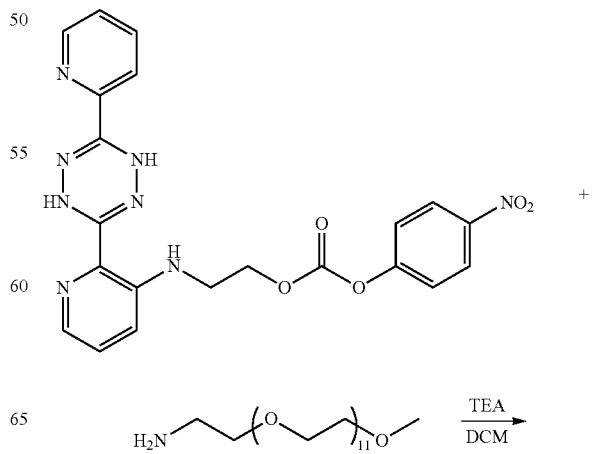

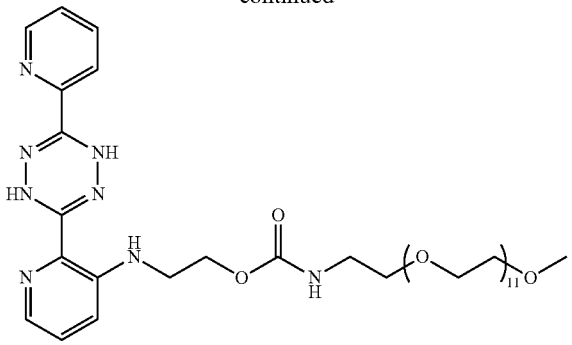

To a DCM (0.50 mL, dry) solution of methyl-PEG11-amine (29.5 mg, 0.0500 mmol, 1.10 equiv) and 4-nitrophenyl (2-((2-(6-(pyridin-2-yl)-1,4-dihydro-1,2,4,5-tetrazin-3-yl)pyridin-3-yl)amino)ethyl) carbonate (21.1 mg, 0.0450 mmol, 1.00 equiv) was triethylamine (9.10 mg, 0.0900 mmol, 2.00 equiv) at room temperature. The reaction was stirred at room temperature for 3 hours. The reaction was then concentrated via rotary evaporator. Purification by flash chromatography (1%-5% methanol/dcm) gave 2-((2-(6-(pyridin-2-yl)-1,4-dihydro-1,2,4,5-tetrazin-3-yl)pyridin-3-yl)amino)ethyl 2,5,8,11,14,17,20,23,26,29,32,35-dodecaoxaheptatriacontan-37-ylcarbamate (31.0 mg, 77%) as a yellow oil.

3-((2-cyanopyridin-3-yl)oxy)prop-1-en-2-yl diethylcarbamate 2-pyridinecarboxylic Acid Hydrazide

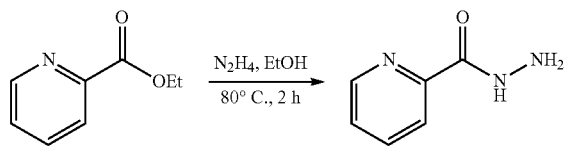 [SMILES: CCOC(=O)c1ccccn1 ; NNC(=O)c1ccccn1]

To a round-bottom flask was added ethyl picolinate (2.5 mL, 18.52 mmol) in ethanol (12 mL) followed by hydrazine monohydrate (1.74 mL, 55.56 mmol). The mixture was refluxed for 2 h. Ethanol was evaporated after reaction mixture cooled down. The light yellow crude product was washed with diethyl ether (15 mL×2). Final product as a white solid (2.3 g, 90%) was collected by vacuum filtration and dried under vacuum. $^1$H NMR (600 MHz, CDCl$_3$) 9.00 (s, 1H), 8.57-8.53 (m, 1H), 8.15 (dd, J=7.8, 1.2 Hz, 1H), 7.85 (td, J=7.7, 1.7 Hz, 1H), 7.44 (ddd, J=7.8, 4.8, 1.2 Hz, 1H), 4.09 (s, 2H); $^{13}$C NMR (100 MHz, CDCl$_3$) 164.84, 149.17, 148.51, 137.47, 126.61, 122.36

N-(carbethoxycarbonyloxy)succinimide

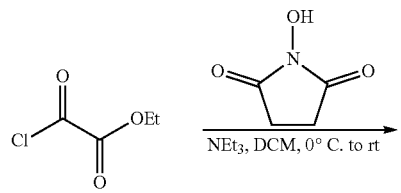

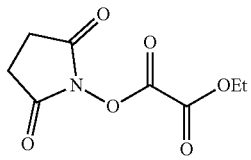

To a dry round-bottom flask was added N-hydroxysuccinimide (2.67 g, 23.27 mmol), anhydrous dichloromethane (10 mL) and trimethylamine (3.24 mL, 23.27 mmol). The mixture was stirred in ice bath for 10 min. Ethyl chlorooxoacetate (2 mL, 17.90 mmol) in anhydrous dichloromethane (20 mL) was added dropwise via syringe pump at 0° C. in 30 min. The mixture was stirred at 0° C. for 30 min, room temperature for 1 h, diluted by dichloromethane (30 mL) and washed by water (20 mL*3). The organic layer was dried with MgSO$_4$, filtered and then solvent was evaporated by rotary evaporator. Crude product (2.85 g, 74%) as light yellow solid was used in the next step without further purification. $^1$H NMR (600 MHz, CDCl$_3$) 4.46 (q, J=7.2 Hz, 1H), 2.90 (s, 2H), 1.43 (t, J=7.2 Hz, 1H); $^{13}$C NMR (100 MHz, CDCl$_3$) 167.89, 154.24, 153.00, 64.76, 25.79, 14.00

Ethyl 2-oxo-2-(2-picolinoylhydrazinyl)acetate

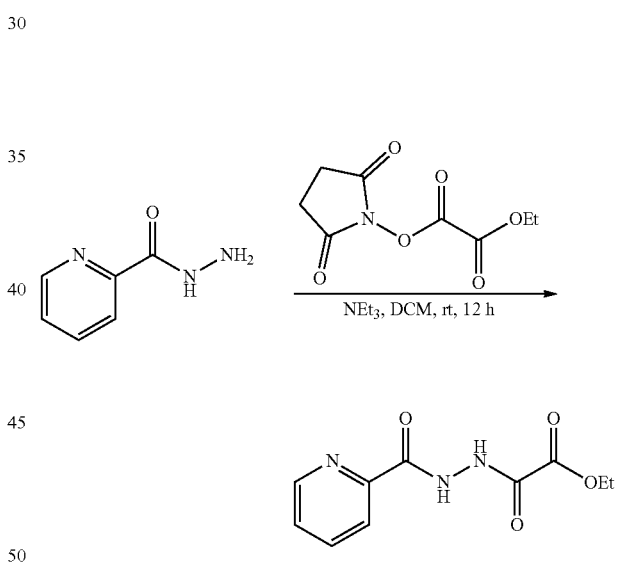

To a dry round-bottom flask was added 2-pyridinecarboxylic acid hydrazide (1.68 g, 12.24 mmol), N-(carbethoxycarbonyloxy)succinimide (2.64 g, 12.24 mmol), triethylamine (2.1 mL, 14.68 mmol) and anhydrous dichloromethane (30 mL). After stirring at room temperature for 12 h, the mixture was diluted by dichloromethane (30 mL) and washed with water (20 mL*3). The organic layer was dried with MgSO$_4$, filtered and evaporated by rotary evaporator. Crude product (2.09 g, 72%) as light yellow solid was used in the next step without further purification. $^1$H NMR (600 MHz, CDCl$_3$) 10.30 (s, 1H), 9.66 (s, 1H), 8.61 (ddd, J=4.8, 1.8, 1.0 Hz, 1H), 8.17 (dt, J=7.9, 1.1 Hz, 1H), 7.89 (td, J=7.7, 1.7 Hz, 1H), 7.51 (ddd, J=7.7, 4.7, 1.2 Hz, 1H), 4.42 (q, J=7.2 Hz, 2H), 1.42 (t, J=7.2 Hz, 3H); $^{13}$C NMR (100 MHz, CDCl$_3$) 160.73, 158.89, 152.58, 148.79, 147.77, 137.64, 127.33, 122.81, 63.78, 14.12

Ethyl 2-chloro-2-((chloro(phenyl)methylene)hydrazono)acetate

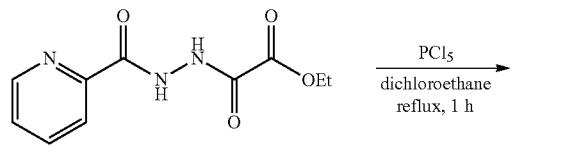

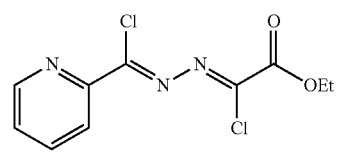

To a dry round-bottom flask was added ethyl 2-oxo-2-(2-picolinoylhydrazinyl)acetate (0.527 g, 2.2 mmol), phosphorous pentachloride (2.3 g, 11.1 mmol) and anhydrous dichloroethane (12 mL). After reflux (85° C.) for 1 h, the mixture was diluted with dichloromethane (50 mL), quenched and washed with cool water (20 mL*3). The organic layer was dried with MgSO₄, filtered and evaporated by rotary evaporator. The orange oil-like product (0.15 g, 25%) was collected from column chromatography eluting with hexane/ethyl acetate (7/3). $^1$H NMR (600 MHz, CDCl₃) 8.77 (ddd, J=4.8, 1.8, 0.9 Hz, 1H), 8.16 (dt, J=8.0, 1.1 Hz, 1H), 7.84 (td, J=7.8, 1.8 Hz, 1H), 7.46 (ddd, J=7.6, 4.8, 1.2 Hz, 1H), 4.47 (q, J=7.2 Hz, 2H), 1.44 (t, J=7.2 Hz, 3H); $^{13}$C NMR (100 MHz, CDCl₃) 158.56, 149.88, 149.84, 142.34, 137.06, 133.74, 126.21, 123.47, 64.28, 14.20

Ethyl 6-(pyridin-2-yl)-1,4-dihydro-1,2,4,5-tetrazine-3-carboxylate

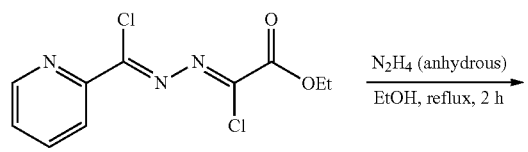

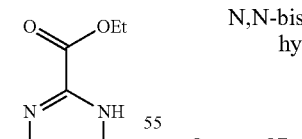

To a dry round-bottom flask was added ethyl 2-chloro-2-((chloro(phenyl)methylene) hydrazono)acetate (0.4 g, 1.46 mmol), anhydrous hydrazine (50 uL, 1.61 mmol) and anhydrous ethanol (6 mL). The mixture was reflux (85° C.) for 2 h and solvent was removed under reduced pressure to yield orange oil like crude product. The crude product was purified by column chromatography loading with dichloromethane and eluting with hexane/ethyl acetate (9/1 to 6/4) to yield yellow solid (0.11 g, 32%). $^1$H NMR (600 MHz, CDCl₃) 8.68 (s, 1H), 8.56 (ddd, J=4.9, 1.7, 0.9 Hz, 1H), 7.99 (dt, J=8.0, 1.1 Hz, 1H), 7.76 (td, J=7.8, 1.7 Hz, 1H), 7.40 (s, 1H), 7.37 (ddd, J=7.5, 4.9, 1.2 Hz, 1H), 4.39 (q, J=7.1 Hz, 2H), 1.40 (t, J=7.1 Hz, 4H); $^{13}$C NMR (100 MHz, CDCl₃) 159.66, 148.72, 146.73, 145.40, 139.97, 137.10, 125.50, 121.78, 63.26, 14.33

Ethyl 6-(pyridin-2-yl)-1,2,4,5-tetrazine-3-carboxylate

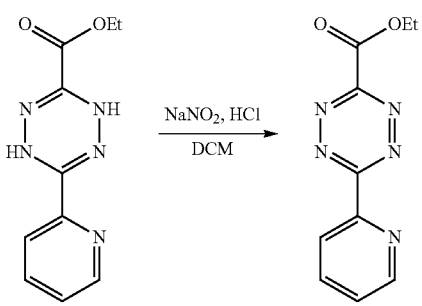 [SMILES: CCOC(=O)C1=NNC(c2ccccn2)=NN1 ; CCOC(=O)c1nnc(-c2ccccn2)nn1]

To a dry round bottom flask was added ethyl 6-(pyridin-2-yl)-1,4-dihydro-1,2,4,5-tetrazine-3-carboxylate (30 mg, 0.129 mmol) and anhydrous dichloromethane (3 mL). To another round bottom flask, connected with the first round bottom flask by needle, was added hydrochloric acid (0.79 mL, 25.73 mmol) and injected nitrogen gas continuously, then sodium nitrite (1.77 g, 25.73 mmol) in water (20 mL) was added by syringe slowly. When pink solution formed in the first round bottom flask, reaction mixture was purified by column chromatography eluting with hexane/ethyl acetate (6/4) to yield pink solid (24 mg, 80.5%). $^1$H NMR (600 MHz, CDCl₃) 9.01 (ddd, J=4.7, 1.8, 0.9 Hz, 1H), 8.77 (dt, J=7.9, 1.1 Hz, 1H), 8.04 (td, J=7.8, 1.8 Hz, 1H), 7.62 (ddd, J=7.6, 4.7, 1.2 Hz, 1H), 4.69 (q, J=7.2 Hz, 2H)M 1.54 (t, J=7.2 Hz, 3H); $^{13}$C NMR (100 MHz, CDCl₃) 164.42, 160.91, 159.09, 151.48, 149.44, 137.78, 127.38, 125.49, 64.08, 14.32

N,N-bis(2-hydroxyethyl)-6-(pyridin-2-yl)-1,4-dihydro-1,2,4,5-tetrazine-3-carboxamide

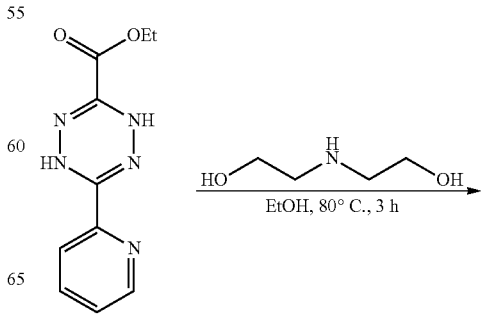

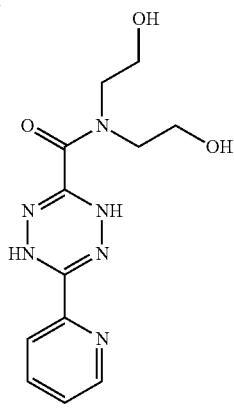

To a dry round bottom flask was added ethyl 6-(pyridin-2-yl)-1,4-dihydro-1,2,4,5-tetrazine-3-carboxylate (29 mg, 0.124 mmol), diethanolamine (36 uL, 0.373 mmol) and anhydrous ethanol (6 mL). After refluxing for 3 h, the mixture was concentrated and purified by column chromatography eluting with dichloromethane/methanol (100/0 to 95/5) to yield yellow oil-like product. $^1$H NMR (600 MHz, CDCl$_3$) 8.58-8.54 (m, 2H), 8.01 (d, J=8.0 Hz, 1H), 7.77 (td, J=7.8, 1.6 Hz, 1H), 7.70 (s, 1H), 7.37 (dd, J=7.5, 4.9 Hz, 1H), 7.26 (s, 1H), 4.15-3.75 (m, 6H), 3.68 (t, J=4.9 Hz, 1H), 1.67 (s, 2H); $^{13}$C NMR (100 MHz, CDCl$_3$) 161.71, 148.55, 146.76, 145.23, 143.31, 137.09, 125.44, 121.80, 60.59, 60.45, 52.35, 52.08

Dihydrotetrazine Oxidation Experiments

General Considerations

UV-Vis measurements were conducted in quartz cuvettes using either a Hewlett Packard 8453 or 8452A spectrophotometer equipped with temperature controlled, stirring cuvette holders. Glassware was cleaned by rinsing twice with phosphate buffered saline (PBS, pH=7.4) containing EDTA (2 mM) followed by triple rinsing with PBS buffer free of EDTA. PBS buffer was prepared by adding the following to Milli-Q purified water: NaCl (8 g/L), KCl (0.2 g/L), Na$_2$HPO$_4$ (1.42 g/L), KH$_2$PO$_4$ (0.24 g/L) and ethylenediaminetetraacetic acid disodium salt (0.672 g/L). The pH of the buffer was then adjusted to 7.4 using either 1M solutions of either HCl or NaOH.

Experiments to study the catalytic photooxidation were conducted at 25° C. in a thermostatted UV-cell with stirring capability and a single top-mounted LED. The LED was mounted in a custom, 3-D printed housing that is displayed below. The wavelength of irradiation was varied by exchanging LED bulbs of variable dominant wavelength (DWL).

The LEDs were manufactured by CREE and had the following specifications.

Photo Red (CREE XPEPHR-L1), 660 nm LED (650-670 DWL, photo red)

Green (CREE XPEGRN-L1), 528 nm LED (520-535 DWL, green)

For LEDs, the light intensity was estimated by measuring the light intensity 4 cm from the light source, which is equal to the distance from the LED to the center of the cuvette holder. To measure the intensity of light emitted by the LEDs an International Light IL1400A instrument equipped with a SEL005 sensor was used. The instrument was calibrated to the peak intensity of the LED. All measurements were conducted in a dark room.

Methylene Blue Catalyzed Photooxidation

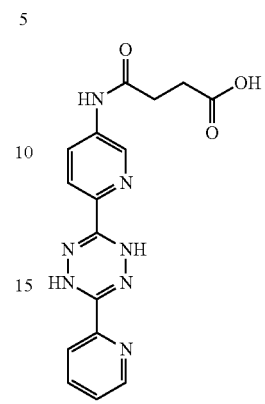
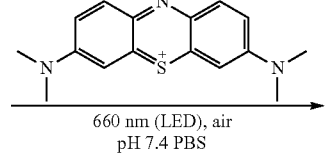
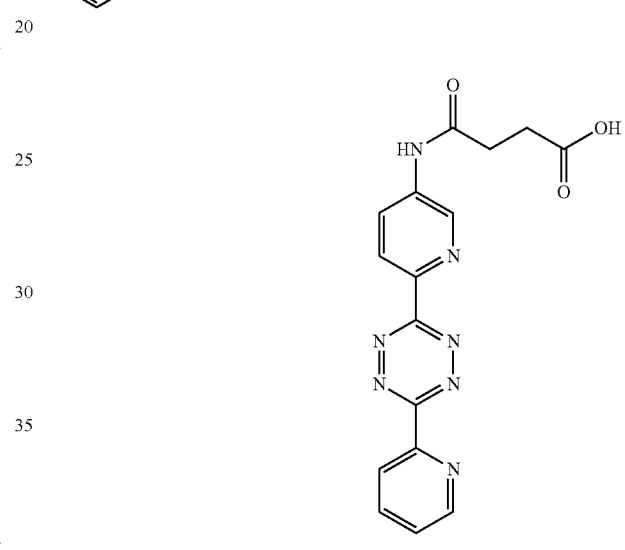

Solutions (1 mL) containing 3a (21 µM) and methylene blue (4 µM) in PBS buffer were prepared in a cuvette from stock solutions. Oxidation of 3a to 4a was monitored by recording absorbance at 325 nm every 30 seconds. Cuvettes for these experiments were washed with EDTA/PBS as described in the General Considerations (section 2.1).

Experiment 1 (continuous irradiation, FIG. 3B, main manuscript): In a cuvette, a solution of methylene blue (4 µM) and 3a (21 µM) was irradiated continuously with red light (660 nm, 9.1 mW/cm$^2$) from an LED until no further oxidation was observed.

Experiment 2 (Toggle experiment, FIG. 3C, main manuscript): In a cuvette, a solution of methylene blue (4 µM) and 3a (21 µM) was irradiated with LED red light (660 nm, 9.1 mW/cm$^2$) for an interval, and the light was turned off. This pulsing was repeated twice, and then the light was left on until no further oxidation was observed.

Experiment 3 (azide quenching experiment, FIG. 3D, main manuscript): In a cuvette, a solution of methylene blue (4 µM) and 3a (21 µM) was irradiated continuously with red light (660 nm, 2.6 mW/cm$^2$). Following 60 seconds of irradiation, solid sodium azide (3.9 mg) was directly added to the cuvette, to give a final NaN$_3$ concentration of 60 mM. Irradiation and monitoring of reaction progress was continued until no further oxidation was observed.

Carboxyfluorescein Catalyzed Photooxidation

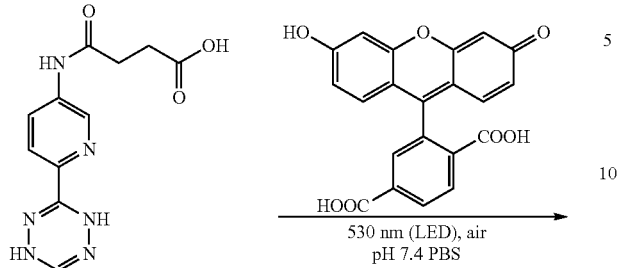

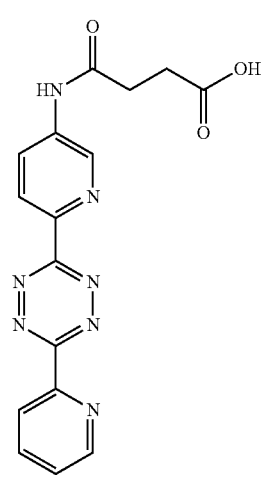

A solution (1 mL) containing 3a (19 µM) and fluorescein (7 µM) in PBS buffer with EDTA (2 mM) was prepared in a cuvette from stock solutions. Oxidation of 3a to 4a was monitored by recording absorbance at 325 nm every 10 seconds. The cuvette was irradiated with LED green light (660 nm) for an interval, and the light was turned off. This pulsing was repeated twice, and then the light was left on until no further oxidation was observed.

Rose Bengal Catalyzed Photooxidation

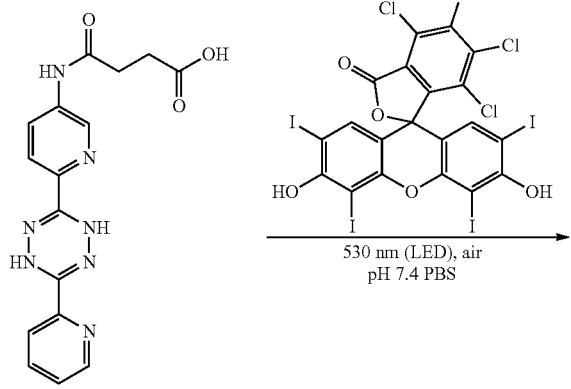

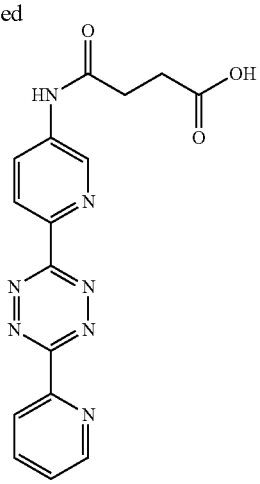

Solutions (1 mL) containing 3a and rose bengal in PBS buffer were prepared in a cuvette from stock solutions. Oxidation of 3a to 4a was monitored by recording absorbance at 325 nm every 30 seconds. Cuvettes for these experiments were washed with EDTA/PBS as described in the General Considerations (section 2.1).

Experiment 1 (continuous irradiation) In a cuvette, a solution of rose bengal (9 µM) and 3a (24 µM) was irradiated continuously with green light (528 nm, 2.2 mW/cm$^2$) from an LED until no further oxidation was observed.

Experiment 2 (Toggle experiment): In a cuvette, a solution of rose bengal (7 µM) and 3a (34 µM) was irradiated with LED green light (528 nm, 2.2 mW/cm$^2$) for an interval and the light was turned off. This pulsing was repeated twice, and then the light was left on until no further oxidation was observed.

Experiment 3 (azide quenching experiment): In a cuvette, a solution of rose bengal (2 µM) and 3a (32 µM) was irradiated continuously with LED green light (528 nm, 2.2 mW/cm$^2$). Following 60 seconds of irradiation, solid sodium azide (3.9 mg) was directly added to the cuvette, to give a final NaN$_3$ concentration of 60 mM. Irradiation and monitoring of reaction progress was continued until no further oxidation was observed.

Horseradish Peroxidase (HRP) Oxidation

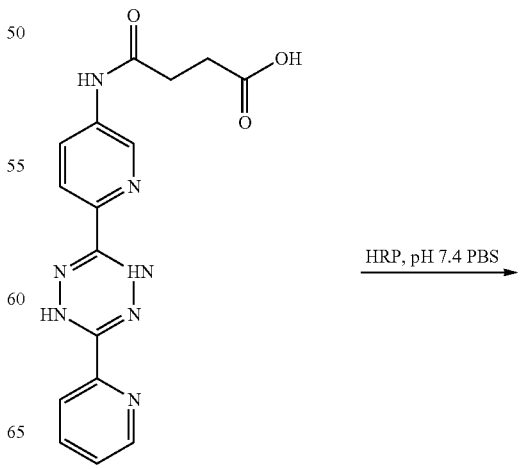

-continued

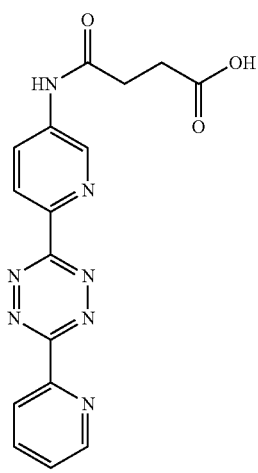

Solutions (1 mL) containing 3a (30 μm) in PBS buffer were prepared in a cuvette from stock solutions. Oxidation of 3a to 4a was monitored by recording absorbance at 325 nm every 10 seconds while either hydrogen peroxide (2 mM), HRP (15 nM) or both were added (FIG. 4, panel B). For the superoxide dismutase experiment, HRP (15 nM) was added followed by SOD (770 nM) 40 seconds later (FIG. 4, panel C). For the kinetics experiments, solutions (1 mL) containing 3a in PBS buffer with EDTA (2 mM) were prepared in the following concentrations of 3a: 9, 17, 34, 50, 83, 150 and 200 μM. The oxidation rate was determined by observing the conversion of 3a to 4a in the first 10 seconds after mixing in HRP (15 nM) and subtracting the background oxidation prior to the addition of HRP. Kinetic parameters were determined using GraphPad's Prism 6 software from the rate data presented in Table 1.

TABLE 1

| [3a] (μM) | Rate of HRP Oxidation of 3a Rate × $10^{-7}$ (M/sec) |
|---|---|
| 8 | 0.34 (+/−0.04) (3 runs) |
| 17 | 0.56 (+/−0.04) (3 runs) |
| 34 | 0.89 (+/−0.04) (3 runs) |
| 50 | 1.2 (+/−0.2) (3 runs) |
| 83 | 2.1 (+/−0.1) (3 runs) |
| 150 | 2.5 (+/−0.8) (6 runs) |
| 200 | 2.6 (+/−0.4) (3 runs) |

Dihydrotetrazine Oxidative Stability

A solution (3 mL) containing 3a (35 μM) in PBS buffer was prepared in a cuvette from stock solutions. Oxidation was monitored by recording solution absorbance at 0, 30 and 150 minutes. The cuvette was stored in the dark between measurements. Comparison of HRP, cytochrome C and hemoglobin: Solutions (1 mL) of 3a (30 μM) in PBS buffer were prepared in a cuvette from stock solutions. To the solutions, either hemoglobin (6.0 μM in protein, 1.5 μM in heme) or cytochrome C (9 μM) were added and while oxidation was monitored every 30 seconds by measuring absorbance at 325 nm.

Tetrazine Hydrolytic Stability

Solutions (1 mL) containing 4a (800 μM) in PBS buffer were prepared in cuvettes from stock solutions. Tetrazine concentration was measured by recording the absorbance at 525 nm every 20 minutes while holding the cuvette at either 25 for 24 hours. In PBS buffer at 25° C., tetrazine 4a (800 μM) shows 98% and 83% fidelity after 2 hours and 24 hours.

Azide $^1O_2$ Quenching Control Experiment with 1,3-Diphenylisobenzofuran

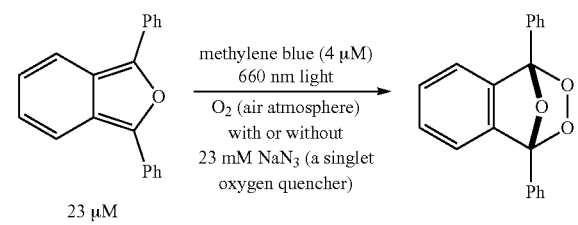 [SMILES: c1ccc(-c2oc(-c3ccccc3)c3ccccc23)cc1 ; c1ccc([C@]23OO[C@](c4ccccc4)(O2)c2ccccc23)cc1]

This experiment provides evidence that photolysis of 4 μM methylene blue solution generates singlet oxygen, and that $NaN_3$ (23 mM or higher) is an effective quencher of singlet oxygen under these conditions.

A solution (1 mL) containing 1,3-diphenylisobenzofuran (23 μM) and methylene blue (4 μM) in methanol was prepared in a cuvette from stock solutions. Consumption of 1,3-diphenylisobenzofuran was monitored by recording the solution absorbance at 410 nm every 10 seconds while the cuvette was continuously irradiated with red light (centered at 660 nm, 9.1 mW/cm$^2$) from an LED until completion. In a second, similarly prepared cuvette, sodium azide (23 mM) was added before irradiating with light. The reaction without $NaN_3$ was approximately 180% faster than the reaction with $NaN_3$.

Electrochemical Measurements

All electrochemistry was performed using a CHI-620D potentiostat/galvanostat. Cyclic voltammetry was performed using a standard three-electrode configuration. CV scans were recorded for quiescent solutions using a platinum disk working electrode (2.0 mm diameter CH Instruments) and a platinum wire auxiliary electrode. All potentials were measured against a Ag/AgCl reference electrode (CH Instruments, 1 M KCl). CV and DPV experiments were performed in a nitrogen saturated 0.1 M potassium phosphate ($KH_2PO_4$) buffered solution at pH 7.0. The concentration of the analyte was 1.0 mM for all experiments.

Spectroelectrochemical Measurements.

Controlled potential electrolysis of the analyte was carried out using a CHI-620D potentiostat/galvanostat and a standard three-electrode configuration using a platinum mesh working electrode, a platinum wire auxiliary electrode and a 1M KCl, Ag/AgCl reference electrode. The experiment was performed in a 0.1 cm quartz spectroelectrochemical cell with nitrogen saturated 0.1 M potassium phosphate ($KH_2PO_4$) buffered solution at pH 7. The concentration of the analyte was 1.0 mM. Absorbance spectra were acquired on a StellarNet CCD array UV-vis spectrometer and acquired every 5 seconds for the duration of the experiment.

DHTz-Enriched Microfiber Fabrication Experiments
Preparation of DHTz-Microfibers

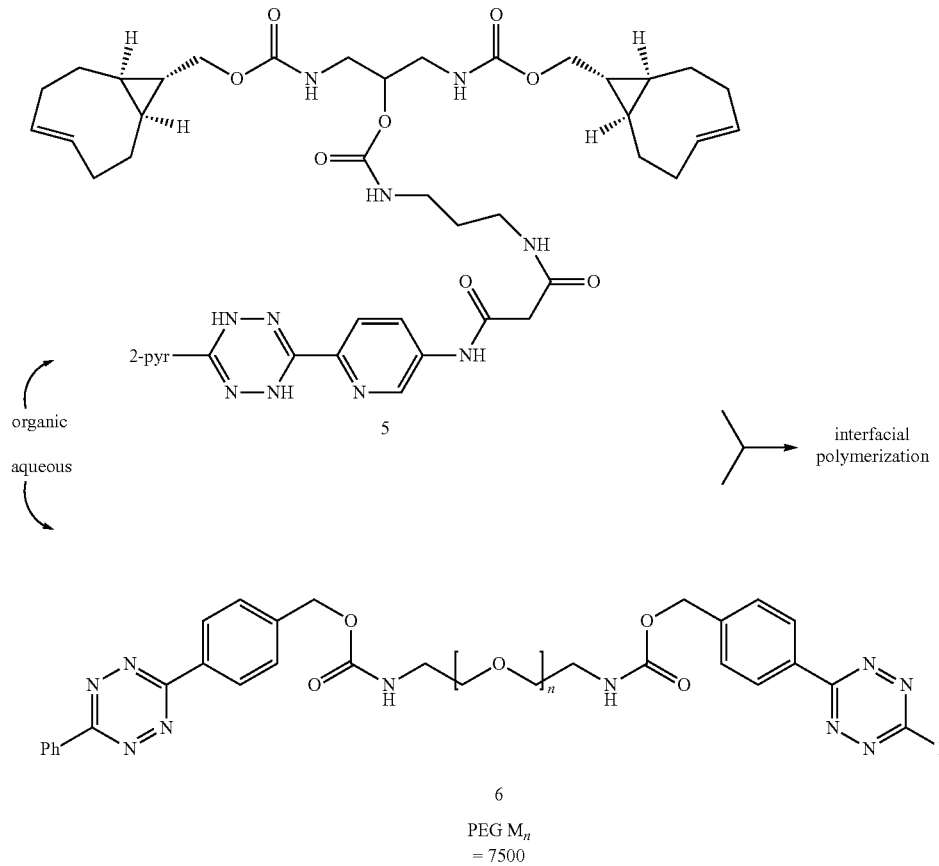

Interfacial polymerization was conducted in accord with the inventors' previously described procedure, described in S. Liu, H. Zhang, R. A. Remy, F. Deng, M. E. Mackay, J. M. Fox, X. Jia, *Adv. Mater.* 2015, 27, 2783-90. The DHTz-containing bis-sTCO monomer (5) was dissolved in ethyl acetate at a concentration of 1.2 mM. The known PEG-based bis-tetrazine monomer 6 (prepared as described in S. Liu, H. Zhang, R. A. Remy, F. Deng, M. E. Mackay, J. M. Fox, X. Jia, *Adv. Mater.* 2015, 27, 2783-90) was dissolved in water at a concentration of 0.15 mM. To a 60-mm diameter petri dish was added 3 mL of the aqueous solution of the bis-tetrazine monomer 6. The solution of 5 (3 mL) in ethyl acetate was carefully added over the aqueous phase without disturbing the interface. Upon contact, a polymer thin film formed at the interface. The thin film was grasped gently using sharp tweezers and the fiber that was pulled from the interface was connected to a collecting frame that was constructed of copper wire. The fiber was collected by manually rotating the frame. The microfibers were dried affixed onto precleaned glass slides using adhesive silicon isolators (Purchased from Grace Bio-Labs, product #665301). To 'cap' any unreacted tetrazine end groups from the monomer 6, the fibers were treated with the water soluble sTCO derivative S5 (shown below, prepared as described in H. Zhang, K. T. Dicker, X. Xu, X. Jia, J. M. Fox, ACS Macro Lett. 2014, 3, 727-731). Thus, to a silicon isolator containing DHTz-enriched microfibers was added PBS solution of S5 (1 mM). The microfibers were allowed to soak in the solution for 1 minute before the capping solution was removed. The microfibers were then rinsed using PBS solution for 3 times.

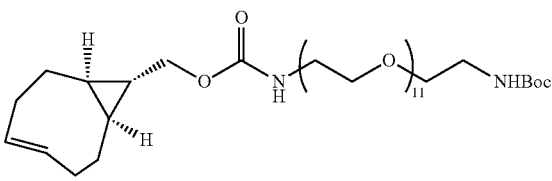

Activation and modification of the fibers was conducted inside the silicon isolators following the procedures that are outlined below. All the confocal microscope images were shot at 10× magnification unless noted otherwise.

Alexa Fluor® 647 Tagging Experiment and Control Experiments

To silicon isolator containing DHTz-functionalized microfibers was added a PBS solution of rose bengal (100 µM). The microfibers were allowed to soak in the solution for 5 minutes before rose bengal solution was removed. The microfibers were then rinsed three times with PBS buffer (~200×3 µL). The red microfibers were then immersed in PBS solution and irradiated with a 200-watt incandescent lamp for 5 minutes followed by rinsing with three portions of PBS buffer (~200×3 µL, prepared as described in S. Liu, H. Zhang, R. A. Remy, F. Deng, M. E. Mackay, J. M. Fox, X. Jia, *Adv. Mater.* 2015, 27, 2783-90). The microfibers were then treated with a PBS solution of Alexa-sTCO (1 µM) for 1 minute followed by rinsing with three portions of PBS buffer (~200×3 µL). Samples were imaged with a Zeiss LSM 5 Live DuoScan high-speed confocal microscope (Carl Zeiss, Maple Grove, Minn.).

Control without light: The procedure was identical to that described above, except that the fibers were prepared in a dark room without exposure to light.

Control without sensitizer: The microfibers were immersed in PBS buffer and irradiated with a 200-watt incandescent lamp for 5 minutes and subsequently rinsed three times with PBS buffer (~200×3 µL). The microfibers were then treated with a PBS solution of Alexa-sTCO (1 µM) for 1 minute followed by three rinses with PBS buffer (~200×3 µL). Samples were imaged with a Zeiss LSM 5 Live DuoScan high speed confocal microscope (Carl Zeiss, Maple Grove, Minn.).

Clover Protein Tagging Experiment and Control Experiment

In a silicon isolator, DHTz-functionalized microfibers were immersed in a PBS solution of methylene blue (100 µM) and irradiated with a 200-watt incandescent lamp for 5 minutes. The microfibers were then rinsed with three portions of PBS buffer (~200×3 µL) and treated with a PBS solution of Clover-sTCO (5 µM) for 1 minute followed by rinsing with three portions of PBS buffer (~200×3 µL). Samples were imaged with a Zeiss LSM 5 Live DuoScan high-speed confocal microscope (Carl Zeiss, Maple Grove, Minn.).

Control without sensitizer: The microfibers were immersed in PBS solution and irradiated with a 200-watt incandescent lamp for 5 minutes followed by rinsing with three portions of PBS buffer (~200×3 µL). The microfibers were then treated by PBS solution of Clover-sTCO (5 µM) for 1 minute followed by rinsing with three portions of PBS buffer (~200×3 µL). Samples were imaged with a Zeiss LSM 5 Live DuoScan high-speed confocal microscope (Carl Zeiss, Maple Grove, Minn.).

Oxidation of DHTz-Microfibers by Horseradish Peroxidase (HRP)

To silicon isolator containing DHTz-microfibers was added a PBS solution of HRP (10 µM). After the microfibers had been immersed in the solution for 1 hour, they were rinsed with three portions of PBS buffer (~200×3 µL). The microfibers were then treated with a PBS solution of Alexa-sTCO (1 µM) for 1 minute followed by rinsing with three portions of PBS buffer (~200×3 µL). Samples were imaged with a Zeiss LSM 5 Live DuoScan high-speed confocal microscope (Carl Zeiss, Maple Grove, Minn.).

Control without HRP: The microfibers were submerged in PBS solution for 1 hour followed by PBS solution rinsing for 3 times. The microfibers were then treated by PBS solution of Alexa-sTCO (1 µM) for 1 minute followed by rinsing with three portions of PBS buffer (~200×3 µL). Samples were imaged with a Zeiss LSM 5 Live DuoScan high-speed confocal microscope (Carl Zeiss, Maple Grove, Minn.).

RGD Peptide Tagging Experiment and Control Experiments

DHTz-microfibers were affixed to a silicone well (9 mm diameter) supported on a poly(2-hydroxyethyl methacrylate) (pHEMA)-coated 1-well Nunc® chamber using silicone isolators (Grace Bio-Labs, product #665301). The fibers were immersed in a solution of methylene blue (100 µM) in PBS, and then irradiated with a 200-watt incandescent lamp for 5 minutes followed by rinsing with three portions of PBS buffer (~200×3 µL). The microfibers were then immersed in a PBS solution of RGD-sTCO (10 µM) for 1 min followed by rinsing with three portions of PBS buffer (~200×3 µL).

Control without sensitizer: In a silicone well, the DHTz-microfibers were immersed in PBS buffer and irradiated with a 200-watt incandescent lamp for 5 minutes followed by rinsing with three portions of PBS buffer (~200×3 µL). The microfibers were then immersed in a PBS solution of RGD-sTCO (10 µM) for 1 min followed by rinsing with three portions of PBS buffer (~200×3 µL).

Control without RGD: The DHTz-microfibers were immersed in a solution of methylene blue (100 µm) in PBS, and irradiated with a 200-watt incandescent lamp for 5 minutes followed by rinsing with three portions of PBS buffer (~200×3 µL).

Control without RGD or sensitizer: The DHTz-microfibers were immersed in PBS and irradiated with a 200-watt incandescent lamp for 5 minutes followed by rinsing with three portions of PBS buffer (~200×3 µL).

Cell Culture and Confocal Imaging

Fibroblasts (NIH 3T3, ATCC, Manassas, Va.) were maintained in DMEM media supplemented with 10% fetal bovine serum (FBS) and 1% Pen-Strep (Invitrogen, Carlsbad, Calif.). DHTz-microfibers were affixed to a silicone well (9 mm diameter) supported on a poly(2-hydroxyethyl methacrylate) (pHEMA)-coated 1-well Nunc® chamber using silicone isolators (Grace Bio-labs, Bend, Oreg.). The fibers were washed with sterile PBS and cell culture media three times respectively before being sterilized under UV for 15 minutes. A 200 µL suspension of cells with a density of $0.5 \times 10^6$ cells/mL was added into each well and cultured at 37° C. for 20 hours before confocal imaging under transmitted light. Samples were imaged with a Zeiss LSM 5 Live DuoScan high-speed confocal microscope (Carl Zeiss, Maple Grove, Minn.).

Fe-Porphyrin Catalyzed Oxidation
Fe(III)tetrakis (1-methyl-4-pyridyl) Porphyrin Pentachlorideporphyrin Pentachloride (Fe-TMPyP) Catalyzed Oxidation.

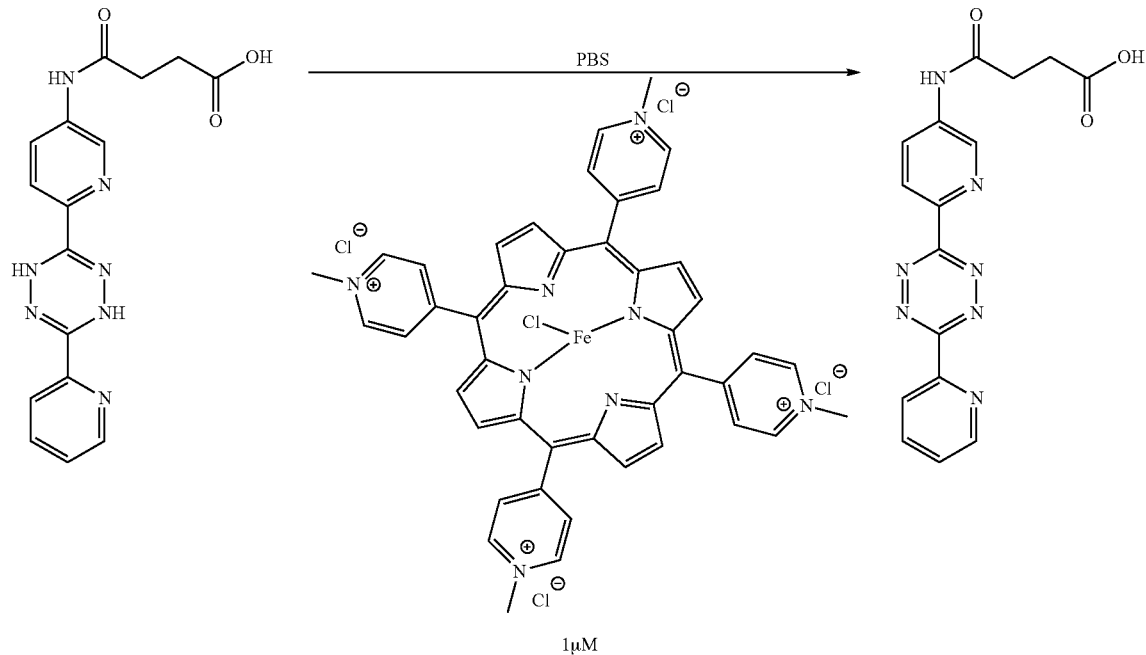

4-Oxo-4-((6-(6-(pyridin-2-yl)-1,4-dihydro-1,2,4,5-tetrazin-3-yl)pyridin-3-yl)amino)butanoic acid (35 uM in PBS (pH 7.4), 2 mL) was placed in a 1 cm×1 cm cuvette with a strongly stirred magnetic stir bar in an atmosphere of air. A solution of Fe-TMPyP (50 uM in PBS (pH 7.4), 20 uL) was added to the cuvette. The reaction was monitored by a UV-Vis spectrometer at 280 nm and 325 nm. The spectra result showed the reaction went to 50% completion within 1 minute and went to 95% completion within 5 minutes.

Fe(III)5,10,15,20-tetrakis(4-sulfonatophenyl)porphyrinato Chloride (Fe TPPS) Catalyzed Oxidation.

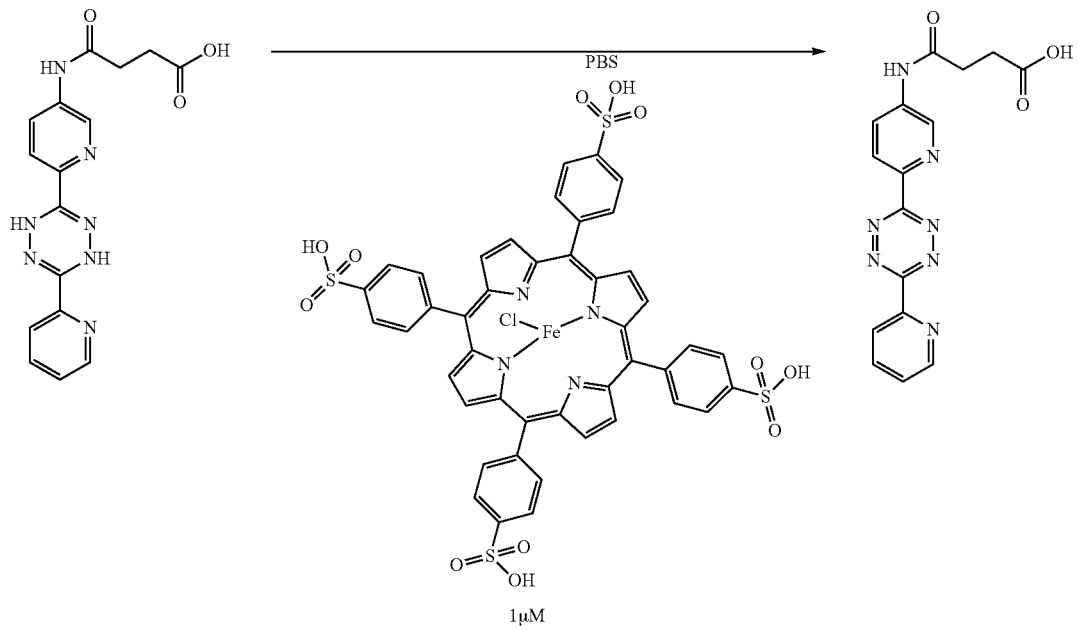

4-Oxo-4-((6-(6-(pyridin-2-yl)-1,4-dihydro-1,2,4,5-tetrazin-3-yl)pyridin-3-yl)amino)butanoic acid (35 uM in PBS (pH 7.4), 2 mL) was placed in a 1 cm×1 cm cuvette with a strongly stirred magnetic stir bar in an atmosphere of air. A solution of Fe-TPPS (50 uM in PBS (pH 7.4), 20 uL) was added to the cuvette. The reaction was monitored by a UV-Vis spectrometer at 280 nm and 325 nm. The spectra result showed the reaction went to 50% completion within 5 minutes.

Enzyme Catalyzed Oxidation of Dihydrotetrazines to Tetrazines by Engineered APEX2 (SEQ ID NO:1) to Initiate Rapid Bioorthogonal Chemistry and Intramolecular Uncaging of Phenolic Compounds Bioorthogonal reactions are a unique class of reactions due to their high selectivity allowing for biorthogonal reactive pairs to interact under biological conditions without interference by other biomolecules. Among the most popular bioorthogonal reactions are the strain-promoted alkyne-azide cycloadditions (SPAAC) and the copper catalyzed azide-alkyne 1,3-dipolar cycloadditions (CuAAC). The tetrazine-trans-cyclooctene is the fastest bioorthogonal reaction to date with a second order rate constant up to $k_2=10^6$ $M^{-1}s^{-1}$ with strained trans-cyclooctene (s-TCO) derivatives and up to $k_2=10^7$ $M^{-1}$ $s^{-1}$ with trans-1-sila-4cycloheptene, far surpassing SPAAC ($k_2=1$ $M^{-1}s^{-1}$) and CuAAC ($k_{eff}=10^2$ $M^{-1}s^{-1}$) reaction kinetics.

The fast kinetics of the tetrazine-TCO ligation allows for low concentrations of reactants, relevant for intracellular applications. Tetrazine and TCO undergo an inverse-electron demand Diels-Alder reaction (IEDDA), expelling $N_2$ as the only byproduct upon retro-[4+2] cycloaddition. IEDDA reactions are unique from the classic Diels-Alder reaction in that IEDDA requires electron-deficient dienes and electron-rich dienophiles for fast reaction kinetics. It is important to note that strained TCO derivatives can also achieve fast reaction kinetics for IEDDA reactions. While electron-deficient tetrazines increase the rate of IEDDA reactions, they are only suitable as chemical probes instead of reporters.

Typically, tetrazines are synthesized by condensation of aromatic nitriles in the presence of hydrazine to produce a dihydrotetrazine (DHTZ) intermediate whereupon chemical oxidation yields tetrazine. DHTZ is a stable precursor to tetrazine and has a longer half-life in aqueous conditions. The Fox group developed a system to induce the catalytic oxidation of DHTZ to tetrazine in situ enzymatically by horseradish peroxidase (HRP) or by photooxidation in the presence of a photocatalyst and 660 nm light. The tetrazine generated can subsequently undergo the rapid-bioorthogonal tetrazine-TCO ligation, allowing for the catalytically inducible turn-on of bioorthogonal reactivity that has been used for a broad range of applications such as protein labeling, imaging, drug delivery, and polymer cross-linking.

Horseradish peroxidase (HRP) can oxidize DHTZ under hydrogen peroxide-free conditions with a $K_m=1.0\times10^{-4}$ M, $K_{cat}=27$ $s^{-1}$, and $K_{cat}/K_m=2.7\times10^5$ $M^{-1}s^{-1}$. Addition of 1 mM hydrogen peroxide ($H_2O_2$) to the oxidation of DHTZ decreases the rate of oxidation, suggesting that HRP oxidizes DHTZ by an alternative cycle than the peroxidase cycle commonly used by HRP to oxidize small molecules. Furthermore, superoxide dismutase (SOD) addition did not suppress rate of DHTZ oxidation by HRP, confirming that superoxide is not the sole oxidant and rather there is a more rapid mechanism of DHTZ oxidation by HRP. While HRP can enzymatically activate tetrazines for subsequent rapid bioorthogonal chemistry, HRP is inactive when expressed in the reducing, calcium scarce mammalian cytosol which limits applications of this enzymatic system to mammalian endoplasmic reticulum and in vitro environments. Other heme-containing proteins such as cytochrome c and hemoglobin are not efficient catalysts for DHTZ oxidation as the rates of DHTZ oxidation by cytochrome c and hemoglobin are slow even under conditions where protein concentration was three orders of magnitude higher than HRP concentrations used.

Ascorbate peroxidase (APX) is a class I cytosolic plant peroxidase that is naturally active in reducing environments and is capable of oxidizing small molecules. To overcome limitations of utilizing HRP for electron microscopy, Ting and coworkers genetically engineered APX by point mutations and subsequent directed evolution to monomerize APX homodimer and increase APX's activity towards oxidation of small organic molecules such as 3,3'-diaminobenzidine (DAB). Ting and coworkers afforded an engineered APX called APEX2 (SEQ ID NO:1), which catalyzes the one-electron oxidization of DAB to create an electron microscopy contrast after polymerization and treatment with osmium tetroxide. APEX2 (SEQ ID NO:1) can be utilized as a genetically encoded electron microscopy tag that is active in all cellular compartments and can be spatially controlled through the localization of fusion proteins.

Herein below is described a new enzymatic system to oxidize DHTZ to tetrazine for the turn on of the rapid, bioorthogonal tetrazine-TCO ligation. Since APX is naturally active in reducing environments, APEX2 (SEQ ID NO:1) can be used as a genetically encoded catalyst that is active in all areas of the mammalian cell for localized DHTZ oxidation and activation of biorthogonal chemistry.

1. Confirming Oxidation of DHTZ by APEX2 (SEQ ID NO:1).

Figure 10:
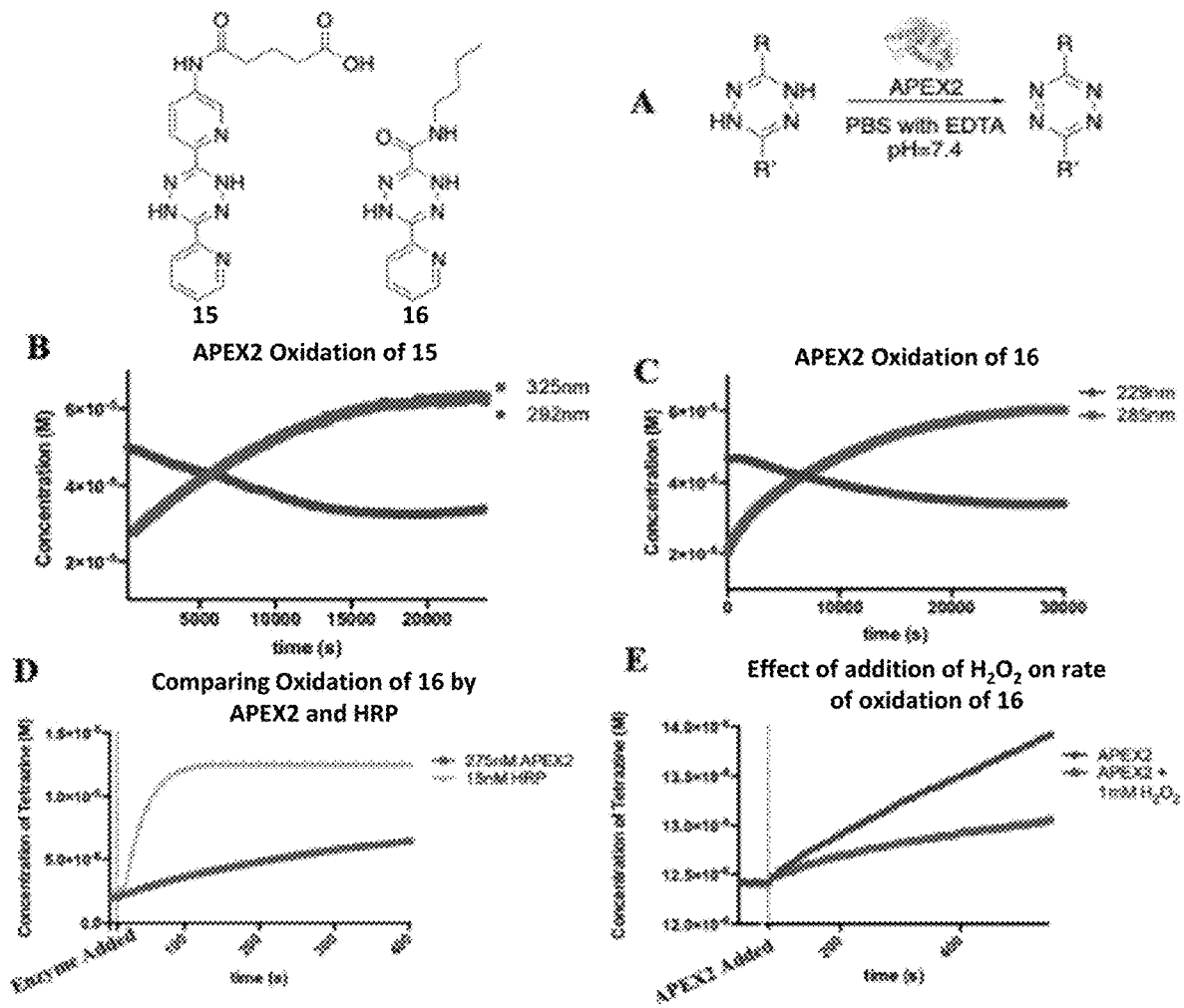
FIG. 10 shows APEX2 (SEQ ID NO:1) oxidation of DHT 15 and 16. Substrates used to measure APEX2 (SEQ ID NO:1) activity A: Reaction scheme, 275 nm APEX2 (SEQ ID NO:1) was used to oxidize DHT. EDTA was added to chelate free metals that can oxidize DHT; B: Oxidation of 60 μM 15 by APEX2 followed by UV-Vis spectrometry, $\lambda_{max}$=292 nm for DHT $\lambda_{max}$=385 nm for tetrazine; C: Oxidation of 60 μM 16 by APEX2 followed by UV-Vis spectrometry, $\lambda_{max}$ =229 nm for DHT $\lambda_{max}$ =285 nm for tetrazine; D: Shows comparison of rate of oxidation of 16 by HRP and APEX2 (SEQ ID NO:1); E: Shows effect of addition of 1 mM $H_2O_2$ on rate of oxidation of 16.

Substrates 15 and 16 were used to confirm APEX2 (SEQ ID NO:1)'s ability to oxidize DHTZ due to their stability against background oxidation and increased reactivity towards dienophiles for IEDDA reactions once oxidized. The oxidation of 15 and 16 can be measured by UV-Vis spectroscopy (FIG. 10 B-C). It should be noted that APEX2 (SEQ ID NO:1) oxidizes 15 with a $K_m=47.56$ μM, $k_{cat}=0.197$ $s^{-1}$, and $k_{cat}/K_m=4134$ $M^{-1}s^{-1}$. APEX2 (SEQ ID NO:1) also oxidizes 16 with a $K_m=22.61$ μM, $k_{cat}=0.077$ $s^{-1}$, and $k_{cat}/K_m=3426$ $M^{-1}$ $s^{-1}$ (Table 2). The rate of catalysis of 15 by APEX2 (SEQ ID NO:1) is approximately 100× slower than the rate of catalysis by HRP (FIG. 10D). APEX2 (SEQ ID NO:1) has a smaller active site than HRP, thus slower rates of catalysis by APEX2 (SEQ ID NO:1) may be a result of DHTZ's limited ability to optimally access the heme center.

The rate of oxidation of 15 by APEX2 (SEQ ID NO:1) decreases when 1 mM $H_2O_2$ is added, similarly to HRP (FIG. 10E). $H_2O_2$ can inhibit peroxidases by interacting with the native heme center forming the inhibited intermediate, compound III. Alternatively, inhibition can occur when compound I reacts with $H_2O_2$ and irreversibly inactivates peroxidases. Therefore, when 1 mM $H_2O_2$ is present, the decrease in the rate of oxidation of 15 could be due to activation of other pathways specifically, $H_2O_2$— inactivation of APEX2 (SEQ ID NO:1) protein side chains; or by the formation of the inhibited compound III intermediate. Since $H_2O_2$ activation is not required for oxidation of DHTZ, APEX2 (SEQ ID NO:1) is likely to oxidize DHTZ by the oxidase pathway.

Figure 11:
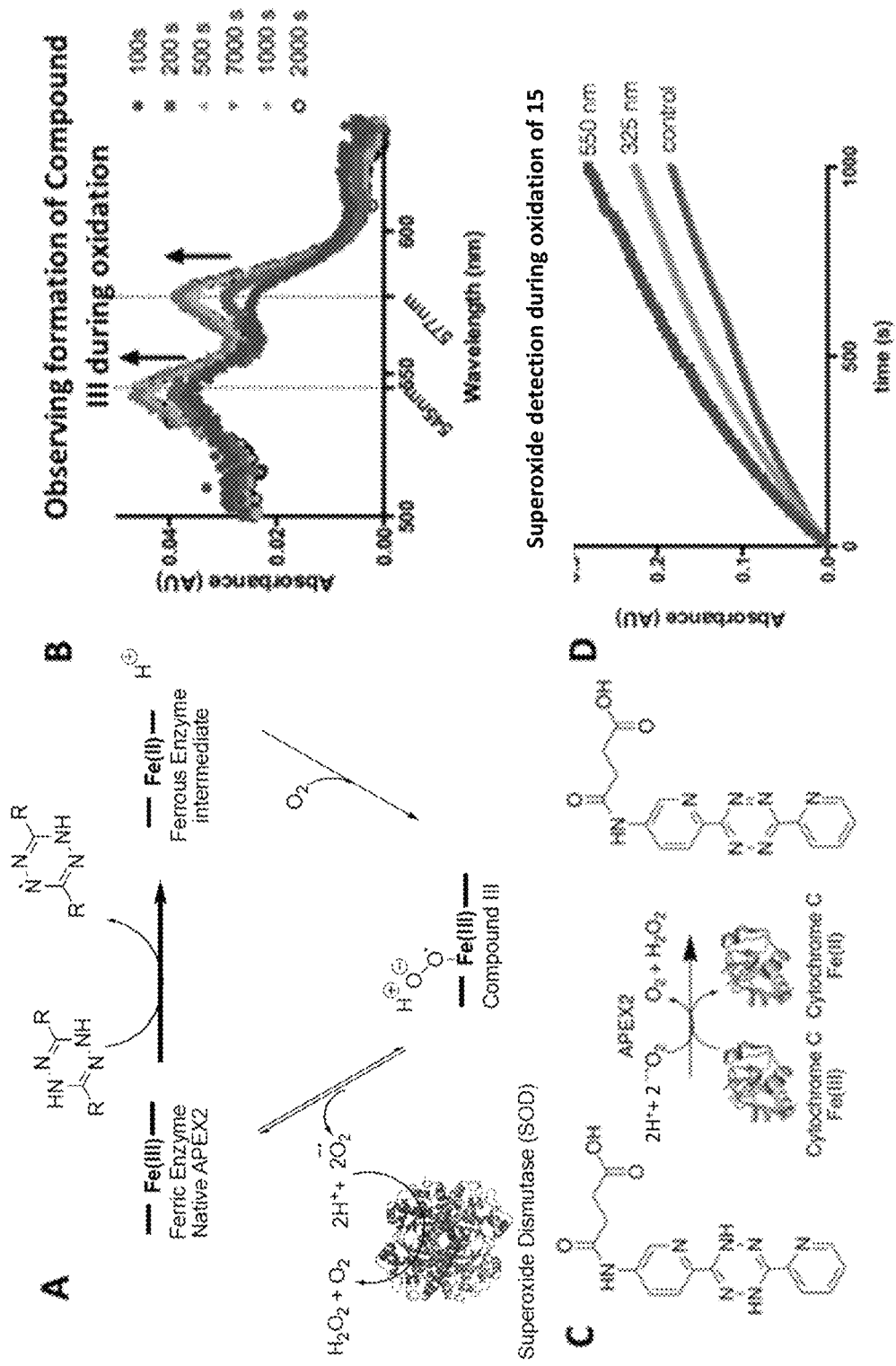
FIG. 11 shows: A. Proposed scheme for DHT oxidation by APEX2 (SEQ ID NO:1). Two cycles are required for complete oxidation of DHT. B. Compound III formed during oxidation DHT by APEX2 (SEQ ID NO:1) confirmed by increase in absorbance at $A_{max}$=545 nm and 577 nm. 2.75 μM APEX2 (SEQ ID NO:1) oxidized 50 μM of 16 in PBS with EDTA. C. Reduction of ferricytochrome c by superoxide byproduct produced during the oxidation of 15 by APEX2 (SEQ ID NO:1). D. UV traces of the reduction of ferricytochrome c by superoxide during oxidation of 15 by APEX2 (SEQ ID NO:1). Oxidation of 1 is observed at 325 nm and reduction of ferricytochrome C is observed at 550 nm. Control is the background reduction of ferricytochrome by 15.

In the proposed mechanism, APEX2 (SEQ ID NO:1) oxidizes DHTZ by two consecutive one-electron oxidations. The first one-electron oxidation produces a DHTZ radical and compound III. Release of superoxide from compound III converts compound III back to APEX2 (SEQ ID NO:1)'s native state. The cycle is repeated a second time where the second one-electron oxidation produces tetrazine (FIG. 11a). Compound III formation in HRP can be observed by UV-Vis spectrometry with characteristic wavelengths at $\lambda_{max}$=542 nm and 575 nm. The formation of compound III was evidenced by an increase in absorbance at $\lambda_{max}$=545 nm and 577 nm during the oxidation of DHTZ by APEX2 (SEQ ID NO:1) (FIG. 11b).

Superoxide has been reported to reduce ferricytochrome C Fe(III) to ferrocytochrome C Fe(II) and $O_2$. Superoxide production during oxidation of DHTZ by APEX2 (SEQ ID NO:1) has been detected by following the reduction of ferricytochrome C Fe(III) to ferrocytochrome C Fe(II) ($\lambda_{max}$=550 nm) by UV-Vis spectrometry (FIG. 11C-D). Two wavelengths, 325 nm for tetrazine formation and 550 nm for ferrocytochrome c formation, were followed where reduction of ferricytochrome C by the superoxide byproduct formed during DHTZ oxidation was observed. Addition of SOD stopped the formation of ferrocytochrome C, thus confirming that superoxide is formed during oxidation of DHTZ by APEX2 (SEQ ID NO:1). A stoichiometric background oxidation of DHTZ by ferricytochrome C was observed where the rate of the oxidation of 15 by ferricytochrome c was 2× slower than APEX2 (SEQ ID NO:1) at ferricytochrome c concentrations two orders of magnitude higher than APEX2 (SEQ ID NO:1). While oxidation of DHTZ by cytochrome C is not catalytic or feasible for intracellular applications, it does confirm that DHTZ undergoes two successive one-electron oxidations as cytochrome C cannot oxidize substrates by two-electron oxidations.

Since superoxide is a reactive oxygen species (ROS), the influx of superoxide produced during DHTZ oxidation may be damaging and inactivating APEX2 (SEQ ID NO:1). Moreover, the observed slow rates of DHTZ oxidation may be a consequence of both the formation of the inhibited compound III enzyme intermediate and the inactivation of APEX2 (SEQ ID NO:1) by superoxide. SOD converts superoxide into $H_2O_2$ and oxygen. Addition of SOD to quench the superoxide byproduct produced during oxidation of DHTZ by APEX2 (SEQ ID NO:1) resulted in increased rates of oxidation. With SOD present, APEX2 (SEQ ID NO:1) oxidizes 15 with a $K_m$=41.41 μM, $k_{cat}$=0.247 $s^{-1}$, and $k_{cat}/K_m$=5956 $M^{-1}s^{-1}$ and oxidizes 16 with a $K_m$=17.29 μM, $k_{cat}$=0.115 $s^{-1}$, and $k_{cat}/K_m$=6662 $M^{-1}s^{-1}$ (Table 2). When SOD is added to the oxidation of DHTZ by APEX2 (SEQ ID NO:1), compound III does not form as judged by the lack of an increase in absorbance at $\lambda_{max}$=545 nm and 577 nm (FIG. 12). This suggests an equilibrium occurs between compound III and native ferric APEX2 (SEQ ID NO:1). When SOD is added, the equilibrium is shifted towards the native ferric state (FIG. 11a).

Without wishing to be bound by any particular theory, it is believed that this effect is due to SOD's conversion of superoxide to $H_2O_2$. As it has been observed that the addition of low concentrations (275 nM) of $H_2O_2$ increases the rate of DHTZ oxidation when SOD was absent. Hence, it is believed that the low concentrations of $H_2O_2$ formed by SOD stimulates an alternative catalytic cycle that shifts the equilibrium from compound III to the native state heme center. The shift in equilibrium towards the native heme center when $H_2O_2$ is present overcomes the regeneration of the native heme center by the slow dissociation of superoxide from compound III. This could be an explanation for the faster rates of oxidation observed. It is important to note that only at low concentrations of $H_2O_2$ (up to 100 μM) is this effect observed, as it has been shown that at concentrations used for the peroxidase cycle (1 mM), slower rates of oxidation are observed. Therefore, the rate of oxidation of DHTZ by APEX2 (SEQ ID NO:1) increases when SOD is present because addition of SOD shifts the equilibrium from the inhibited compound III intermediate to the native ferric state, overcoming the rate-limiting step of superoxide dissociation for faster rates of oxidation.

2. Oxidation of DHTZ by APEX2 Mutant

In efforts to increase the rate of DHTZ oxidation by APEX2 (SEQ ID NO:1), mutagenesis of APEX2 (SEQ ID NO:1)'s active site is explored herein. It has been reported that the mutant W41A APX shows enhanced reactivity due to the less restricted active site. Using site-directed mutagenesis, APEX2 (SEQ ID NO:1) was mutated to F41A APEX2 to create a less restricted active site and increase rates of DHTZ oxidation. In the presence of SOD, F41A APEX2 oxidizes 15 with a $K_m$=263 μM, $k_{cat}$=1.72 $s^{-1}$, and $k_{cat}/K_m$=6533 $M^{-1}s^{-1}$ and oxidizes 16 with a $K_m$=104.6 μM, $k_{cat}$=0.408 $s^{-1}$, and $k_{cat}/K_m$=3900 $M^{-1}s^{-1}$ (Table 2). With the F41A APEX2 mutant and presence of SOD, the rate of catalysis has increased by a factor of 7 for substrate 15 and a factor of 5 for substrate 16 in comparison to APEX2 (SEQ ID NO:1).

TABLE 2

Kinetic Parameters determined from initial rates of oxidation within the first 100 s upon addition of APEX2 (SEQ ID NO: 1) or F41A APEX2.

Kinetic Parameters

| | Substrate | | | | | |
|---|---|---|---|---|---|---|
| | 15 | | | 16 | | |
| Peroxidase | APEX2 (SEQ ID NO: 1) | APEX2 (SEQ ID NO: 1) + SOD | F41A APEX2 + SOD | APEX2 (SEQ ID NO: 1) | APEX2 (SEQ ID NO: 1) + SOD | F41A APEX2 + SOD |
| $K_m$ (μM) | 47.56 | 41.41 | 263 | 22.61 | 17.29 | 104.6 |
| $K_{cat}$ ($s^{-1}$) | 0.197 | 0.247 | 1.72 | 0.077 | 0.115 | 0.408 |
| $K_{cat}/K_m$ ($M^{-1}s^{-1}$) | 4134 | 5956 | 6533 | 3426 | 6662 | 3900 |

3. Expanding DHTZ Substrates for Oxidation by F41A APEX2.

A series of DHTZ prodrug scaffolds have been developed where upon oxidation, an intramolecular IEDDA reaction occurs to release a cytotoxic drug (FIG. 13A). It should be noted that these DHTZ prodrug scaffolds are utilized herein to release combretastatin A4 (CA4) by photooxidation when a NIR photocatalyst and 660 nm light is present. F41A APEX2 can oxidize DHTZ prodrug model (17) with 100% release of a phenol to mimic a cytotoxic drug (FIG. 13B-C). F41A APEX2 also oxidizes DHTZ prodrug model (18), a prodrug with increased stability, for 55% release of nitrophenol to mimic a cytotoxic drug (FIG. 13D-E).

A fluorogenic DHTZ analog 19 was prepared, where an umbelleferone fluorophore is masked as a vinyl ether, and is therefore much less fluorescent than umbelliferone itself. Upon oxidation, the cascade of intramolecular Diels-Alder reaction followed by elimination releases free umbelliferone resulting in increased fluorescence emission (FIG. 14A). F41A APEX2 can oxidize 19 with 55% release of umbelliferone and a 10-fold turn on of fluorescence (FIG. 14B-D).

Preparation of Dihydrotetrazines

New dihydrotetrazines that were oxidized by the APEX enzyme were prepared as shown below and described in detail under the Example section:

1-(6-phenyl-1,4-dihydro-1,2,4,5-tetrazin-3-yl)ethanone

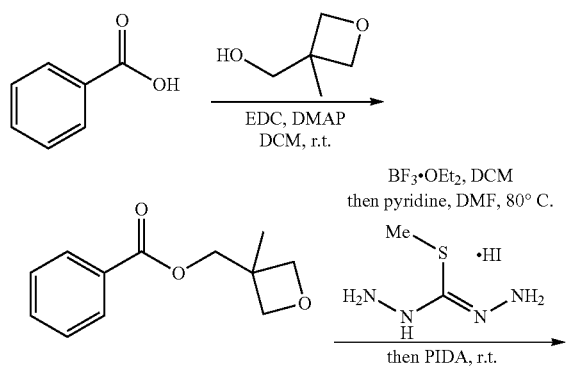

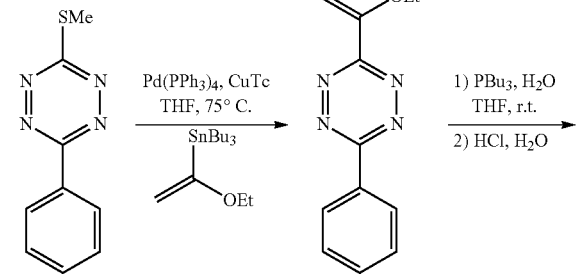

1-(6-(6-fluoropyridine-3-yl)-1,4-dihydro-1,2,4,5-tetrazin-3-yl)ethanone

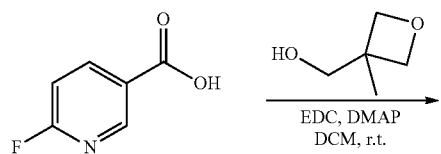

-continued

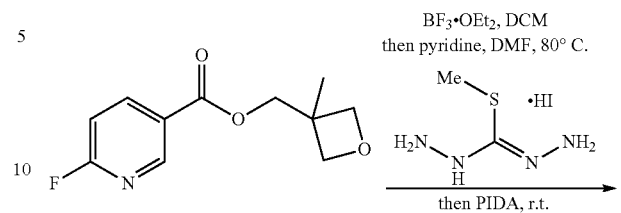

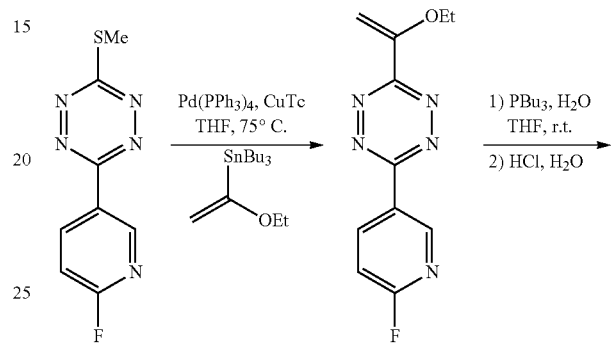

1-(6-(2-fluoro-6-(methylamino)phenyl)-1,4-dihydro-1,2,4,5-tetrazin-3-yl)ethanone

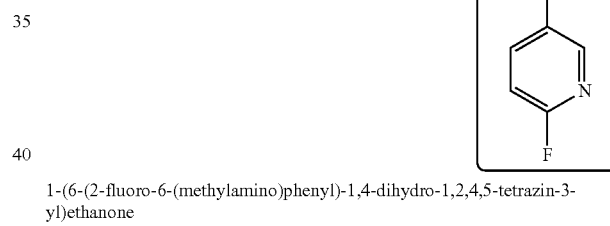

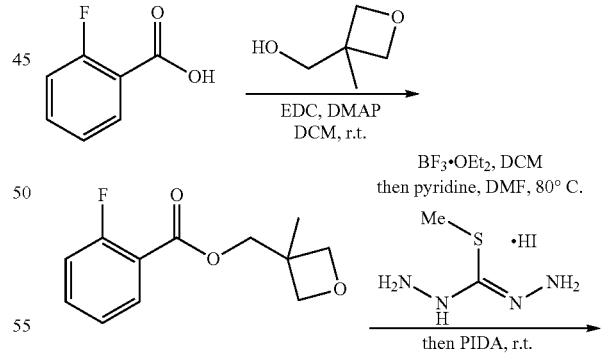

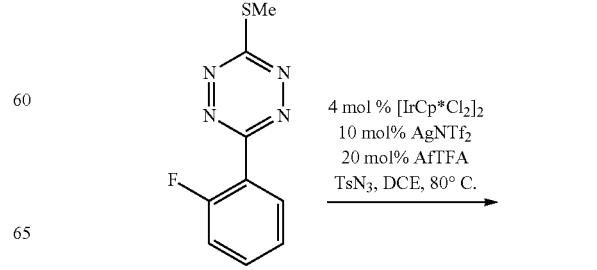

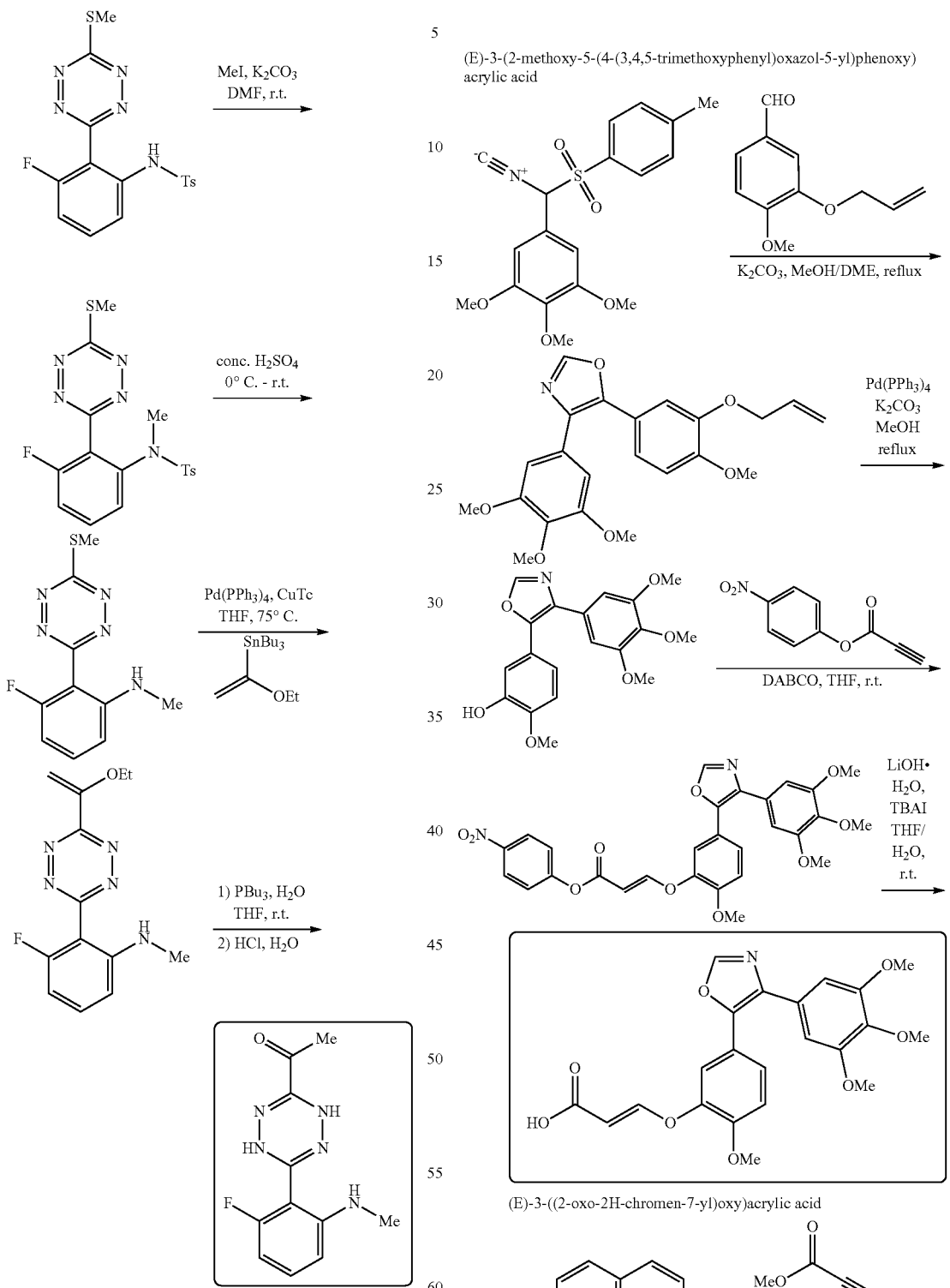
Preparation of Conjugatable 13-Aryloxyacrylic Acid Derivatives
The following compounds were prepared for conjugation to dihydrotetrazines and are described in detail under the Example section.

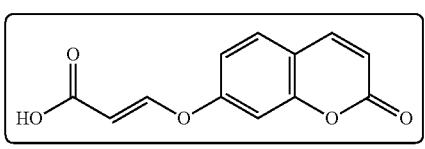

Preparation of β-Aryloxyacrylamide Derivatives

The following dihydrotetrazine compounds release phenols upon on APEX catalyzed oxidation and are described in detail under the Example section.

(E)-N-(2-(6-acetyl-1,4-dihydro-1,2,4,5-tetrazin-3-yl)-3-fluorophenyl)-N-methyl-3-(4-nitrophenoxy)acrylamide

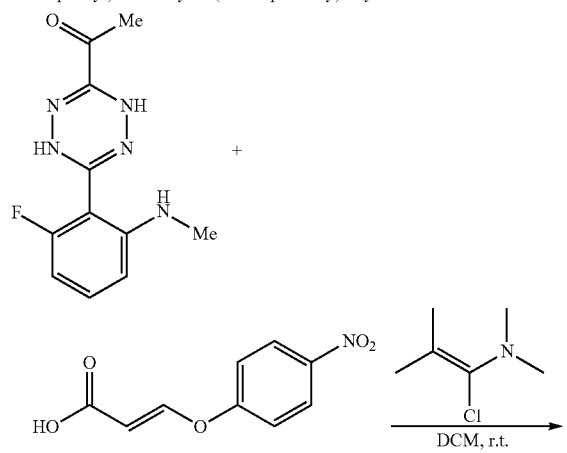

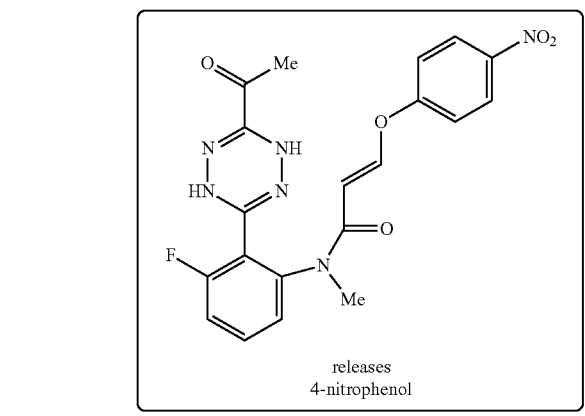

releases 4-nitrophenol (E)-N-(2-(6-acetyl-1,4-dihydro-1,2,4,5,tetrazin-3-yl)-3-fluorophenyl)-3-(2-methoxy-5-(4-(3,4,5-trimethoxyphenyl)oxazol-5-yl)phenoxy)-N-methylacrylamide

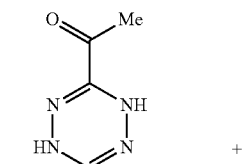

+

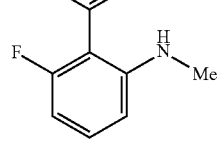

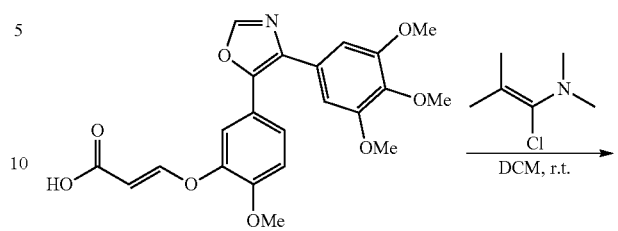

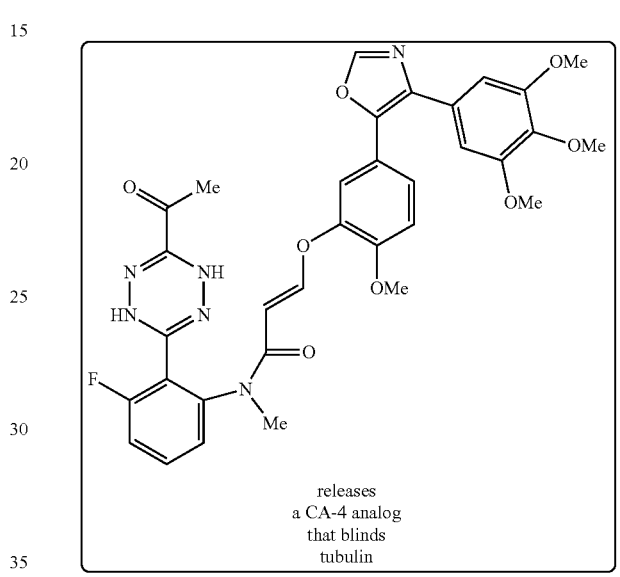

releases a CA-4 analog that blinds tubulin (E)-N-(2-(6-acetyl-1,4-dihydro-1,2,4,5-tetrazin-3-yl)-3-fluorophenyl)-3-(4-(bis(2-chloroethyl)amino)phenoxy)-N-methylacrylamide

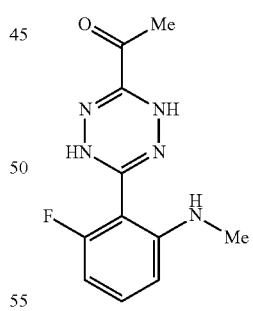

+

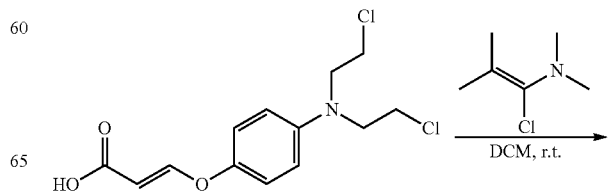

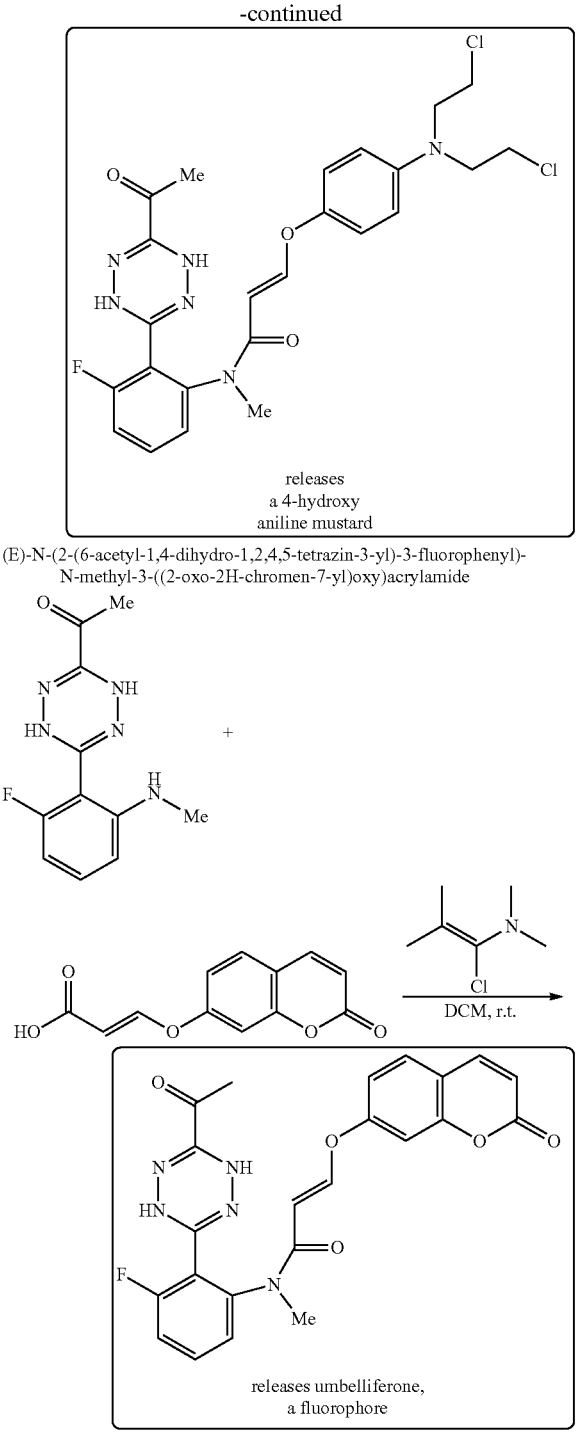

(E)-N-(2-(6-acetyl-1,4-dihydro-1,2,4,5-tetrazin-3-yl)-3-fluorophenyl)-N-methyl-3-((2-oxo-2H-chromen-7-yl)oxy)acrylamide

1. Synthetic Procedures for Enzyme Catalyzed Oxidation of Dihydrotetrazines to Tetrazines by Engineered APEX2 (SEQ ID NO:1)

1.1 General Considerations

Glassware was flamed dried under vacuum and cooled under nitrogen before carrying out the reaction. All reaction flasks were purged with nitrogen. All solvents were from a dry solvent system. Chromatography was preformed using normal phase hand columns. Carbon NMR was C13 APT with CH and CH3 facing down and C and CH2 facing up.

2. APEX2 (SEQ ID NO:1) and Expression and Purification

The pTRC APEX2 (SEQ ID NO:1) vector was purchased from addgene. APEX2 (SEQ ID NO:1) was expressed and purified according to procedures previously reported. The plasmid was transformed into E. coli strain BL21(DE3) by heat shock transformation and grown overnight at 37° C. Cells were inoculated into LB with ampicillin (100 μg/mL) and grown overnight at 37° C., then inoculated into TB (24 g yeast extract, 12 g tryptone, 4 mL glycerol, and Salts) containing ampicillin (10 μg/ml). Cells were grown in TB with good aeration at 37° C. until the optical density (OD) at 600 nm reached 0.5 at which point cells were induced with 420 μM isopropyl 1-thio-β-D-galactopyranoside (IPTG) and 1 mM 5-aminolevulinic acid (for heme incorporation). After induction of expression, temperature was lowered to 25° C. and cells were grown overnight (16 hours). Cells were harvested by centrifugation (7000 g for 10 minutes at 4° C.) and resuspended in Ni-wash buffer (50 mM phosphate salts, 30 mM imidazole, 300 mM sodium chloride). Cells were lysed by French press and high-pressure homogenizer on ice. Cell debris was removed by centrifugation (14000 g for 20 minutes at 4° C.). Supernatant was loaded onto a nickel affinity column and the APEX2 (SEQ ID NO:1)-bound resin was washed with Ni-wash buffer. APEX2 (SEQ ID NO:1) was eluted with NI elution buffer (50 mM Phosphate salts, 400 mM imidazole, 300 mM sodium chloride) and dialyzed (3×2L) at 4° C. in 25 mM phosphate buffered saline containing 100 mM NaCl and 100 μM ethylenediaminetetraacetic acid (EDTA). Protein purity was determined by 16% Tris-glycine sodium dodecyl sulfate-polyacrylamide gel electrophoresis (SDS-PAGE).

3. Site-Directed Mutagenesis of APEX2 (SEQ ID NO:1)

Prior to mutagenesis, the pTRC APEX2 (SEQ ID NO:1) vector was purchased from addgene. The plasmid was transformed into E. coli strain DH10B cells and grown overnight at 37° C. Cells were inoculated into LB with ampicillin (100 μg/mL) and grown overnight at 37° C. Cells were centrifuged (4000 g for 5 min at 4° C.) and resuspended in water. DNA was isolated by Monarch® Plasmid Miniprep Kit. Site-directed mutagenesis of APEX2 (SEQ ID NO:1) was conducted by PCR overlap extension mutagenesis. Primers to incorporate mutation were ordered from idtdna. Mutagenisis reaction was set up according to NEB's protocol, in a thin-walled PCR tube, 1.25 μL of 10 μM forward mutagenic primer and 1.25 μL of 10 μM of reverse mutagenic primer were added to a PCR reaction containing 12.5 μL of NEB's Q5® High-Fidelity 2× master mix, 0.5 μL of 200 ng APEX2 (SEQ ID NO:1) template DNA, and 9.5 μL of sterile DI water. PCR reaction carried out in a thermocycler with an annealing temperature of 62° C. The template APEX2 (SEQ ID NO:1) pTRC vector was digested by adding NEB's 1 μL of DPN1 and incubating for 1 hour at 37° C. DNA was ligated by NEB's ligation packet by incubating 5 μL of sterile DI water, 2 μL of Dpn1 digested PCR mixture, 1 μL of NEBuffer 4, 1 μL of 10× buffer for T4 DNA ligase with 10 mM ATP, 0.5 μL of PNK T4 kinase, and 0.5 μL of T4 ligase 2 hours at 37° C. The ligated DNA product was transformed by heat-shock into DH10B cells and incubated at 37° C. overnight. Cells were inoculated into LB with ampicillin (100 μg/mL) and grown overnight at 37° C. Cells were centrifuged (4000 g for 5 min at 4° C.) and resuspended in water. DNA was isolated by Monarch® Plasmid Miniprep Kit DNA. The isolated DNA containing the mutation was confirmed by sanger sequencing from GENEWIZ. The mutated plasmid was transformed into E. coli strain BL21(DE3) by heat shock transformation and expressed and purified according to procedures listed above.

For the double mutant A19V D222G APEX2, the procedure for PCR overlap extension mutagenesis, Dpn1 digestion, and ligation was followed as stated above to incorporate the A19V mutation. Ligated DNA product was transformed by heat-shock into DH10B cells and incubated at 37° C. overnight. Cells were inoculated into LB with ampicillin (100 g/mL) and grown overnight at 37° C. Cells were centrifuged (4000 g for 5 min at 4° C.) and resuspended in water. DNA was isolated by Monarch® Plasmid Miniprep Kit. The procedure for the PCR overlap extension mutatgenesis, DPN1 digestion, and ligation was repeated using A19V APEX2 as the template sequence to incorporate the D222G mutation. Ligated A19V D222G DNA product was transformed by heat-shock into DH10B cells and incubated at 37° C. overnight. Cells were inoculated into LB with ampicillin (100 g/mL) and grown overnight at 37° C. Cells were centrifuged (4000 g for 5 min at 4° C.) and resuspended in water. DNA was isolated by Monarch® Plasmid Miniprep Kit DNA. The isolated DNA containing the mutation was confirmed by sanger sequencing from GENEWIZ. The mutated plasmid was transformed into *E. coli* strain BL21 (DE3) by heat shock transformation and expressed and purified according to procedures listed above.

4. Activity Assay for APEX2 (SEQ ID NO:1) and F41A APEX2

4.1. General Considerations

UV-Vis and fluorescence measurements were conducted in quartz cuvettes. All reactions were conducted in phosphate buffered saline (PBS) containing 100 µM EDTA with a pH=7.4. The PBS was prepared by adding 25 mM phosphate salts ($Na_2HPO_4$ and $NaH_2PO_4$), 100 mM NaCl, 100 µM EDTA to DI water. EDTA was added to quench free metals that can oxidize DHT. The buffer was pH adjusted to 7.4 using 1 mM HCl and 1 mM NaOH. UV experiments were stirred at 25° C. in a temperature-controlled cuvette holder of the spectrophotometer. Solutions of 15 or 16 were prepared from methanol stock solutions.

4.2 APEX2 (SEQ ID NO:1) and F41A APEX2 Activity Assay

To test activity of APEX2 (SEQ ID NO:1) and F41A APEX2 after expression, an activity assay with Guaiacol was performed. Guaiacol (1 mM) and was added to PBS containing 100 µM EDTA. APEX2 (SEQ ID NO:1) or F41A APEX2(138 nM) was added 10 seconds after. UV experiment was started with UV traces collected every 10 seconds. After 10 seconds, $H_2O_2$ (1 mM) was added and the formation of tetraguaiacol was observed at 470 nm.

5. Oxidation of DHT by APEX2 (SEQ ID NO:1)

5.1 Observing DHT Oxidation by APEX2 (SEQ ID NO:1)

15 or 16 (60 µM) from methanol stock solutions was added to PBS containing 100 µM EDTA. After 10s, APEX2 (SEQ ID NO:1) (275 nM) was dosed in and oxidation was monitored at 325 nm for 15 and 285 nm for 16 at 60s intervals (FIG. 10B-C).

5.2 Comparing HRP and APEX2 (SEQ ID NO:1)

16 (15 µM) DHT from methanol stock solutions was added to PBS containing 100 µM EDTA. After 10s, APEX2 (SEQ ID NO:1) (275 nM) or HRP (15 nM) was dosed in and oxidation was monitored at 285 nm at 10s intervals (FIG. 10D)

5.3 Measuring Effect of $H_2O_2$ on Oxidation of DHT by APEX2 (SEQ ID NO:1) and F41A APEX2.

15 or 16 (50 µM) from stock solution was added to PBS containing 100 µM EDTA. APEX2 (SEQ ID NO:1) or F41A APEX2 (275 nM) was added 10 seconds later and oxidation of 15 or 16 was observed with UV traces every 10 seconds. In assays where $H_2O_2$ was added, 15 or 16 (50 µM) from stock solution was added to PBS containing 100 µM EDTA. After 10 seconds $H_2O_2$ (1 mM) was added followed by the addition of APEX2 (SEQ ID NO:1) or F41A APEX2 (275 nm). Oxidation of 15 or 16 was observed at every 10 seconds (FIG. 10E).

6. Influence of Superoxide on Rates of DHT Oxidation by APEX2 (SEQ ID NO:1)

6.1 Observance of Compound III Formation During Oxidation of DHT by APEX2 (SEQ ID NO:1)

16 (50 µM) from stock solution was added to PBS containing 100 µM EDTA. APEX2 (SEQ ID NO:1) or F41A APEX2 (2.75 µM) was added 10 seconds later and oxidation occurred with 60s intervals. Compound III formation was observed between 500 nm-600 nm (FIG. 11B)

6.2 Detection of Superoxide During Oxidation of Dihydrotetrazines 15 (10 µM) from stock solution was added to PBS containing 100 µM EDTA. Ferricytochrome C (60 µM) was dosed in after 10 seconds followed by addition of APEX2 (SEQ ID NO:1) (275 nm). Oxidation of 15 was observed at 325 nm with UV traces every 10 seconds. Reduction of Ferricytochrome C was observed at 550 nm. Similar results were observed with assays repeated with 15 and/or F41A APEX2 (FIG. 11D) To further confirm the generation of superoxide during the oxidation of DHT, SOD was added to quench superoxide that may form during the oxidation of DHT by APEX2 (SEQ ID NO:1). 16 (10 µM) from stock solution was added to PBS containing 100 µM EDTA. Ferricytochrome C (60 µM) was dosed in after 10 seconds followed by addition of APEX2 (SEQ ID NO:1) (275 nm). Oxidation of 16 was observed at 285 nm and reduction of cytochrome C was observed at 550 nm with UV traces every 10 seconds. SOD (100 µM) was dosed in after 1200s (FIG. 15).

6.3 Understanding SOD's Role in Increasing Rates of DHT Oxidation by APEX2 (SEQ ID NO:1)

15 (20 µM) from stock solutions was added to PBS containing 100 µM EDTA. $H_2O_2$ (275 nM-1 mM) was dosed in after 10 seconds followed by addition of F41A APEX2 (275 nm). Oxidation of 15 was observed at 325 nm with UV traces every 10 seconds (FIG. 16).

6.4 Observing DHT Oxidation by APEX2 (SEQ ID NO:1) and F41A APEX2 in Presence of SOD SOD (1 µM) was added to PBS containing 100 µM EDTA. 15 or 16 (60 µM) was added from methanol stock solutions. After 10s, APEX2 (SEQ ID NO:1) or F41A APEX2 (275 nM) was dosed in and oxidation was monitored at 325 nm for 15 and 285 nm for 16 at 60s intervals.

6.5 Observing Lack of Compound III Formation During DHT Oxidation by APEX2 (SEQ ID NO:1) with SOD SOD (50 µM) was added to PBS containing 100 µM EDTA. 16 (50 µM) from stock solution was added and after 10s, APEX2 (SEQ ID NO: 1)(2.75 µM) was dosed in and oxidation was observed with 60s intervals. Lack of compound III formation was observed between 500 nm-600 nm (FIG. 12).

7. Determining Kinetic Parameters for APEX2 (SEQ ID NO:1) and F41A APEX2

Concentrations ranging from 10 µM-80 µM of 15 or 16 were added to PBS containing 100 µM EDTA. The initial rate of oxidation was calculated from the first 100 seconds after APEX2 (SEQ ID NO:1) or F41A APEX2 was added (275 nm). In the assays where SOD was added, SOD (1 µM) was added to PBS containing 100 µM EDTA and 15 or 16 was dosed in. 10 seconds later, APEX2 (SEQ ID NO:1) or F41A APEX2 (275 nm) was added and the rate of oxidation was calculated from the first 100 seconds after APEX2 (SEQ ID NO:1) or F41A APEX2 (275 nm) addition. The initial rate of oxidation was adjusted to background oxidation of DHT in PBS with 100 µM EDTA. Kinetic parameters (Table 2) were determined using GraphPad's Prism 6 software from the data presented below (Table 3-4).

TABLE 3

Initial rate of oxidation of 15 by APEX2
(SEQ ID NO: 1) at varying concentrations

| Concentration | Initial rate of oxidation of 15 by ($\times 10^{-8}$ M/s) (2 runs) | | |
|---|---|---|---|
| of DHT (µM) | APEX2 (SEQ ID NO: 1) | APEX2 (SEQ ID NO: 1) + SOD | F41A APEX2 + SOD |
| 5 | 0.903 +/− 0.026 | — | 1.080 +/− 0.113 |
| 6 | — | 1.104 +/− 0.028 | |
| 10 | 1.286 +/− 0.141 | — | 2.625 +/− 0.177 |
| 12 | — | 1.831 +/− 0.169 | |
| 15 | 1.442 +/− 0.298 (3 runs) | 1.765 +/− 0.172 (3 runs) | 2.549 +/− 0.145 |
| 20 | 1.872 +/− 0.028 | 2.166 +/− 0.201 | 3.629 +/− 0.413 |
| 25 | 1.628 +/− 0.133 | 2.937 +/− 0.487 | 3.863 +/− 0.163 |
| 30 | 1.878 +/− 0.055 | 2.418 +/− 0.038 | 5.019 +/− 0.089 |
| 40 | 2.305 +/− 0.101 | 3.230 +/− 0.348 | 5.758 +/− 0.855 (3 runs) |
| 50 | 2.445 +/− 0.303 | 3.305 +/− 0.436 (3 runs) | 5.978 +/− 0.304 |
| 60 | 2.603 +/− 0.306 | 4.169 +/− 0.242 | 7.688 +/− 0.698 |
| 70 | 3.197 +/− 0.025 | — | 7.685 +/− 0.869 (3 runs) |
| 75 | 3.460 +/− 0.492 (3 runs) | 4.196 +/− 0.444 | 10.059 +/− 0.594 |
| 85 | 3.978 +/− 0.119 | 4.939 +/− 0.202 | 12.425 +/− 0.046 |

TABLE 4

Initial rate of oxidation of 16 by APEX2
(SEQ ID NO: 1) at varying concentrations

| Concentration | Initial rate of oxidation of 16 DHT by ($\times 10^{-8}$ M/s) (2 runs) | | |
|---|---|---|---|
| of DHT (µM) | APEX2 (SEQ ID NO: 1) | APEX2 (SEQ ID NO: 1) + SOD | F41A APEX2 + SOD |
| 4 | — | 0.429 +/− 0.022 | — |
| 5 | 0.319 +/− 0.056 | — | 0.334 +/− 0.010 |
| 10 | 0.673 +/− 0.002 | 1.011 +/− 0.170 | 0.642 +/− 0.035 |
| 15 | 0.810 +/− 0.081 | 1.662 +/− 0.004 | 1.124 +/− 0.034 |
| 20 | 1.169 +/− 0.095 | — | 2.132 +/− 0.035 |
| 25 | — | — | 2.568 +/− 0.131 |
| 30 | 1.131 +/− 0.182 (3 runs) | 2.073 +/− 0.046 | 2.129 +/− 0.076 |
| 35 | — | — | 3.078 +/− 0.025 |
| 40 | 1.427 +/− 0.265 (3 runs) | 2.379 +/− 0.350 | 2.964 +/− 0.011 |
| 45 | 1.376 +/− 0.071 | 2.234 +/− 0.088 | — |
| 50 | 1.438 +/− 0.017 | 2.149 +/− 0.009 | 3.867 +/− 0.049 |
| 55 | — | 2.503 +/− 0.210 | 3.709 +/− 0.336 |
| 60 | 1.396 +/− 0.123 | 2.376 +/− 0.450 | — |
| 70 | — | 2.746 +/− 0.180 | — |
| 75 | 1.766 +/− 0.080 | — | 4.549 +/− 0.150 |
| 85 | 1.695 +/− 0.114 | — | 5.098 +/− 0.571 |
| 90 | — | 2.491 +/− 0.032 | — |

8. Oxidation of DHT Prodrug Models 17 and 18 by F41A APEX2

8.1 Oxidation of 17 by F41A APEX2

17 (20 µM) from stock solution was added to PBS containing 100 µM EDTA. SOD (1 µM) and F41A APEX2 (275 nM) were added. Oxidation of DHT prodrug and release of phenol was observed at 275 nm with UV traces every 10 seconds. Background release was monitored by adding 17 (20 µM) from stock solution to PBS containing 100 µM EDTA with UV traces every 10 seconds (FIG. 13C).

8.2 Oxidation of 18 by F41A APEX2

18 (60 µM) from stock solution was added to PBS containing 100 µM EDTA. SOD (1 µM) and F41A APEX2 (275 nM) were added. Oxidation of DHT prodrug and release of nitrophenol was observed at 405 nm with UV traces every 10 seconds. Background release was monitored by adding 18 (20 µM) from stock solution to PBS containing 100 µM EDTA with UV traces every 10 seconds (FIG. 13D).

9. Fluorogenic DHT (19) Synthesis and Characterization 9.1 Synthetic Procedure

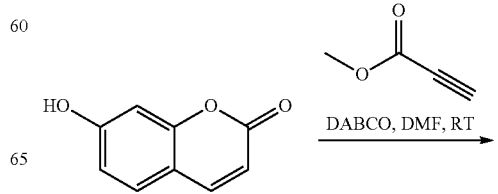

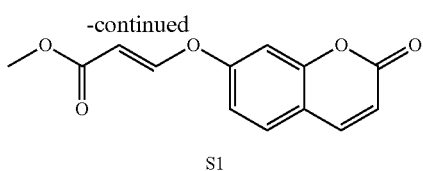

S1

Umbelliferone (0.510 g, 3.15 mmol, 1.00 equiv.) and 1,4 diazabicyclo[2,2,2] octane (0.0353 g, 0.315 mmol, 0.1 equiv.) were added to a dry round bottom and purged with nitrogen. 1.97 mL of dry DMF was added. Methylpropiolate (308 µL, 3.46 mmol, 1.1 equiv.) was added to the stirring solution dropwise and reaction was stirred overnight at room temperature. Once the reaction finished, DMF was evaporated and product was redissolved in DCM. 10% sodium hydroxide solution (10 mL) was added to the reaction mixture and aqueous phase was extracted with DCM 3 times. Organic layers were combined, dried over MgSO$_4$, and concentrated. Purification (10%-30% ethyl acetate/hexanes) afforded S1 as a white solid (626 mg, 81%). $^1$H NMR (400 MHz CDCl$_3$) δ: 7.81 (d, J=12.1 Hz, 1H), 7.68 (d, J=9.6 Hz, 1H), 7.49, (d, J=8.4 Hz, 1H), 7.05-6.99 (m, 2H), 6.28 (d, J=9.6 Hz, 1H), 5.72 (d, J=12.1 Hz, 1H), 3.76 (s, 3H). $^{13}$C NMR (101 mHz, CDCl$_3$) δ: 167.14 (C), 160.40 (C), 158.36 (C), 156.86 (CH), 155.44 (C), 142.88 (CH), 129.51 (CH), 115.88 (C), 115.72 (CH), 114.26 (CH), 105.99 (CH), 104.37 (CH), 51.74 (CH$_3$)

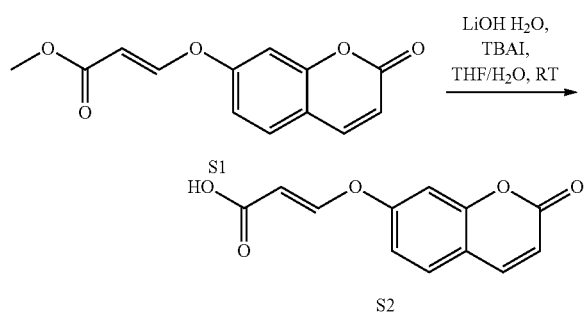

S1 (0.260 g, 1.05 mmol, 1 equiv.) and LiOH.H2O (0.133 g, 3.17 mmol, 3 equiv.) were added to 5.86 ml 1:1 THF/H$_2$O. Tetrabutylammonium iodide (0.389 g, 1.05 mmol, 1 equiv.) was added to the reaction. The reaction was stirred at room temperature for 60 hours. After the reaction, solution was diluted with water (10 mL) and acidified with HCl (3.19 mL, 1.0M). Reaction mixture was diluted with brine (10 mL) and DCM (10 mL) and aqueous layer was extracted with DCM 3 times. Organic layers were combined and dried over Na$_2$SO$_4$ and concentrated. Purification (5%-15% Acetone/DCM) afforded S2 as a white solid (103 mg, 42%). $^1$H NMR (400 MHz CDCl$_3$) δ: 7.89 (d, J=12.1 Hz, 1H), 7.69 (d, J=9.6 Hz, 1H), 7.51 (d, J=8.4 Hz, 1H), 7.07-7.01 (m, 2H), 6.40 (d, J=9.6 Hz, 1H), 5.71 (d, J=12.1 Hz, 1H).

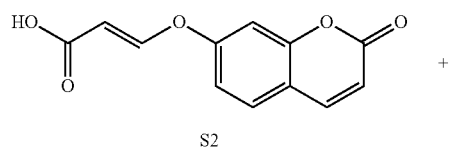

+

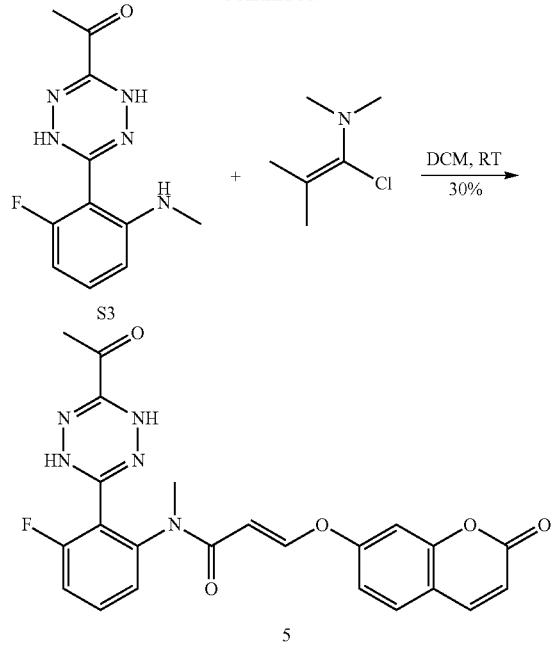

In a dry round bottom, S2 (0.019 g, 0.077 mmol, 1.5 equiv.) was added and the flask was purged with nitrogen 3 times. 1.04 mL of DCM (dry) and 1-Chloro-N,N,2-trimethyl-1-propenylamine (20.7 µL, 0.156 mmol, 3 equiv.) were added to the stirring solution. Reaction was stirred at room temperature in the dark for 3 hours. After 3 hours, S3 (0.013 g, 5.22 mmol, 1 equiv.) was added and the reaction was stirred at room temperature in the dark for 2.5 hours. After the reaction, reaction mixture was diluted with DCM and the organic layer was washed with NaHCO$_3$, and brine. Aqueous layers were washed with DCM 3 times. Organic layers were combined and dried over Na$_2$SO$_4$ and concentrated. Purification (5%-15% Acetone/DCM) afforded 5 as a yellow solid (12.2 mg, 34.4%). $^1$H NMR (400 MHz CDCl$_3$) δ: 7.79 (d, J=11.4 Hz, 1H), 7.66 (d, J=9.6 Hz, 1H), 7.61-7.45 (m, 4H), 7.16 (d, J=8.1 Hz, 1H), 7.03-6.96 (m, 2H), 6.79 (s, 1H), 6.38 (d, J=9.6 Hz, 1H), 5.58 (d, 11.5 Hz, 1H), 3.29 (s, 3H), 2.47 (s, 3H).

9.2 Emission Spectra of 19

19 (40 µM) from stock solution was added to PBS containing 100 µM EDTA and an emission scan was taken with λ$_{ex}$=370 nm (FIG. 14B)

9.3 Emission Spectra of Released Products from Oxidation of 19 by F41A APEX2

19 (40 µM) from stock solution was added to PBS containing 100 µM EDTA. SOD (1 µM) was dosed in and F41A APEX2 (275 nM) was added. After oxidation an emission scan was taken with λ$_{ex}$=370 nm (FIG. 14B)

9.4 Monitoring Oxidation of 19 and Release of Umbelliferone by UV-Vis 19 (20 µM) from stock solution was added to PBS containing 100 µM EDTA. 10s later, SOD (1 µM) and F41A APEX2 (275 nM) were added and oxidation of 19 and release of umbelliferone was observed at 370 nm with UV traces every 10 seconds. Background release was monitored by adding 19 (20 µM) from stock solution to PBS containing 100 µM EDTA with UV traces every 10 seconds (FIG. 14C).

9.5 Monitoring Oxidation of 19 and Release of Umbelliferone by Fluorescence 19 (20 μM) from stock solution was added to PBS containing 100 μM EDTA. SOD (1 μM) and F41A APEX2 (275 nM) was added. Oxidation of 19 and release of umbelliferone was observed at $\lambda_{ex}$=370 nm and $\lambda_{em}$=452 nm with traces every 10 seconds. Background release was monitored by adding 19 (20 μM) from stock solution to PBS containing 100 μM EDTA with $\lambda_{ex}$=370 nm and $\lambda_{em}$=452 nm with traces every 10 seconds (FIG. 14D).

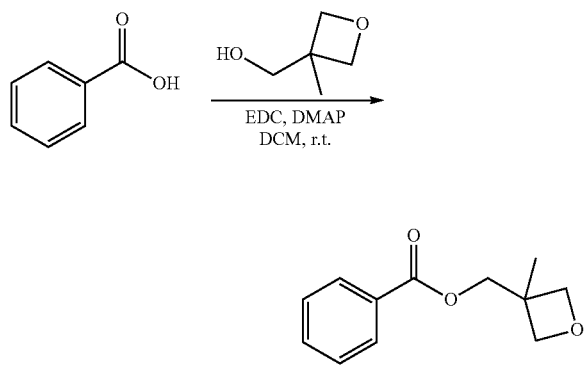

(3-methyloxetan-3-yl)methyl Benzoate

A dry round-bottom flask was charged with 3-methyl-3-oxetanemethanol (1560 μL, 15.59 mmol 1.1 equiv.), 1-(3-dimethylaminopropyl)-3-ethylcarbodiimide hydrochloride (3281 mg, 17.11 mmol, 1.2 equiv.) and DMAP (171.1 mg, 1.417 mmol, 0.10 equiv.). The flask was outfitted with a septum-fitted gas inlet adapter and then evacuated and filled with nitrogen. Anhydrous $CH_2Cl_2$ (28 mL, 0.5 M) was added to the flask via syringe. The flask was cooled by an ice bath (0° C.), and benzoic acid (1730 mg, 14.17 mmol, 1 equiv.) was added. After stirring under nitrogen at 0° C. for 15 min and at r.t overnight, the reaction mixture was diluted with $CH_2Cl_2$. The solution was washed with saturated sodium bicarbonate solution, water and brine, and the organics were dried over sodium sulfate and concentrated by rotary evaporation. The residue was purified by flash column chromatography on silica gel (Hexane:EA 10:0 to 8:2). $^1$H NMR (400 MHz, CDCl$_3$) δ 8.33-7.98 (m, 2H), 7.81-7.52 (m, 1H), 7.53-7.26 (m, 2H), 4.65 (d, J=6.0 Hz, 2H), 4.46 (d, J=6.0 Hz, 2H), 4.39 (s, 2H), 1.42 (s, 3H). $^{13}$C NMR (101 MHz, CDCl$_3$) δ 166.59 (C), 133.25 (CH), 129.93 (C), 129.69 (CH), 128.54 (CH), 79.68 (CH$_2$), 69.06 (CH$_2$), 39.35 (C), 21.36 (CH$_3$). HRMS [M+H]$^+$ m/z calcd. for [C$_{11}$H$_{14}$O$_3$N]$^+$ 207.1021, found 207.1014.

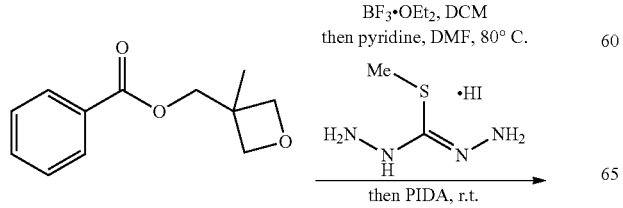

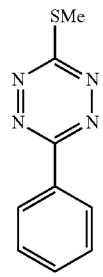

3-(methylthio)-6-phenyl-1,2,4,5-tetrazine

A dry round-bottom flask was charged with the (3-methyloxetan-3-yl)methyl benzoate (1200 mg, 5.87 mmol, 1.0 equiv.) and a magnetic stirbar. The flask was outfitted with a septum-fitted gas inlet adapter, evacuated and refilled with nitrogen. Anhydrous $CH_2Cl_2$ (0.59 mL, 1.0 M in oxetane ester) was added via syringe and the resulting solution was cooled by an ice/brine bath (−5° C.) and boron trifluoride etherate (362 μL, 2.94 mmol, 0.50 equiv.) was added via syringe. The resulting mixture was allowed to stir under nitrogen with continued cooling by the cold bath (maintained between −5° C. to −0° C.) for 34 h. The reactions were monitored by TLC of aliquots that were quenched with trimethylamine before spotting the TLC plate. When the oxetane was completely consumed, the reaction mixture was quenched with pyridine (948 μL, 11.7 mmol, 2.0 equiv.), and then methyl hydrazinecarbohydrazonothioate hydroiodide (1019 mg, 4.11 mmol, 0.70 equiv.) and DMF (4.1 mL, to 1.0 M in methyl hydrazinecarbohydrazonothioate hydroiodide) were added. The mixture was stirred vigorously and vacuum was carefully applied to remove $CH_2Cl_2$. The resulting mixture was then heated by an oil bath at 80° C. and the mixture was allowed to stir under nitrogen at 80° C. for 1 h. After cooling to r.t., PIDA (1323 mg, 4.11 mmol, 0.70 equiv.) was added to the flask and the mixture allowed to stir at r.t. for 1 h. The mixture was diluted with $CH_2Cl_2$ and sequentially washed with saturated sodium bicarbonate, water and brine, dried over sodium sulfate and concentrated by rotary evaporation. The residue was purified by flash column chromatography on silica gel. A red solid (587 mg, 2.87 mmol, 72%) was obtained after purified by chromatography ($CH_2Cl_2$: ether 100:0 to 95:5). $^1$H NMR (400 MHz, CDCl$_3$) δ 8.65-8.20 (m, 2H), 8.09-7.46 (m, 3H), 2.80 (s, 3H). $^{13}$C NMR (101 MHz, CDCl$_3$) δ 175.43 (C), 162.44 (C), 132.45 (CH), 131.71 (C), 129.38 (CH), 127.62 (CH), 13.60 (CH$_3$). HRMS [M+H]$^+$ m/z calcd. for [C$_9$H$_9$N$_4$S]$^+$ 205.0548, found 205.0540.

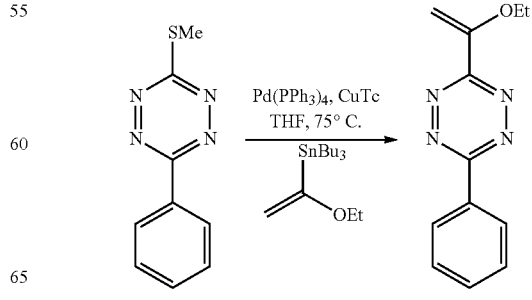

3-(1-ethoxyvinyl)-6-phenyl-1,2,4,5-tetrazine

To a dry round-bottom flask was added 3-(methylthio)-6-phenyl-1,2,4,5-tetrazine (50 mg, 0.24 mmol, 1 equiv.), Pd(PPh$_3$)$_4$ (43 mg, 0.037 mmol, 15 mol %) and CuTc (94 mg, 0.49 mmol, 2 equiv.) The flask was outfitted with a septum-fitted gas inlet adapter, and was twice evacuated and backfilled with nitrogen. Tributyl(1-ethoxyvinyl)tin (0.17 mL, 0.49 mmol, 2 equiv.) and anhydrous dioxane (49 mL, 5 mM) were added via syringe, and the flask was heated by an oil bath at 100° C. for 30 min. After cooling down, the reaction mixture was diluted with hexane and filtered through short pad of 10% K$_2$CO$_3$ modified silica gel. Et$_2$O was used to washed off all red fractions. The residue was concentrated by rotary evaporation and purified by flash column chromatography on 10% K$_2$CO$_3$ modified silica gel. A pink soild (41 mg, 0.18 mmol, 74%) was obtained after column chromatography (CH$_2$Cl$_2$:Et$_2$O 100:0 to 96:4). $^1$H NMR (400 MHz, CDCl$_3$) δ 8.63 (dd, J=8.2, 1.6 Hz, 2H), 7.72-7.46 (m, 3H), 6.02 (d, J=2.9 Hz, 1H), 4.93 (d, J=2.9 Hz, 1H), 4.15 (q, J=7.0 Hz, 2H), 1.55 (t, J=7.0 Hz, 3H). $^{13}$C NMR (101 MHz, CDCl$_3$) δ 164.15 (C), 161.78 (C), 153.73 (C), 133.00 (CH), 131.74 (C), 129.44 (CH), 128.30 (CH), 93.16 (CH$_2$), 64.67 (CH$_2$), 14.51 (CH$_3$). HRMS [M+H]$^+$ m/z calcd. for [C$_{12}$H$_{13}$ON$_4$]$^+$ 229.1089, found 229.1082.

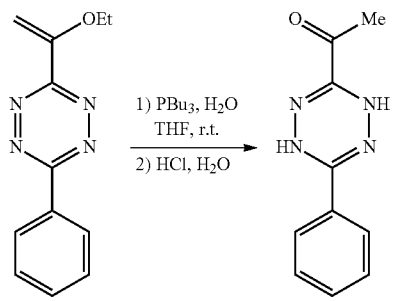 [SMILES: C=C(OCC)c1nnc(-c2ccccc2)nn1 ; CC(=O)C1=NNC(c2ccccc2)=NN1]

1-(6-phenyl-1,4-dihydro-1,2,4,5-tetrazin-3-yl)ethan-1-one

A round-bottom flask was charged with 3-(1-ethoxyvinyl)-6-phenyl-1,2,4,5-tetrazine (120 mg, 0.526 mmol, 1 equiv) and a magnetic stir bar. The flask was outfitted with a septum-fitted gas inlet adapter, evacuated and refilled with nitrogen. Anhydrous THF (5.3 mL, 0.1 M), PBu$_3$ (259 μL, 1.05 mmol, 2 equiv) and water (93.0 μL, 5.26 mmol, 10 equiv) was added by syringe. After stirring at room temperature for 4 h, 1M HCl (10.5 mL, 10.5 mmol, 20 equiv) was added by syringe. After stirring at room temperature overnight, the resulting mixture was diluted with DCM, neutralized by saturate sodium bicarbonate solution until pH>7, washed with water and brine, dried over sodium sulfate, and concentrated by rotary evaporation. A yellow solid (95.1 mg, 0.470 mmol, 89%) was obtained after column chromatography (Hexane:DCM 1:1 to 15:85). $^1$H NMR (400 MHz, CDCl$_3$) δ 7.74-7.59 (m, 2H), 7.54-7.39 (m, 4H), 7.21 (s, 1H), 2.46 (s, 3H). $^{13}$C NMR (101 MHz, CDCl$_3$) δ 191.36 (C), 146.61 (C), 144.89 (C), 131.14 (CH), 129.37 (C), 129.11 (CH), 126.09 (CH), 24.78 (CH$_3$).

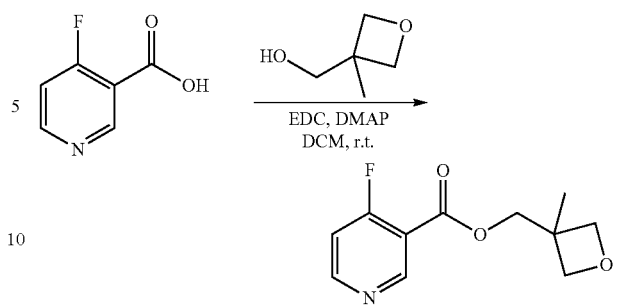

(3-methyloxetan-3-yl)methyl 2-fluoro Benzoate

A dry round-bottom flask was charged with 3-methyl-3-oxetanemethanol (823 mg, 8.06 mmol, 1.1 equiv.), 1-(3-dimethylaminopropyl)-3-ethylcarbodiimide hydrochloride (1854 mg, 9.67 mmol, 1.2 equiv.) and DMAP (105 mg, 0.806 mmol, 0.10 equiv.). The flask was outfitted with a septum-fitted gas inlet adapter and then evacuated and filled with nitrogen. Anhydrous CH$_2$Cl$_2$ (17 mL, 0.5 M). was added to the flask via syringe. The flask was cooled by an ice bath (0° C.), and 2-fluorobenzoic acid (1242 mg, 8.87 mmol, 1 equiv.) was added. After stirring under nitrogen at 0° C. for 15 min and at r.t overnight, the reaction mixture was diluted with CH$_2$Cl$_2$. The solution was washed with saturated sodium bicarbonate solution, water and brine, and the organics were dried over sodium sulfate and concentrated by rotary evaporation. The residue was purified by flash column chromatography on silica gel. A colorless oil (1889 mg, 8.43 mmol, 95%) was obtained after column chromatography (Hexane:EA 10:0 to 9:1). $^1$H NMR (400 MHz, CDCl$_3$) δ 7.95 (td, J=7.5, 1.9 Hz, 1H), 7.52 (m, 1H), 7.21 (td, J=7.6, 1.1 Hz, 1H), 7.13 (m, 1H), 4.61 (d, J=6.0 Hz, 2H), 4.44 (d, J=6.0 Hz, 2H), 4.41 (s, 2H), 1.42 (s, 3H). $^{13}$C NMR (101 MHz, CDCl$_3$) δ 164.60 (d, J$_{C-F}$=3.9 Hz, C), 162.10 (d, J$_{C-F}$=258.7 Hz, C), 134.82 (d, J$_{C-F}$=9.0 Hz, CH), 132.24 (CH), 124.14 (d, J$_{C-F}$=3.9 Hz, CH), 118.50 (d, J$_{C-F}$=10.2 Hz, C), 117.16 (d, J$_{C-F}$=22.2 Hz, CH), 79.67 (CH$_2$), 69.58 (CH$_2$), 39.30 (C), 21.32 (CH$_3$). HRMS [M+H]$^+$ m/z calcd. for [C$_{12}$H$_{14}$O$_3$F]$^+$ 225.0927, found 225.0918.

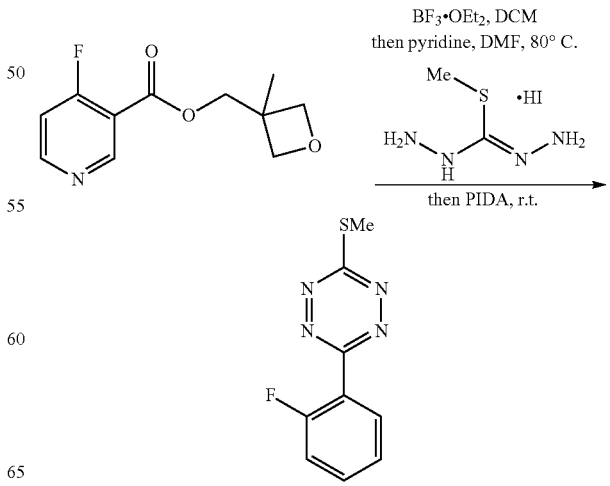

3-(2-fluorophenyl)-6-(methylthio)-1,2,4,5-tetrazine

A dry round-bottom flask was charged with (3-methyloxetan-3-yl)methyl 2-fluoro benzoate (358 mg, 1.60 mmol, 1.0 equiv.) and a magnetic stirbar. The flask was outfitted with a septum-fitted gas inlet adapter, evacuated and refilled with nitrogen. Anhydrous $CH_2Cl_2$ (1.6 mL, 1.0 M in oxetane ester) was added via syringe and the resulting solution was cooled by an ice/brine bath (−5° C.) and boron trifluoride etherate (98.5 μL, 0.798 mmol, 0.50 equiv.) was added via syringe. The resulting mixture was allowed to stir under nitrogen with continued cooling by the cold bath (maintained between −5° C. to −0° C.) for 6 h. The reactions were monitored by TLC of aliquots that were quenched with trimethylamine before spotting the TLC plate. When the oxetane was completely consumed, the reaction mixture was quenched with pyridine (258 μL, 3.19 mmol, 2.0 equiv.), and then methyl hydrazinecarbohydrazonothioate hydroiodide (277 mg, 1.12 mmol, 0.70 equiv.) and DMF (1.1 mL) were added. The mixture was stirred vigorously and vacuum was carefully applied to remove $CH_2Cl_2$. The resulting mixture was then heated by an oil bath at 80° C. and the mixture was allowed to stir under nitrogen at 80° C. for 1 h. After cooling to r.t., PIDA (361 mg, 1.12 mmol, 0.70 equiv.) was added to the flask and the mixture allowed to stir at r.t. for 1 h. The mixture was diluted with $CH_2Cl_2$ and sequentially washed with saturated sodium bicarbonate, water and brine, dried over sodium sulfate and concentrated by rotary evaporation. The residue was purified by flash column chromatography on silica gel. A red solid (177 mg, 0.797 mmol, 50%) was obtained after purified by chromatography (Hexane: EA 100:0 to 95:5). $^1$H NMR (400 MHz, $CDCl_3$) δ 8.21 (td, J=7.6, 1.8 Hz, 1H), 7.59 (m, 1H), 7.37 (td, J=7.6, 1.2 Hz, 1H), 7.30 (m, 1H), 2.80 (s, 3H). $^{13}$C NMR (101 MHz, $CDCl_3$) δ 175.21 (C), 162.06 (d, $J_{C-F}$=5.5 Hz, C), 161.33 (d, $J_{C-F}$=257.0 Hz, C), 133.76 (d, $J_{C-F}$=8.5 Hz, CH), 131.07 (d, $J_{C-F}$=1.4 Hz, CH), 124.88 (d, $J_{C-F}$=3.9 Hz, CH), 120.57 (d, $J_{C-F}$=9.9 Hz, C), 117.43 (d, $J_{C-F}$=21.5 Hz, CH), 13.58 ($CH_3$). HRMS [M+H]+m/z calcd. for $[C_9H_8N_4FS]^+$ 223.0454, found 223.0447.

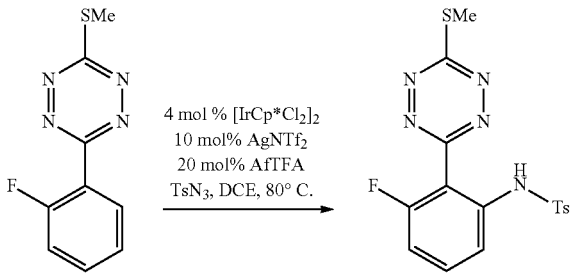 [SMILES: CSc1nnc(-c2ccccc2F)nn1 ; CSc1nnc(-c2c(F)cccc2NS(=O)(=O)c2ccc(C)cc2)nn1]

N-(3-fluoro-2-(6-(methylthio)-1,2,4,5-tetrazin-3-yl)phenyl)-4-methylbenzenesulfonamide A dry round-bottom flask was charged with 3-(2-fluorophenyl)-6-(methylthio)-1,2,4,5-tetrazine (301 mg, 1.35 mmol, 1 equiv), pentamethylcyclopentadienyliridium (III) chloride dimer (43.2 mg, 0.0542 mmol, 4 mol %), Silver bis(trifluoromethanesulfonyl)imide (84.0 mg, 0.217 mmol, 16 mol %), silver trifluoroacetate (59.8 mg, 0.271 mmol, 20 mol %) and a magnetic stirbar. The flask was outfitted with a septum-fitted gas inlet adapter, evacuated and refilled with nitrogen. Anhydrous 1,2-dichloroethane (13.5 mL, 0.1M) and p-toluenesulfonyl azide (15% w/w, 4.94 mL, 3.39 mmol, 2.5 equiv) was added by syringe. After refluxing under nitrogen at 80° C. for 3 h, the mixture was purified by column chromatography without aqueous workup. A red oil (475 mg, 1.22 mmol, 90%) was obtained after column chromatography (Hexane:DCM 1:1 to 1:9). (When scale is over 400 mg, be careful when evaporate solvent in vial. Product as thick oil may contaminate vial dryer. If directly transfer to round bottom for next step, yield of next step will not be affected) $^1$H NMR (400 MHz, $CDCl_3$) δ 8.79 (s, 1H), 7.76-7.37 (m, 2H), 7.24-7.10 (m, 3H), 7.03 (d, J=8.1 Hz, 2H), 2.80 (s, 3H), 2.34 (s, 3H). $^{13}$C NMR (101 MHz, $CDCl_3$) δ 174.92 (C), 160.93 (d, J=255.8 Hz, C), 160.35 (d, J=4.4 Hz, C), 144.45 (C), 136.84 (d, J=2.65 Hz, C), 135.16 (C), 133.36 (d, J=10.4 Hz, CH), 129.72 (CH), 126.36 (CH), 123.09 (d, J=3.3 Hz, CH), 114.74 (d, J=21.8 Hz, CH), 114.74 (C), 21.66 ($CH_3$), 13.58 ($CH_3$). HRMS [M+H]+m/z calcd. for $[C_{16}H_{15}O_2N_5FS_2]^+$ 392.0651, found 392.0639.

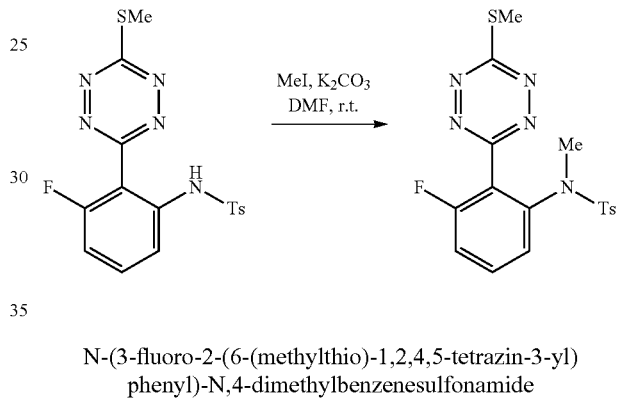

N-(3-fluoro-2-(6-(methylthio)-1,2,4,5-tetrazin-3-yl)phenyl)-N,4-dimethylbenzenesulfonamide A dry round-bottom flask was charged with N-(3-fluoro-2-(6-(methylthio)-1,2,4,5-tetrazin-3-yl)phenyl)-4-methylbenzenesulfonamide (1.20 g, 3.07 mmol, 1 equiv), potassium carbonate (0.636 g, 4.60 mmol, 1.5 equiv) and and a magnetic stirbar. The flask was outfitted with a septum-fitted gas inlet adapter, evacuated and refilled with nitrogen. Anhydrous DMF (10 mL, 0.3 M) and iodomethane (0.573 mL, 9.20 mmol, 3 equiv) was added by syringe. After stirring at room temperature overnight, the resulting mixture was diluted with DCM, washed sequentially with saturate sodium bicarbonate solution, water and brine, dried over sodium sulfate and concentrated by rotary evaporation. A red solid (1.23 g, 3.03 mmol, 99%) was obtained after column chromatography (Hexane:DCM 1:1 to 1:9). $^1$H NMR (400 MHz, $CDCl_3$) δ 7.47 (td, J=8.2, 6.0 Hz, 1H), 7.41-7.35 (m, 2H), 7.32-7.26 (m, 1H), 7.24-7.20 (m, 2H), 6.85-6.78 (m, 1H), 3.30 (s, 3H), 2.80 (s, 3H), 2.43 (s, 3H). $^{13}$C NMR (101 MHz, $CDCl_3$) δ 175.29 (C), 161.02 (d, J=2.35 Hz, C), 160.97 (d, J=253.6 Hz, C), 143.94 (C), 141.90 (d, J=3.85 Hz, C), 134.39 (C), 132.26 (d, J=9.81 Hz, CH), 129.56 (CH), 127.57 (CH), 124.38 (d, J=3.49 Hz, CH), 123.44 (d, J=13.6 Hz, C), 116.73 (d, J=21.5 Hz, CH), 40.01 ($CH_3$), 21.62 ($CH_3$), 13.45 ($CH_3$).

HRMS [M+H]$^+$ m/z calcd. for $[C_{17}H_{17}O_2N_5FS_2]^+$ 406.0808, found 406.0807.

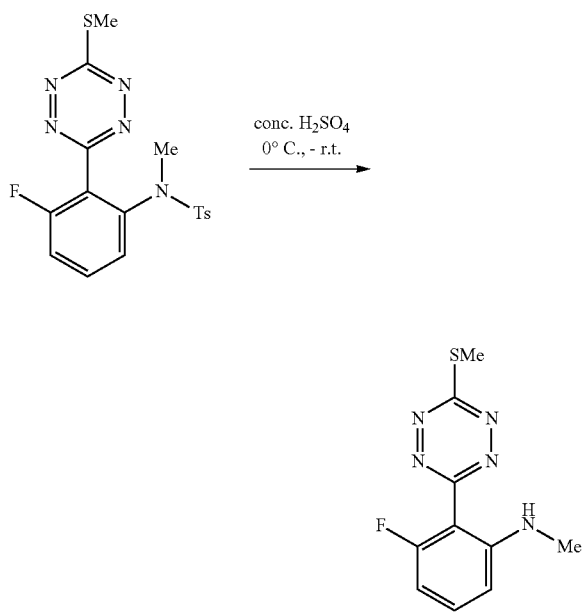

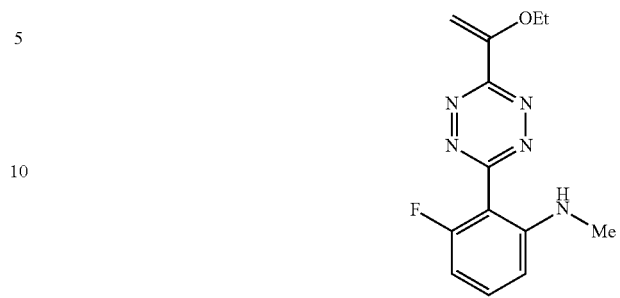

2-(6-(1-ethoxyvinyl)-1,2,4,5-tetrazin-3-yl)-3-fluoro-N-methylaniline

A dry round-bottom flask was charged with 3-fluoro-N-methyl-2-(6-(methylthio)-1,2,4,5-tetrazin-3-yl)aniline (170 mg, 0.677 mmol, 1 equiv), Pd(PPh$_3$)$_4$ (117 mg, 0.102 mmol, 15 mol %), CuTc (258 mg, 1.35 mmol, 2 equiv) and and a magnetic stirbar. The flask was outfitted with a septum-fitted gas inlet adapter, evacuated and refilled with nitrogen. Anhydrous THF (67 mL, 0.01 M) and Tributyl(1-ethoxyvinyl)tin (685 μL, 2.03 mmol, 3 equiv.) was added by syringe, and the flask was refluxing at 70° C. for 2 h. After cooling down, the reaction mixture was diluted with hexane and filtered through short pad of 10% K$_2$CO$_3$ modified silica gel. Et$_2$O was used to washed off all red fractions. The residue was concentrated by rotary evaporation. A pink solid (139 mg, 0.540 mmol, 80%) was obtained after column chromatography on 10% K$_2$CO$_3$ modified silica gel (Hexane:ether 10:0 to 8:2). $^1$H NMR (400 MHz, CDCl$_3$) δ 7.59 (s, 1H), 7.38 (td, J=8.3, 6.1 Hz, 1H), 6.73-6.45 (m, 2H), 6.06 (d, J=3.0 Hz, 1H), 4.96 (d, J=3.0 Hz, 1H), 4.14 (q, J=7.0 Hz, 2H), 2.94 (d, J=5.0 Hz, 3H), 1.56 (t, J=4.9 Hz, 3H). $^{13}$C NMR (101 MHz, CDCl$_3$) δ 164.91 (d, J=5.63 Hz, C), 163.28 (d, J=254.5 Hz, C), 159.00 (C), 158.99 (C), 153.54 (C), 150.80 (d, J=4.45 Hz, C), 134.24 (d, J=12.02 Hz, CH), 107.10 (d, J=2.91 Hz, CH), 103.73 (d, J=22.9 Hz, CH), 93.53 (CH$_2$), 64.65 (CH$_2$), 30.54 (CH$_3$), 14.53 (CH$_3$). HRMS [M+H]$^+$ m/z calcd. for [C$_{13}$H$_{15}$ON$_5$F]$^+$ 276.1261, found 276.1254.

3-fluoro-N-methyl-2-(6-(methylthio)-1,2,4,5-tetrazin-3-yl)aniline

A round-bottom flask was charged with N-(3-fluoro-2-(6-(methylthio)-1,2,4,5-tetrazin-3-yl)phenyl)-N,4-dimethyl-benzenesulfonamide (270 mg, 0.666 mmol, 1 equiv) and a magnetic stir bar. Concentrated sulfuric acid (2.14 mL, 40.0 mmol, 60 equiv) was added at 0° C. After stirring at 0° C. for 5 min followed by room temperature for 45 min, the resulting mixture was added into aqueous sodium carbonate solution dropwise at 0° C. until pH>7 (gas generate, must add slowly). The resulting mixture was extracted with DCM three times. All organic layers were combined and washed with water three times, brine, brine, dried over sodium sulfate and concentrated by rotary evaporation. A red oil (168 mg, 0.666 mmol, 100%) product was obtained and used directly in next step without further purification. $^1$H NMR (400 MHz, CDCl$_3$) δ 7.36 (td, J=8.3, 6.3 Hz, 1H), 6.94 (s, 1H), 6.71-6.46 (m, 2H), 2.93 (d, J=5.0 Hz, 3H), 2.80 (s, 3H). $^{13}$C NMR (101 MHz, CDCl$_3$) δ 173.24 (C), 162.78 (d, J=252.4 Hz, C), 162.63 (d, J=4.76 Hz, C), 150.19 (d, J=2.35 Hz, C), 150.17 (d, J=4.44 Hz, C), 133.74 (d, J=12.01 Hz, CH), 106.93 (d, J=2.74 Hz, CH), 103.98 (d, J=12.6 Hz, C), 103.86 (d, J=22.9 Hz, CH), 30.58 (CH$_3$), 13.49 (CH$_3$). HRMS [M+H]$^+$ m/z calcd. for [C$_{10}$H$_{11}$N$_5$FS]$^+$ 252.0719, found 252.0711.

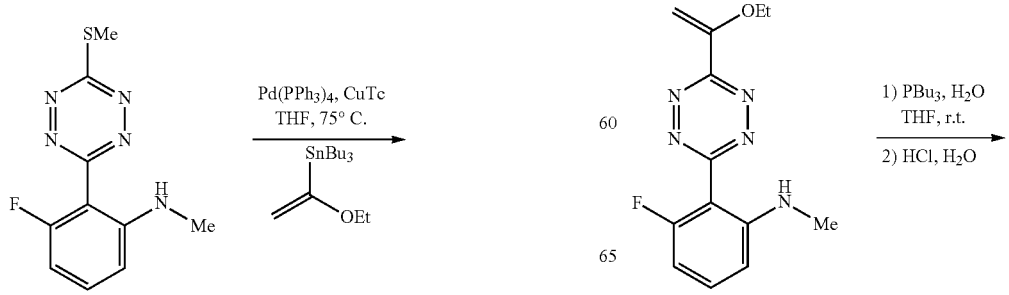

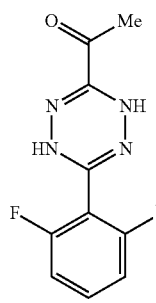

1-(6-(2-fluoro-6-(methylamino)phenyl)-1,4-dihydro-1,2,4,5-tetrazin-3-yl)ethan-1-one A round-bottom flask was charged with 2-(6-(1-ethoxyvinyl)-1,2,4,5-tetrazin-3-yl)-3-fluoro-N-methylaniline (125 mg, 0.486 mmol, 1 equiv) and a magnetic stir bar. The flask was outfitted with a septum-fitted gas inlet adapter, evacuated and refilled with nitrogen. Anhydrous THF (4.8 mL, 0.1 M), PBu$_3$ (240 µL, 0.972 mmol, 2 equiv) and water (87.0 µL, 4.86 mmol, 10 equiv) was added by syringe. After stirring at room temperature for 3 h, 1M HCl (9.6 mL, 97.2 mmol, 20 equiv) was added by syringe. After stirring at room temperature overnight, the resulting mixture was diluted with DCM, neutralized by saturate sodium bicarbonate solution until pH>7, washed with water and brine, dried over sodium sulfate, and concentrated by rotary evaporation. A yellow solid (99.3 mg, 0.398 mmol, 82%) was obtained after column chromatography (Hexane:DCM 1:1 to 15:85). $^1$H NMR (400 MHz, CDCl$_3$) δ 7.70 (d, J=12.3 Hz, 1H), 7.48 (s, 1H), 7.25-7.15 (m, 1H), 7.08 (s, 1H), 6.44 (d, J=8.5 Hz, 1H), 6.38 (dd, J=13.0, 8.2 Hz, 1H), 2.86 (d, J=5.0 Hz, 3H), 2.46 (s, 3H). $^{13}$C NMR (101 MHz, CDCl$_3$) δ 191.40 (C), 162.41 (d, J=243.2 Hz, C), 150.53 (d, J=5.83 Hz, C), 145.17 (C), 144.63 (C), 132.26 (d, J=12.9 Hz, CH), 106.78 (d, J=2.14 Hz, CH), 102,40 (d, J=24.5 Hz, CH), 99.18 (d, H=12.04 Hz, C), 30.40 (CH$_3$), 24.778 (CH$_3$). HRMS [M+H]$^+$ m/z calcd. for [C$_{11}$H$_{13}$ON$_5$F]$^+$ 250.1104, found 250.1056.

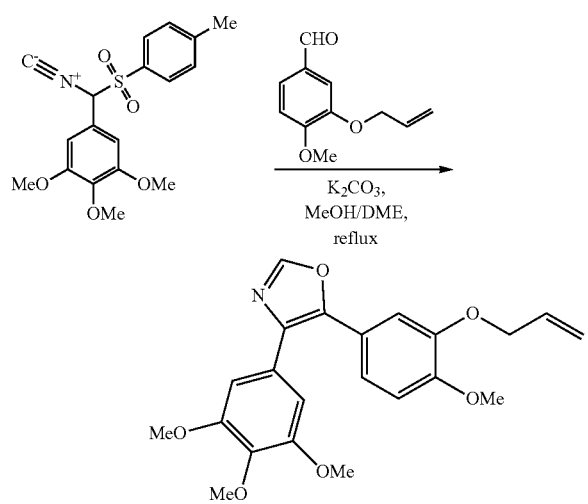

5-(3-(allyloxy)-4-methoxyphenyl)-4-(3,4,5-trimethoxyphenyl)oxazole

A dry round-bottom flask was charged with 5-(isocyano(tosyl)methyl)-1,2,3-trimethoxybenzene (256 mg, 0.710 mmol, 1.4 equiv.), 3-(allyloxy)-4-methoxybenzaldehyde (138 mg, 0.507 mmol, 1 equiv.), potassium carbonate (140 mg, 1.01 mmol, 2 equiv.) anhydrous MeOH (5 mL, 0.1 M), DME (1.6 mL) and a magnetic stirbar. After refluxing under nitrogen at 65° C. for 3 h, the resulting mixture was concentrated and redissolved in EA, washed with water and brine, dried over sodium sulfate and concentrated by rotary evaporation. A colorless oil (102 mg, 0.213 mmol, 42%) was obtained after column chromatography (hexane:EA 10:0 to 7:3). $^1$H NMR (400 MHz, CDCl$_3$) δ 7.91 (s, 1H), 7.24 (dd, J=8.4, 2.1 Hz, 1H), 7.13 (d, J=2.0 Hz, 1H), 6.97-6.71 (m, 3H), 6.01 (ddt, J=17.3, 10.7, 5.5 Hz, 1H), 5.39-5.19 (m, 2H), 4.52 (dt, J=5.5, 1.5 Hz, 2H), 3.91 (s, 1H), 3.87 (s, 1H), 3.79 (s, 6H). $^{13}$C NMR (101 MHz, CDCl$_3$) δ 153.42 (C), 150.06 (C), 149.33 (C), 148.01 (C), 145.74 (C), 137.92 (C), 133.67 (C), 132.85 (CH), 127.80 (C), 121.25 (C), 120.40 (CH), 118.61 (C), 112.03 (CH), 111.44 (CH), 104.99 (CH), 69.98 (CH$_2$), 61.08 (CH$_3$), 56.22 (CH$_3$), 56.10 (CH$_3$).

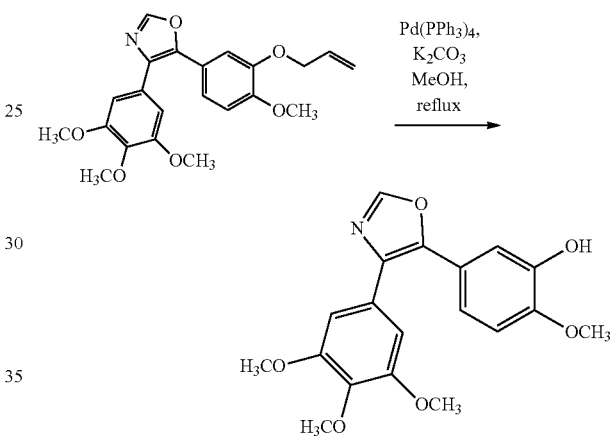

2-methoxy-5-(4-(3,4,5-trimethoxyphenyl)oxazol-5-yl)phenol

A dry round-bottom flask was charged with 5-(3-(allyloxy)-4-methoxyphenyl)-4-(3,4,5-trimethoxyphenyl)oxazole (15.5 mg, 0.0390 mmol, 1 equiv.), tetrakis(triphenylphosphine) palladium(0) (11.3 mg, 0.00975 mmol, 25 mol %), potassium carbonate (27.0 mg, 0.195 mmol, 5 equiv.) and a magnetic stirbar. The flask was outfitted with a septum-fitted gas inlet adapter, evacuated and refilled with nitrogen. Anhydrous MeOH (2 mL) was added by syringe. After refluxing under nitrogen at 70° C. for 6, the resulting mixture was filtered through celite. Celite was washed with DCM. All organic fractions were combined and concentrated by rotary evaporation. A white solid (13.1 mg, 0.0367 mmol, 93%) was obtained after column chromatography (DCM:EA 100:0 to 95:5). $^1$H NMR (600 MHz, CDCl$_3$) δ 7.91 (s, 1H), 7.26 (d, J=2.1 Hz, 1H), 7.17 (dd, J=8.4, 2.1 Hz, 1H), 6.93 (s, 2H), 6.87 (d, J=8.4 Hz, 1H), 5.72 (s, 1H), 3.93 (s, 3H), 3.89 (s, 3H), 3.80 (s, 6H). $^{13}$C NMR (101 MHz, CDCl$_3$) δ 153.38 (C), 149.40 (C), 147.24 (C), 145.78 (C), 145.60 (C), 137.91 (C), 133.73 (C), 127.69 (C), 122.05 (C), 119.58 (CH), 113.4 (CH), 110.64 (CH), 104.92 (CH), 61.10 (CH$_3$), 56.21 (CH$_3$), 56.12 (CH$_3$).

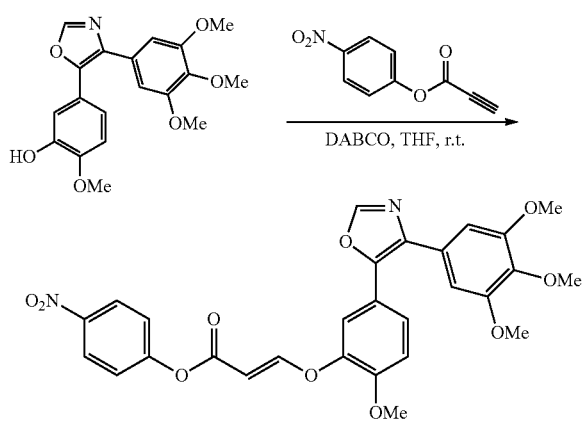

4-nitrophenyl (E)-3-(2-methoxy-5-(4-(3,4,5-trimethoxyphenyl)oxazol-5-yl)phenoxy)acrylate A dry round bottom flask was charged with 2-methoxy-5-(4-(3,4,5-trimethoxyphenyl)oxazol-5-yl)phenol (148 mg, 0.414 mmol, 1 equiv), DABCO (4.64 mg, 0.0414 mmol, 0.1 equiv), 4-nitrophenol propiolate (95.0 mg, 0.497 mmol, 1.2 equiv) and magnetic stir bar. The flask was outfitted with a septum-fitted gas inlet adapter, evacuated and refilled with nitrogen. Anhydrous THF (4 mL, 0.1 M) was added by syringe. After stirring at room temperature overnight, the mixture was diluted with DCM, washed with water and brine, dried over sodium sulfate, and concentrated by rotary evaporation. A white solid (177 mg, 0.322 mmol, 78%) was obtained after column chromatography (DCM:EA 100:0 to 88:12). $^1$H NMR (400 MHz, CDCl$_3$) δ 8.26 (d, J=9.1 Hz, 2H), 7.93 (s, 1H), 7.89 (d, J=12.2 Hz, 1H), 7.53 (dd, J=8.6, 2.2 Hz, 1H), 7.43 (d, J=2.1 Hz, 1H), 7.37-7.28 (m, 2H), 7.03 (d, J=8.6 Hz, 1H), 6.89 (s, 2H), 5.59 (d, J=12.2 Hz, 1H), 3.92 (s, 3H), 3.88 (s, 3H), 3.80 (s, 6H). $^{13}$C NMR (101 MHz, CDCl$_3$) δ 164.64 (C), 163.31 (CH), 155.55 (C), 153.55 (C), 150.86 (C), 149.65 (C), 145.25 (C), 144.27 (C), 143.99 (C), 138.27 (C), 134.50 (C), 127.35 (C), 125.63 (CH), 125.26 (CH), 122.66 (CH), 122.03 (C), 119.38 (CH), 113.01 (CH), 105.04 (CH), 99.59 (CH), 61.07 (CH$_3$), 56.28 (CH$_3$), 56.25 (CH$_3$). HRMS [M+H]$^+$ m/z calcd. for [C$_{28}$H$_{25}$O$_{10}$N$_2$]$^+$ 549.1509, found 549.1492.

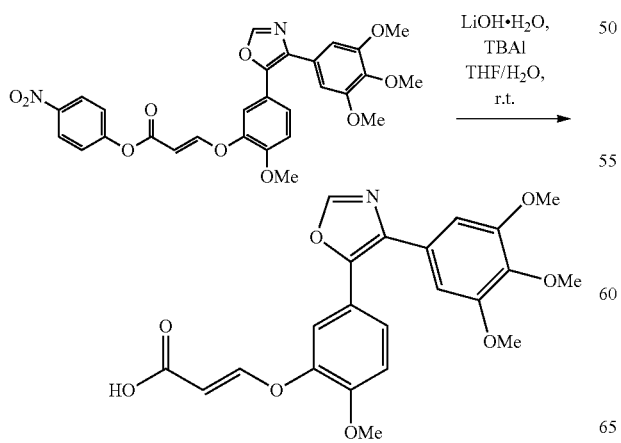

(E)-3-(2-methoxy-5-(4-(3,4,5-trimethoxyphenyl)oxazol-5-yl)phenoxy)acrylic Acid

A round bottom flask was charged with 4-nitrophenyl (E)-3-(2-methoxy-5-(4-(3,4,5-trimethoxyphenyl)oxazol-5-yl)phenoxy)acrylate (80.7 mg, 0.147 mmol, 1 equiv), lithium hydroxide monohydrate (18.5 mg, 0.441 mmol, 3 equiv), tetrabutylammonium iodide (54.3 mg, 0.147 mmol, 1 equiv), THF (0.8 mL), water (0.8 mL) and magnetic stir bar. After heating at 35° C. for 24 h, the mixture was acidified by 1M HCl (1.2 mL) until pH<3, diluted with DCM, washed with water and brine, dried over sodium sulfate, and concentrated by rotary evaporation. A white solid (60 mg, 0.141 mmol, 96%) was obtained after column chromatography (DCM:MeOH 100:0 to 95:5). $^1$H NMR (400 MHz, CDCl$_3$) δ 7.93 (s, 1H), 7.75 (d, J=12.2 Hz, 1H), 7.49 (dd, J=8.6, 2.2 Hz, 1H), 7.39 (d, J=2.1 Hz, 1H), 6.99 (d, J=8.7 Hz, 1H), 6.88 (s, 2H), 5.40 (d, J=12.2 Hz, 1H), 3.89 (s, 3H), 3.88 (s, 3H), 3.80 (s, 6H). $^{13}$C NMR (101 MHz, CDCl$_3$) δ 171.97 (C), 162.22 (CH), 153.55 (C), 150.93 (C), 149.67 (C), 144.43 (C), 144.20 (C), 138.24 (C), 134.38 (C), 127.38 (C), 125.31 (CH), 121.92 (C), 119.26 (CH), 112.90 (CH), 105.03 (CH), 100.67 (CH), 61.11 (CH$_3$), 56.26 (CH$_3$), 56.25 (CH$_3$). HRMS [M+H]$^+$ m/z calcd. for [C$_{22}$H$_{22}$O$_8$N]$^+$ 428.1345, found 428.1332.

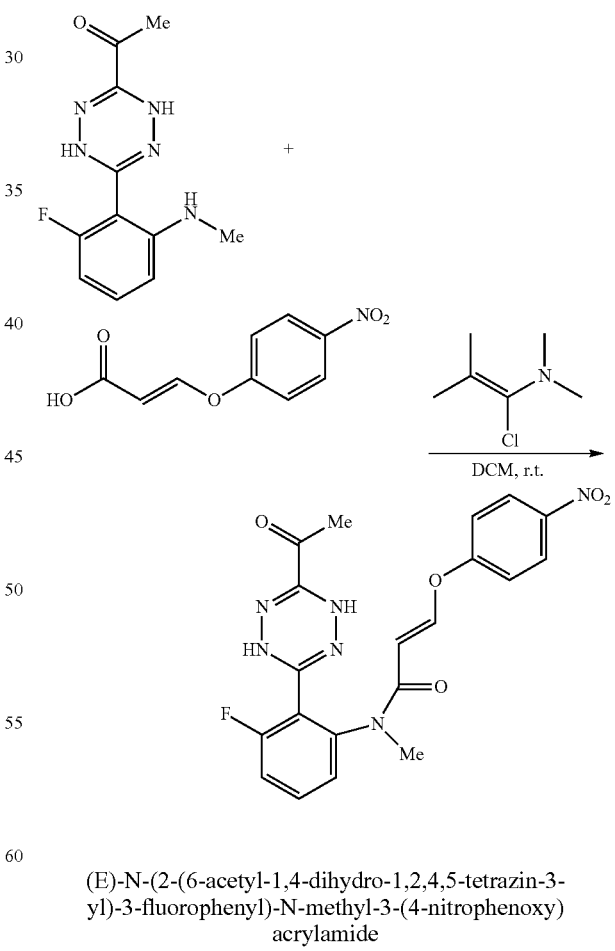

(E)-N-(2-(6-acetyl-1,4-dihydro-1,2,4,5-tetrazin-3-yl)-3-fluorophenyl)-N-methyl-3-(4-nitrophenoxy)acrylamide A dry round-bottom flask was charged with (E)-3-(4-nitrophenoxy)acrylic acid (29.0 mg, 0.139 mmol, 3 equiv) and a magnetic stir bar. The flask was outfitted with a septum-fitted gas inlet adapter, evacuated and refilled with nitrogen. Anhydrous DCM (1.3 mL, 0.1 M) and 1-chloro-N,N-2-trimethylpropenlamine (24.5 µL, 0.185 mmol, 4 equiv) was added by syringe. After stirring at room temperature for 1.5 h, 1-(6-(2-fluoro-6-(methylamino)phenyl)-1,4-dihydro-1,2,4,5-tetrazin-3-yl)ethan-1-one (11.5 mg, 0.0462 mmol, 1 equiv) was added and stirred at room temperature for another 1 h. The resulting mixture was diluted with EA, washed with saturate sodium bicarbonate solution for three times and brine, dried over sodium sulfate, and concentrated by rotary evaporation. A yellow solid (10.5 mg, 0.0238 mmol, 52%) was obtained after column chromatography (Hexane:acetone 10:0 to 7:3) and prep HPLC purification (Method: flow rate 3.3 mL/min, time 60 min, 3.3 mL per collection fraction, DCM:EA 91:9).

$^1$H NMR (400 MHz, CDCl$_3$) δ 8.24 (d, J=8.9 Hz, 2H), 7.80 (d, J=11.5 Hz, 1H), 7.62-7.49 (m, 2H), 7.28-7.18 (m, 1H), 7.13 (d, J=8.5 Hz, 3H), 6.79 (s, 1H), 5.60 (d, J=11.5 Hz, 1H), 3.27 (s, 3H), 2.44 (s, 3H). $^{13}$C NMR (101 MHz, CDCl$_3$) δ 191.06 (C), 165.42 (C), 160.98 (d, J=251.3 Hz, C), 160.64 (C), 154.21 (CH), 144.85 (d, J=2.55 Hz, C), 144.11 (C), 140.23 (C), 132.71 (d, J=9.95 Hz, CH), 126.18 (CH), 125.98 (d, J=3.23 Hz, CH), 118.22 (C), 118.08 (C), 117.12 (CH), 116.54 (d, J=21.46 Hz, CH), 105.80 (CH), 37.53 (CH$_3$), 24.90 (CH$_3$).

(E)-N-(2-(6-acetyl-1,4-dihydro-1,2,4,5-tetrazin-3-yl)-3-fluorophenyl)-3-(2-methoxy-5-(4-(3,4,5-trimethoxyphenyl)oxazol-5-yl)phenoxy)-N-methylacrylamide A dry round-bottom flask was charged with (E)-3-(2-methoxy-5-(4-(3,4,5-trimethoxyphenyl)oxazol-5-yl)phenoxy)acrylic acid (41.4 mg, 0.0969 mmol, 1.5 equiv) and a magnetic stir bar. The flask was outfitted with a septum-fitted gas inlet adapter, evacuated and refilled with nitrogen. Anhydrous DCM (1 mL, 0.1 M) and 1-chloro-N,N-2-trimethylpropenlamine (25.6 µL, 0.194 mmol, 3 equiv) was added by syringe. After stirring at room temperature for 1 h, 1-(6-(2-fluoro-6-(methylamino)phenyl)-1,4-dihydro-1,2,4,5-tetrazin-3-yl)ethan-1-one (16.1 mg, 0.0646 mmol, 1 equiv) was added and stirred at room temperature for another 1 h. The resulting mixture was diluted with DCM, washed with saturate sodium bicarbonate solution for three times and brine, dried over sodium sulfate, and concentrated by rotary evaporation. A yellow solid (mg, mmol, %) was obtained after column chromatography (DCM:MeOH 100:0 to 98:2) and prep HPLC purification (Method: DCM:MeOH 98.5:1.5, flow rate 3.3 mL/min, time 60 min, 3.3 mL per fraction, product retention time=20-24 min). $^1$H NMR (400 MHz, CDCl$_3$) δ 7.95 (s, 1H), 7.69 (d, J=11.6 Hz, 1H), 7.56 (s, 1H), 7.54-7.47 (m, 1H), 7.45-7.37 (m, 2H), 7.21 (t, J=8.8 Hz, 1H), 7.12 (d, J=7.9 Hz, 1H), 6.93 (d, J=8.7 Hz, 1H), 6.90 (s, 2H), 6.84 (s, 1H), 5.42 (d, J=11.7 Hz, 1H), 3.91 (s, 3H), 3.89 (s, 3H), 3.81 (s, 6H), 3.27 (s, 3H), 2.45 (s, 3H). $^{13}$C NMR (101 MHz, CDCl$_3$) δ 191.14 (C), 165.97 (C), 161.12 (d, J=238.0 Hz, C), 158.54 (CH), 153.53 (C), 150.57 (C), 149.62 (C), 145.31 (C), 144.93 (C), 144.53 (C), 144.04 (C), 140.35 (C), 138.20 (C), 134.37 (C), 132.58 (d, J=9.89 Hz, CH), 127.42 (C), 125.94 (CH), 124.62 (CH), 121.90 (C), 118.44 (C), 118.21 (CH), 116.21 (d, J=21.04 Hz, CH), 112.54 (CH), 105.00 (CH), 102.42 (CH), 61.12 (CH$_3$), 56.27 (CH$_3$), 56.27 (CH$_3$), 37.32 (CH$_3$), 24.88 (CH$_3$). HRMS [M+H]$^+$ m/z calcd. for [C$_{33}$H$_{32}$O$_8$N$_6$F]$^+$ 659.2266, found 659.2248.

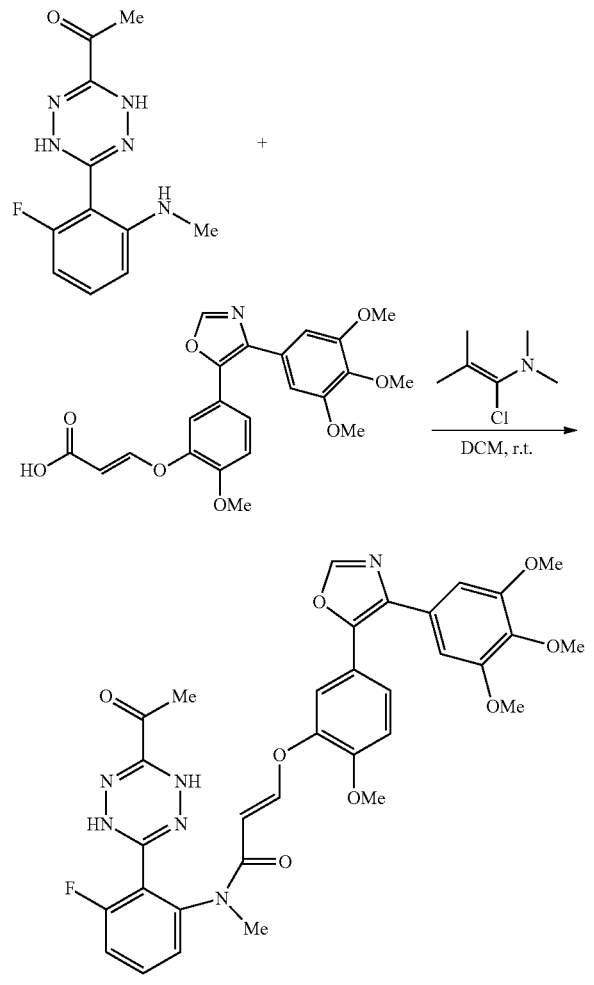

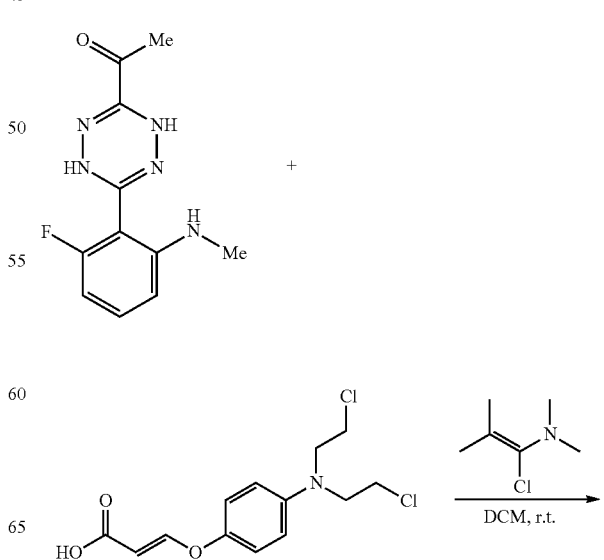

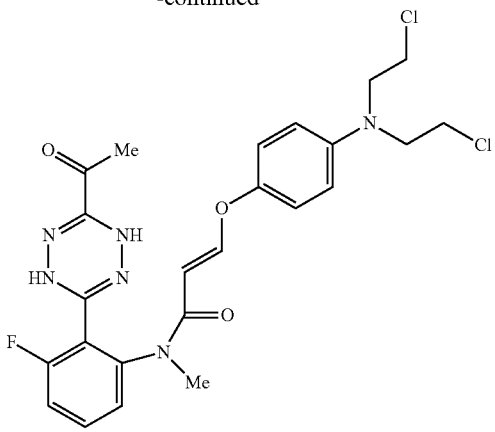

(E)-N-(2-(6-acetyl-1,4-dihydro-1,2,4,5-tetrazin-3-yl)-3-fluorophenyl)-3-(4-(bis(2-chloroethyl)amino)phenoxy)-N-methylacrylamide A dry round-bottom flask was charged with (E)-3-(4-(bis(2-chloroethyl)amino) phenoxy)acrylic acid (30.7 mg, 0.124 mmol, 1.5 equiv) and a magnetic stir bar. The flask was outfitted with a septum-fitted gas inlet adapter, evacuated and refilled with nitrogen. Anhydrous DCM (1.2 mL, 0.1 M) and 1-chloro-N,N-2-trimethylpropenlamine (32.8 µL, 0.248 mmol, 3 equiv) was added by syringe. After stirring at room temperature for 1 h, 1-(6-(2-fluoro-6-(methylamino)phenyl)-1,4-dihydro-1,2,4,5-tetrazin-3-yl)ethan-1-one (20.6 mg, 0.0826 mmol, 1 equiv) was added and stirred at room temperature for another 1 h. The resulting mixture was diluted with DCM, washed with saturate sodium bicarbonate solution for three times and brine, dried over sodium sulfate, and concentrated by rotary evaporation. A yellow solid (16.5 mg, 0.0307 mmol, 37%) was obtained after column chromatography (DCM:MeOH 100:0 to 99:1) and prep HPLC purification (Method: flow rate 3.3 mL/min, time 60 min, 3.3 mL per collection fraction, DCM:EtOH 99.5:0.5). $^1$H NMR (400 MHz, CD$_3$CN) δ 7.71 (s, 1H), 7.58-7.53 (m, 2H), 7.26 (t, J=9.0 Hz, 1H), 7.18 (d, J=8.0 Hz, 1H), 6.92 (d, J=8.6 Hz, 2H), 6.72 (d, J=8.6 Hz, 2H), 5.24 (d, J=11.0 Hz, 1H), 3.79-3.53 (m, 8H), 3.16 (s, 3H), 2.35 (s, 3H). $^{13}$C NMR (101 MHz, CDCl$_3$) δ 191.14 (C), 166.34 (C), 161.08 (d, J=257.9 Hz, C), 158.82 (CH), 148.57 (C), 145.04 (C), 144.02 (C), 143.50 (C), 140.35 (C), 132.54 (d, J=9.89 Hz, C), 125.98, 119.16 (CH), 118.17 (C), 116.14 (d, J=21.9 Hz, CH), 113.27 (CH), 101.50 (CH), 53.91 (CH$_2$), 40.54 (CH$_2$), 37.31 (CH$_3$), 24.91 (CH$_3$).

Synthesis of 6-Fluoropyridyl Acetyl DHT

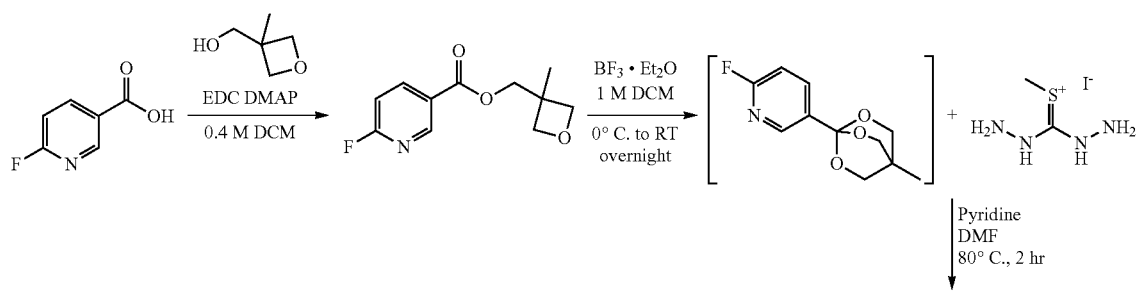

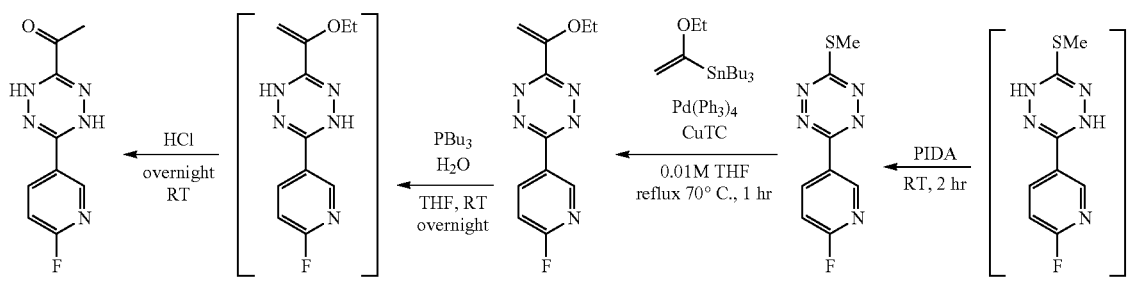

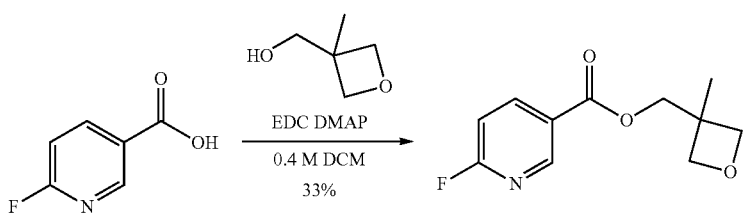

A dry round-bottom flask was charged with EDC.HCl (3.916 g, 19.88 mmol, 1.2 eq), 3-methyl-3-oxetanemethanol (2.024 mL, 19.88 mmol, 1.2 eq) and DMAP (211 mg, 1.656 mmol, 0.1 eq). The flask was then attached to a septum-fitted gas inlet adapter and then evacuated and filled with nitrogen. Anhydrous DCM (51 mL, 0.4M) was added to the flask via syringe. The flask was cooled to 0° C. with an ice bath and 6-fluoronicotinic acid (2.337 g, 16.56 mmol, 1 eq) was added. The solution stirred at 0° C. for 15 minutes and then at room temperature overnight. The reaction mixture was diluted with DCM and washed with saturated sodium bicarbonate solution, water and brine. The organic layer was dried over sodium sulfate, concentrated via rotary evaporation and purified by flash column chromatography on silica gel. A white solid (1267 mg, 5.626 mmol, 33%) was obtained after column chromatography (Hexane: EA 100:0 to 70:30). $^1$H NMR (400 MHz, CDCl$_3$) δ 8.77 (s, 1H), 8.37-8.27 (m, 1H), 6.93 (d, J=8.6 Hz, 1H), 4.49 (d, J=5.8 Hz, 2H), 4.39-4.31 (m, 4H), 1.31 (s, 3H). $^{13}$C NMR (101 MHz, CDCl$_3$) δ 167.27 (C), 164.83 (C), 164.28 (C), 150.57 (CH), 142.85 (CH), 124.40 (C), 110.02 (CH), 79.53 (CH$_2$), 69.71 (CH$_2$), 39. 41 (CH$_2$), 21.28 (CH$_3$).

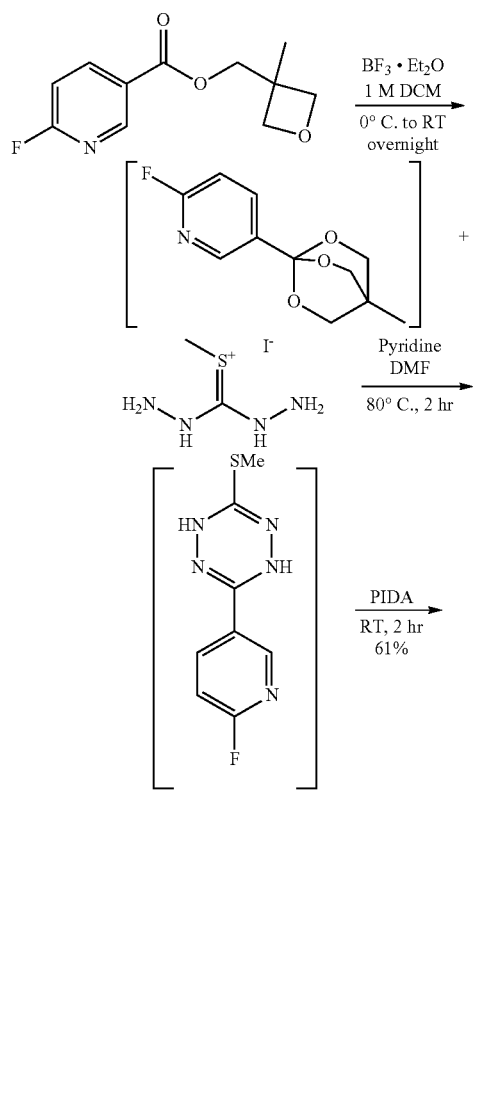

A dry round-bottom flask was charged with the oxetane ester (700.86 mg, 3.11 mmol, 1 eq) and a stir bar. The flask was then attached to a septum-fitted gas inlet adapter and then evacuated and filled with nitrogen. Anhydrous DCM (3.2 mL, 1M) was added via syringe and the flask was cooled in an ice/brine bath to 0° c. and boron trifluoride etherate (460 µL, 3.73 mmol, 1.2 eq) was added via syringe. The solution stirred on ice for 2 h and then overnight at room temperature. The reaction mixture was monitored with TLC aliquots that were quenched with triethylamine prior to spotting the TLC plate. Once the oxetane ester had been fully consumed the reaction was quenched with pyridine (751 µL, 9.33 mmol, 3 eq) and then S-methylthiocarbohydrazidium iodide (539.5 mg, 2.18 mmol, 0.7 eq) and DMF (3.1 mL, 1M) were added. The mixture was stirred vigorously, and vacuum was applied to remove DCM. The mixture was then heated via oil bath to 80° C. and allowed to stir for 2 h. After cooling to room temperature, PIDA (700.84 mg, 2.18 mmol, 0.7 eq) was added to the flask and the mixture was allowed to at room temperature for 2 h. The crude mixture was diluted with DCM and washed with saturated sodium bicarbonate solution, water and brine. The organic layer was then dried over sodium sulfate, concentrated by rotary evaporation and purified by flash column chromatography on silica gel. A red solid (295.47 mg, 1.32 mmol, 61%) was obtained after column chromatography (Hexane: EA 100:0 to 90:10). $^1$H NMR (400 MHz, CDCl$_3$) δ 9.37 (d, J=2.5 Hz, 1H), 8.88 (ddd, J=8.7, 8.0, 2.7 Hz, 1H), 7.15 (dd, J=8.6, 3.0 Hz, 1H), 2.80 (s, 3H). $^{13}$C NMR (101 MHz, CDCl$_3$) δ 176.71 (C), 167.36 (C), 164.92 (C), 160.69 (C), 148.29 (CH), 139.91 (CH), 111.00 (CH), 13.95 (CH$_3$).

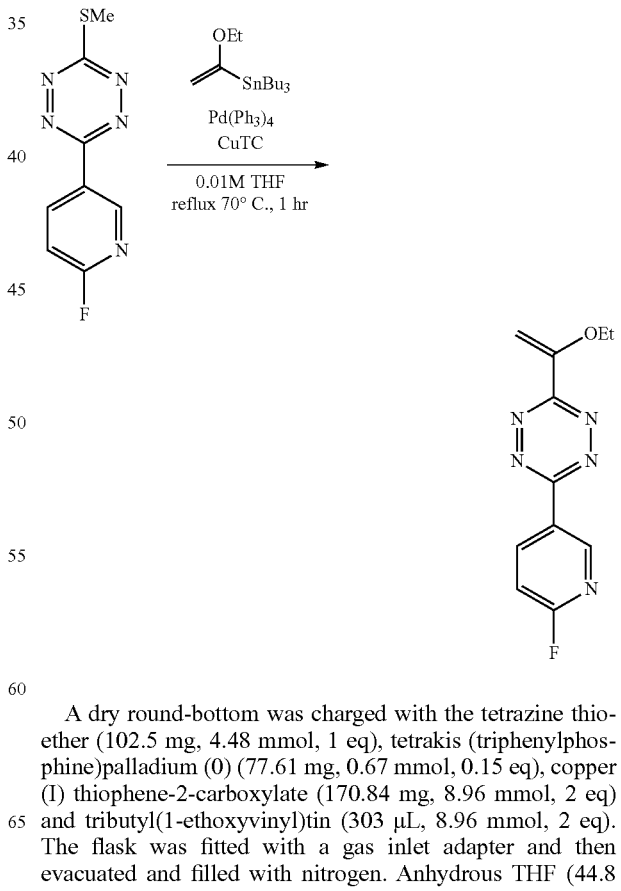

A dry round-bottom was charged with the tetrazine thioether (102.5 mg, 4.48 mmol, 1 eq), tetrakis (triphenylphosphine)palladium (0) (77.61 mg, 0.67 mmol, 0.15 eq), copper (I) thiophene-2-carboxylate (170.84 mg, 8.96 mmol, 2 eq) and tributyl(1-ethoxyvinyl)tin (303 µL, 8.96 mmol, 2 eq). The flask was fitted with a gas inlet adapter and then evacuated and filled with nitrogen. Anhydrous THF (44.8 mL, 0.01M) was added via syringe and the mixture was heated via an oil bath to 70° C. and stirred for 1 hr. The THF was removed via rotary evaporation and the residue was purified by flash column chromatography on silica gel. A pink solid (63.09 mg, 2.55 mmol, 56%) was obtained after column chromatography (Hexane: EA 100:0 to 96:4). $^1$H NMR (400 MHz, CDCl$_3$) δ 9.48 (d, J=2.4 Hz, 1H), 8.98 (ddd, J=9.0, 7.8, 2.5, 1H), 7.18 (dd, J=8.6, 3.0 Hz, 1H), 6.05 (d, J=3.0 Hz, 1H), 4.98 (d, J=3.0 Hz, 1H), 4.14 (q, J=7.0 Hz, 2H), 1.54 (t, J=7.0 Hz, 3H)$^{13}$C NMR (101 MHz, CDCl$_3$) δ 167.05 (C), 164.60 (C), 161.94 (C), 153.08 (C), 148.46 (CH), 140.46 (CH), 125.82 (C), 110.49 (CH), 93.72 (CH$_2$), 64.83 (CH$_2$), 14.15 (CH$_3$).

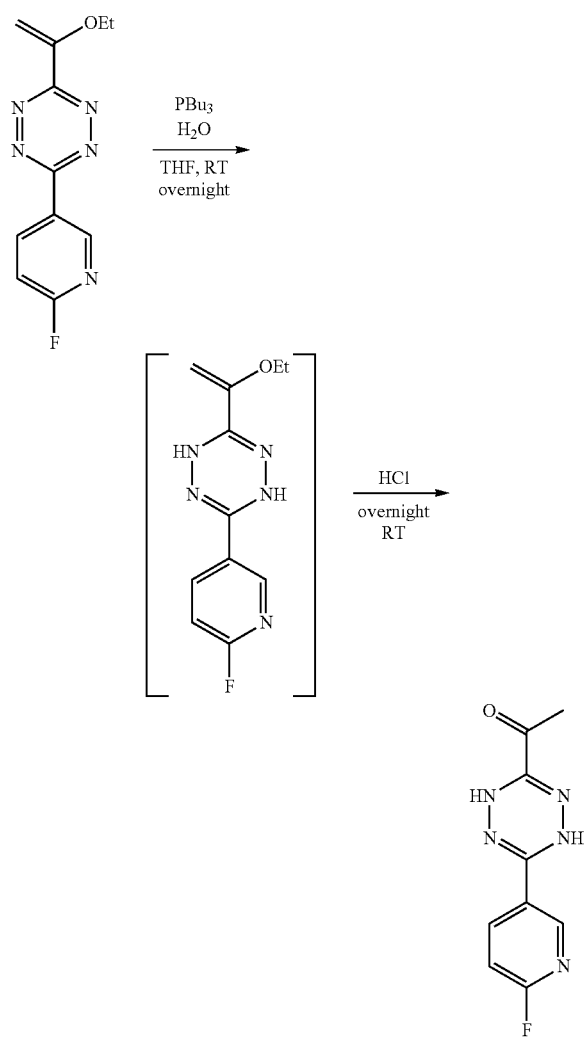

A dry round-bottom was charged with the vinyl ether tetrazine (30.61 mg, 1.21 mmol, 1 eq) and fitted with a septum-fitted gas inlet adapter. Anhydrous THF (1.5 mL, 0.08M) was added via syringe and then tributylphosphine (80 μL, 4.95 mmol, 4 eq) and deionized water (44 μL, 24.76 mmol, 20 eq) were added directly into the flask and the mixture was allowed to stir at room temperature overnight. The reaction was monitored with TLC and upon completion 1 M hydrochloric acid (1.2 mL, 12.38 mmol, 10 eq) was added and the reaction was allowed to stir at room temperature overnight. The reaction mixture was diluted with DCM, washed with brine and the organic layer was dried over sodium sulfate and concentrated via rotary evaporation. The resulting residue was purified with flash column chromatography using silica gel. An orange solid (16.98 mg, 0.77 mmol, 63%) was obtained after column chromatography (DCM: diethyl ether 100:0 to 95:5). $^1$H NMR (400 MHz, Acetone) δ 8.94 (s, 1H) 8.69-8.63 (m, 1H), 8.40-8.30 (m, 1H), 8.04 (d, J=5.2 Hz, 1H), 7.21 (dd, J=8.7, 3.0 Hz, 1H), 2.38 (s, 3H). $^{13}$C NMR (101 MHz, Acetone) δ 191.50 (C), 166.80 (C), 163.90 (C), 146.48 (CH), 140.54 (CH), 110.50 (CH), 23.17 (CH$_3$).

Oxidation of 15 by APEX2 and APEX2 Variants: F41A APEX2 and A19V D222G APEX2

15 (40 μM) from methanol stock solutions was added to PBS containing 100M EDTA. After 10s, APEX2 (275 nM) was dosed in and oxidation was monitored at 325 nm for 15. The procedure stated above was repeated for F41A APEX2 and A19V D222G APEX2. (FIG. 17). FIG. 17 shows that APEX2 and its variants, such as, F41A APEX2, and A19V D222G APEX2 can oxidize 15 and F41A, A19V, D222G mutations do not disrupt APEX2's ability to oxidize 15.

TABLE 5

Amino Acid Sequence Listing of APEX2 (SEQ ID NO: 1)

(SEQ ID NO: 1)
GKSYPTVSADYQDAVEKAKKKLRGFIAEKRCAPLMLRLAFHSAGTFDKGT

KTGGPFGTIKHPAELAHSANNGLDIAVRLLEPLKAEFPILSYADFYQLAG

VVAVEVTGGPKVPFHPGREDKPEPPPEGRLPDPTKGSDHLRDVFGKAMGL

TDQDIVALSGGHTIGAAHKERSGFEGPWTSNPLIFDNSYFTELLSGEKEG

LLQLPSDKALLSDPVFRPLVDKYAADEDAFFADYAEAHQKLSELGFADA

Although the invention is illustrated and described herein with reference to specific embodiments, the invention is not intended to be limited to the details shown. Rather, various modifications may be made in the details within the scope and range of equivalents of the claims without departing from the invention.

What is claimed:

1. A method comprising:

(a) providing a dihydrotetrazine 1 in a reaction medium, wherein the dihydrotetrazine 1 comprises a first R group and a second R group, wherein the first R group is a substituted or unsubstituted aryl, heteroaryl, alkyl, alkenyl, alkynyl, carbonyl, or heteroatom-containing group, and the second R group is selected from the group consisting of H, substituted or unsubstituted aryl, substituted or unsubstituted heteroaryl, substituted or unsubstituted alkyl, substituted or unsubstituted alkenyl, substituted or unsubstituted alkynyl, substituted or unsubstituted carbonyl containing groups, and substituted or unsubstituted heteroatom-containing groups; and

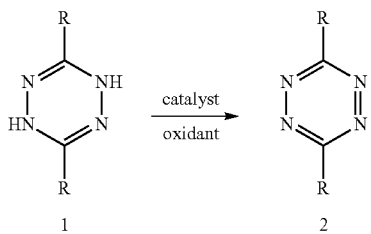

(b) adding an enzyme as a catalyst to the reaction medium, wherein the reaction medium comprises an oxidant, whereby the dihydrotetrazine 1 is catalytically converted to a tetrazine 2, wherein the enzyme is a horseradish peroxidase (HRP) or an ascorbate peroxidase, wherein the ascorbate peroxidase consists of an amino acid sequence at least 90% identical to the amino acid sequence of SEQ ID NO: 1.

2. The method according to claim 1, wherein the amino acid sequence at least 90% identical to the amino acid sequence of SEQ ID NO:1 comprises one or more mutations at positions corresponding to positions in the polypeptide of SEQ ID NO:1.

3. The method according to claim 2, wherein the one or more mutations are one or more substitutions that correspond to substitutions in the polypeptide of SEQ ID NO:1 selected from the group consisting of F41A, A19V, D222G, and a combination thereof.

4. The method according to claim 1, wherein the dihydrotetrazine 1 is converted to the tetrazine 2 in the presence of superoxide dismutase (SOD).

5. The method according to claim 1, wherein at least one of the first R group and the second R group contains an aryl vinyl ether, and wherein an aryl alcohol is released from the aryl vinyl ether in step (b).

6. The method according to claim 1, wherein the oxidant is $O_2$, optionally atmospheric $O_2$, or atmospherically-derived $O_2$ dissolved in the reaction medium.

7. The method according to claim 6, wherein the $O_2$ is at a lower partial pressure than that found under atmospheric conditions.

8. The method according to claim 6, wherein the $O_2$ is at a higher partial pressure than that found under atmospheric conditions.

9. The method according to claim 1, wherein the method is carried out in a biological milieu selected from the group consisting of living cells, living tissues, cell media, blood, serum, and cell lysates.

10. The method according to claim 1, further comprising trapping the tetrazine with a dienophile.

11. The method according to claim 1, wherein the method further comprises:
 (i) uniting one or more bimolecular entities selected from the group consisting of proteins, DNA, and RNA;
 (ii) attaching a fluorescent molecule or a fluorescent protein to another small molecule or a biomolecules or
 (iii) attaching a molecule to the surface fiber or a glass slide.

12. The method according to claim 1, wherein the dihydrotetrazine 1 has the following structure:

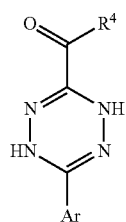

wherein $R^4$ is selected from the group consisting of H, aryl, heteroaryl, alkyl, alkenyl, alkynyl, and heteroatom-containing groups, and Ar is an aromatic or heteroaromatic group.

13. The method according to claim 12, wherein the dihydrotetrazine 1 has one of the following structures:

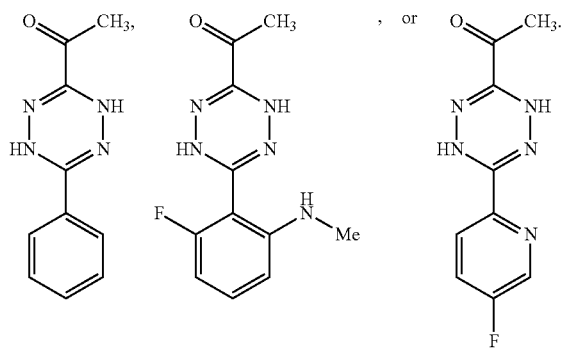

14. The method according to claim 1, wherein the dihydrotetrazine 1 is conjugated to a compound having the following structure:

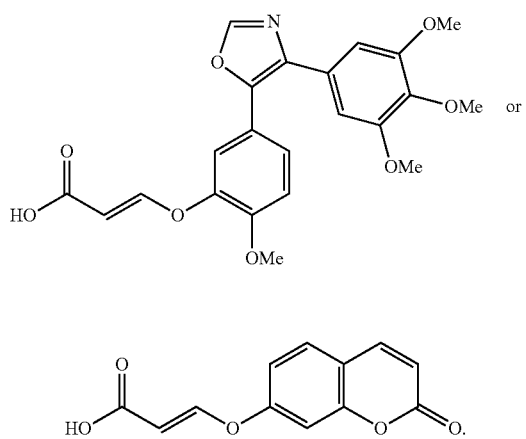

15. The method according to claim 1, wherein the dihydrotetrazine 1 has one of the following structures:

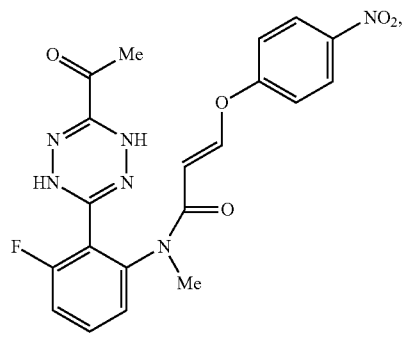

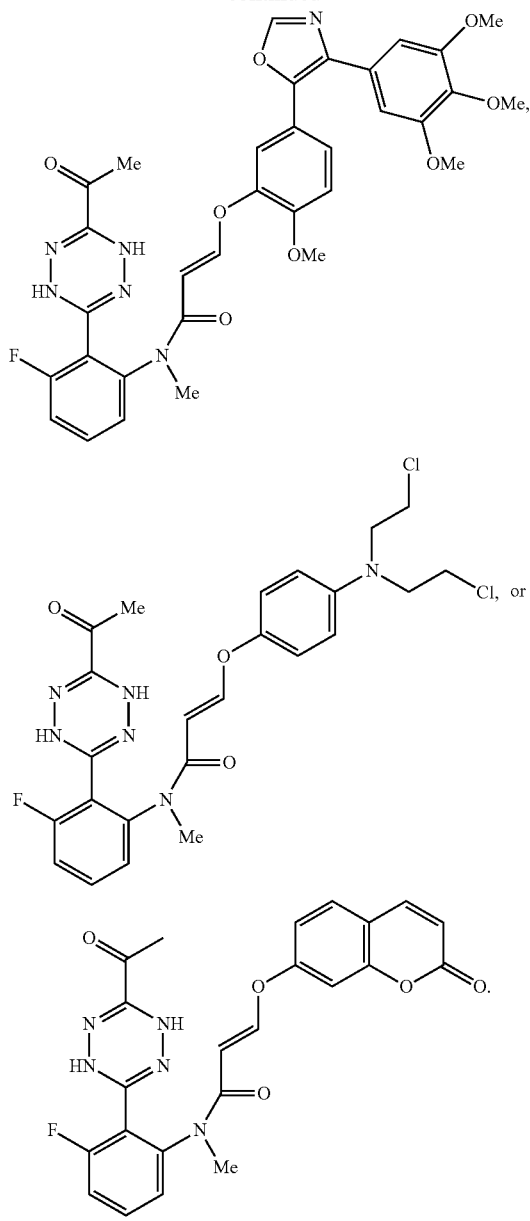
16. The method acceding to claim 1, where n the dihydrotetrazine 1 has one of the following structures:
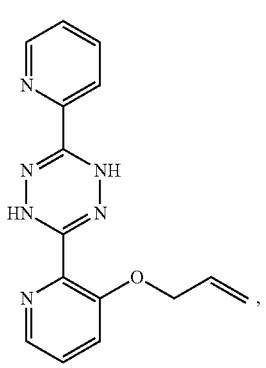
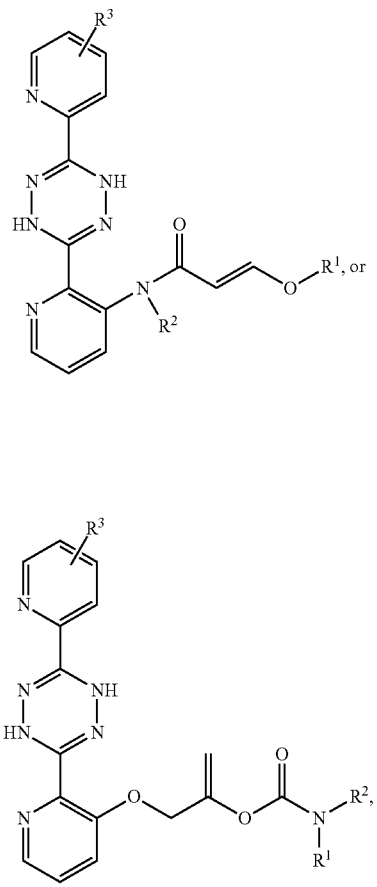
wherein $R^1$, $R^2$ and $R^3$ are each independently selected from the group consisting of H, aryl, heteroaryl, alkyl, alkenyl, alkynyl, carbonyl, and heteroatom-containing groups.
17. The method according to claim 16, wherein the dihydrotetrazine 1 has the following structure:
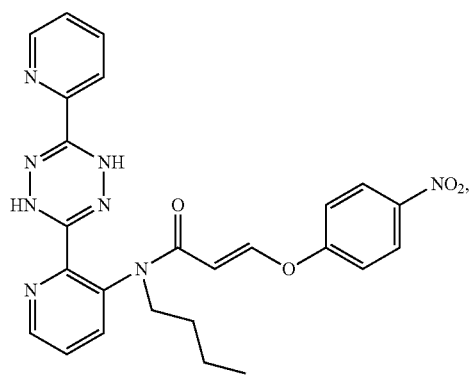

-continued
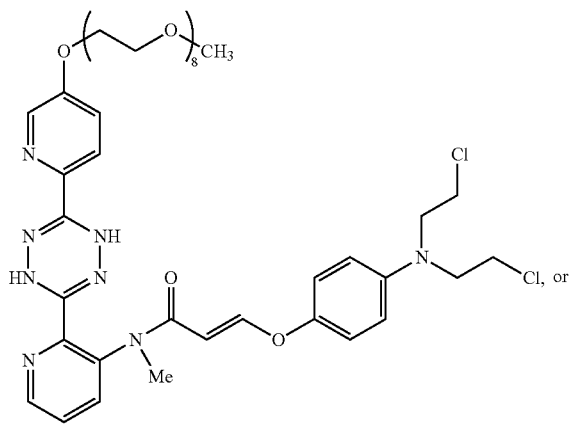
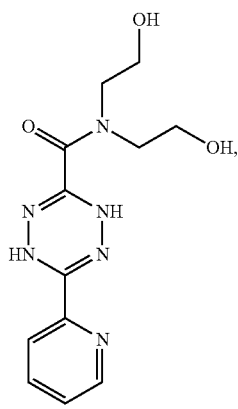
and
wherein the tetrazine 2 has the following structure:
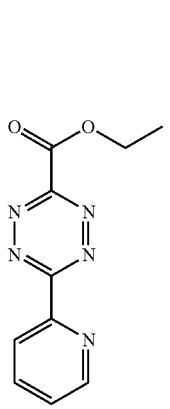
18. The method according to claim 12, wherein the dihydrotetrazine 1 has the following structure:
* * * * *